United States Patent
Mohar et al.

(10) Patent No.: US 9,241,807 B2
(45) Date of Patent: Jan. 26, 2016

(54) SYSTEMS AND METHODS FOR INSERTING A SPINAL DEVICE

(71) Applicant: Pioneer Surgical Technology, Inc., Marquette, MI (US)

(72) Inventors: Joseph Mohar, Marquette, MI (US); Jeffrey L. Trudeau, Marquette, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 249 days.

(21) Appl. No.: 13/725,322

(22) Filed: Dec. 21, 2012

(65) Prior Publication Data

US 2013/0204372 A1 Aug. 8, 2013

Related U.S. Application Data

(60) Provisional application No. 61/580,055, filed on Dec. 23, 2011.

(51) Int. Cl.
*A61F 2/00* (2006.01)
*A61B 17/88* (2006.01)
(Continued)

(52) U.S. Cl.
CPC .............. *A61F 2/442* (2013.01); *A61B 17/808* (2013.01); *A61B 17/8038* (2013.01); *A61B 17/8042* (2013.01); *A61B 17/8047* (2013.01); *A61B 17/8888* (2013.01); *A61B 17/861* (2013.01)

(58) Field of Classification Search
CPC ....... A61F 2/46; A61F 2/4603; A61F 2/4611; A61F 2002/4623; A61F 2002/4624; A61F 2002/4625; A61B 17/8841
USPC .......................................................... 606/99
See application file for complete search history.

(56) References Cited

U.S. PATENT DOCUMENTS 3,413,741 A * 12/1968 Fagan et al. .................... 38/77.3
3,867,728 A 2/1975 Stubstad et al.
(Continued)

FOREIGN PATENT DOCUMENTS

CA 2395609 2/2001
CA 2482403 9/2003
(Continued)

OTHER PUBLICATIONS

Bao et al., Artificial Disc Technology, Neurosurg. Focus 9(4), Oct. 2000, 7 pp.
(Continued)

*Primary Examiner* — Zade Coley
(74) *Attorney, Agent, or Firm* — Fitch, Even, Tabin & Flannery LLP

(57) ABSTRACT

An insertion device is provided for inserting a spinal device such as an intervertebral implant within a spinal joint. The implant includes at least first and second members, with the first having a convex articulation surface and the second member having a concave articulation surface. The two articulation surfaces provide an articulation interface to substantially mimic natural kinetic motion of the spine. The insertion device can be attached to at least one of the first and second members. In one form, the insertion device is configured such that the first and second members are movable relative to one another while being held to allow the members to form a compact wedge configuration. The insertion device is configured to actively pivot the implant about the implant gripping end of the device and to allow manipulation and release of the implant members in any pivoted orientation from approximately 0 to 90 degrees.

20 Claims, 53 Drawing Sheets

(51) Int. Cl.
*A61F 2/46* (2006.01)
*A61F 2/44* (2006.01)
*A61B 17/80* (2006.01)
*A61B 17/86* (2006.01)

(56) References Cited

U.S. PATENT DOCUMENTS

| | | |
|---|---|---|
| 3,875,595 A | 4/1975 | Froning et al. |
| 3,975,778 A | 8/1976 | Newton, III |
| 4,021,382 A | 5/1977 | Stoy |
| 4,081,402 A | 3/1978 | Levy |
| 4,147,764 A | 4/1979 | Levy |
| 4,309,777 A | 1/1982 | Patil |
| 4,349,921 A | 9/1982 | Kuntz |
| 4,454,612 A | 6/1984 | McDaniel |
| 4,650,490 A | 3/1987 | Figgie, III |
| 4,714,469 A | 12/1987 | Kenna |
| 4,728,561 A | 3/1988 | Crocker |
| 4,759,766 A | 7/1988 | Buettner-Janz |
| 4,759,769 A | 7/1988 | Hedman |
| 4,863,476 A | 9/1989 | Shepperd |
| 4,863,477 A | 9/1989 | Monson |
| 4,917,704 A | 4/1990 | Frey |
| 4,932,969 A | 6/1990 | Frey |
| 4,936,848 A | 6/1990 | Bagby |
| 4,946,378 A | 8/1990 | Hirayama |
| 4,997,432 A | 3/1991 | Keller |
| 5,002,576 A | 3/1991 | Fuhrmann |
| 5,035,716 A | 7/1991 | Downey |
| 5,047,055 A | 9/1991 | Bao |
| 5,071,437 A | 12/1991 | Steffee |
| 5,108,438 A | 4/1992 | Stone |
| 5,127,920 A | 7/1992 | MacArthur |
| 5,133,759 A | 7/1992 | Turner |
| 5,133,772 A | 7/1992 | Hack |
| 5,147,404 A | 9/1992 | Downey |
| 5,171,281 A | 12/1992 | Parsons |
| 5,176,710 A | 1/1993 | Hahn |
| 5,192,326 A | 3/1993 | Bao |
| 5,258,031 A | 11/1993 | Salib |
| 5,258,043 A | 11/1993 | Stone |
| 5,273,742 A | 12/1993 | Gould |
| 5,306,308 A | 4/1994 | Gross |
| 5,306,309 A | 4/1994 | Wagner |
| 5,314,477 A | 5/1994 | Marnay |
| 5,320,625 A | 6/1994 | Bertin |
| 5,320,644 A | 6/1994 | Baumgartner |
| 5,401,269 A | 3/1995 | Buttner-Janz |
| 5,425,773 A | 6/1995 | Boyd |
| 5,443,512 A | 8/1995 | Parr |
| 5,458,642 A | 10/1995 | Beer |
| 5,458,643 A | 10/1995 | Oka |
| 5,462,362 A | 10/1995 | Yuhta |
| 5,480,449 A | 1/1996 | Hamilton |
| 5,507,816 A | 4/1996 | Bullivant |
| 5,514,180 A | 5/1996 | Heggeness |
| 5,522,899 A | 6/1996 | Michelson |
| 5,534,028 A | 7/1996 | Bao |
| 5,549,679 A | 8/1996 | Kuslich |
| 5,556,431 A | 9/1996 | Buttner-Janz |
| 5,556,433 A | 9/1996 | Gabriel |
| 5,562,736 A | 10/1996 | Ray |
| 5,562,738 A | 10/1996 | Boyd |
| 5,571,189 A | 11/1996 | Kuslich |
| 5,595,563 A | 1/1997 | Moisdon |
| 5,609,643 A | 3/1997 | Colleran |
| 5,645,596 A | 7/1997 | Kim |
| 5,645,597 A | 7/1997 | Krapiva |
| 5,658,336 A | 8/1997 | Pisharodi |
| 5,665,122 A | 9/1997 | Kambin |
| 5,674,295 A | 10/1997 | Ray |
| 5,674,296 A | 10/1997 | Bryan |
| 5,676,701 A | 10/1997 | Yuan |
| 5,676,702 A | 10/1997 | Ratron |
| 5,683,465 A | 11/1997 | Shinn |
| 5,693,100 A | 12/1997 | Pisharodi |
| 5,702,450 A | 12/1997 | Bisserie |
| 5,716,416 A | 2/1998 | Lin |
| 5,728,762 A | 3/1998 | Reich |
| 5,755,797 A | 5/1998 | Baumgartner |
| 5,755,798 A | 5/1998 | Papavero |
| 5,782,832 A | 7/1998 | Larsen |
| 5,824,093 A | 10/1998 | Ray |
| 5,824,094 A | 10/1998 | Serhan |
| 5,860,980 A | 1/1999 | Axelson, Jr. |
| 5,865,845 A | 2/1999 | Thalgott |
| 5,865,846 A | 2/1999 | Bryan |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,919,235 A | 7/1999 | Husson |
| 5,964,807 A | 10/1999 | Gan |
| 5,969,020 A | 10/1999 | Shalaby |
| 5,976,186 A | 11/1999 | Bao |
| 5,980,572 A | 11/1999 | Kim |
| 6,001,130 A | 12/1999 | Bryan |
| 6,019,793 A | 2/2000 | Perren |
| 6,022,376 A | 2/2000 | Assell |
| 6,039,763 A | 3/2000 | Shelokov |
| RE36,758 E | 6/2000 | Fitz |
| 6,074,390 A | 6/2000 | Zucherman |
| 6,093,205 A | 7/2000 | McLeod |
| 6,093,207 A | 7/2000 | Pisharodi |
| 6,110,210 A | 8/2000 | Norton |
| 6,113,639 A | 9/2000 | Ray |
| 6,127,597 A | 10/2000 | Beyar |
| 6,132,465 A | 10/2000 | Ray |
| 6,136,031 A | 10/2000 | Middleton |
| 6,139,579 A | 10/2000 | Steffee |
| 6,143,031 A | 11/2000 | Knothe |
| 6,146,422 A | 11/2000 | Lawson |
| 6,156,067 A | 12/2000 | Bryan |
| 6,162,252 A | 12/2000 | Kuras |
| 6,179,874 B1 | 1/2001 | Cauthen |
| 6,183,518 B1 | 2/2001 | Ross |
| 6,187,048 B1 | 2/2001 | Milner |
| 6,190,387 B1 | 2/2001 | Zucherman |
| 6,206,924 B1 | 3/2001 | Timm |
| 6,224,630 B1 | 5/2001 | Bao |
| 6,240,926 B1 | 6/2001 | ChinGan |
| 6,251,140 B1 | 6/2001 | Marino |
| 6,264,695 B1 | 7/2001 | Stoy |
| 6,280,475 B1 | 8/2001 | Bao |
| 6,283,968 B1 | 9/2001 | Mehdizadeh |
| 6,283,998 B1 | 9/2001 | Eaton |
| 6,315,795 B1 | 11/2001 | Scarborough |
| 6,315,797 B1 | 11/2001 | Middleton |
| 6,348,071 B1 | 2/2002 | Steffee |
| 6,352,557 B1 | 3/2002 | Ferree |
| 6,368,350 B1 | 4/2002 | Erickson |
| 6,371,990 B1 | 4/2002 | Ferree |
| 6,375,682 B1 | 4/2002 | Fleischmann |
| 6,395,032 B1 | 5/2002 | Gauchet |
| 6,402,784 B1 | 6/2002 | Wardlaw |
| 6,402,785 B1 | 6/2002 | Zdeblick |
| 6,419,704 B1 | 7/2002 | Ferree |
| 6,428,544 B1 | 8/2002 | Ralph |
| 6,428,575 B2 | 8/2002 | Koo |
| 6,428,579 B1 | 8/2002 | Valentini |
| 6,432,106 B1 | 8/2002 | Fraser |
| 6,432,107 B1 | 8/2002 | Ferree |
| 6,432,140 B1 | 8/2002 | Lin |
| 6,436,098 B1 | 8/2002 | Michelson |
| 6,436,101 B1 | 8/2002 | Hamada |
| 6,436,102 B1 | 8/2002 | Ralph |
| 6,436,140 B1 | 8/2002 | Liu |
| 6,436,141 B2 | 8/2002 | Castro |
| 6,436,142 B1 | 8/2002 | Paes |
| 6,436,146 B1 | 8/2002 | Hassler |
| 6,440,168 B1 | 8/2002 | Cauthen |
| 6,440,170 B1 | 8/2002 | Jackson |
| 6,478,822 B1 | 11/2002 | Leroux |

(56) References Cited

U.S. PATENT DOCUMENTS

| | | |
|---|---|---|
| 6,488,716 B1 | 12/2002 | Huang |
| 6,508,839 B1 | 1/2003 | Lambrecht |
| 6,517,580 B1 | 2/2003 | Ramadan |
| 6,527,804 B1 | 3/2003 | Gauchet |
| 6,540,785 B1 | 4/2003 | Gill |
| 6,547,823 B2 | 4/2003 | Scarborough |
| 6,562,047 B2 | 5/2003 | Ralph |
| 6,579,320 B1 | 6/2003 | Gauchet |
| 6,579,321 B1 | 6/2003 | Gordon |
| 6,582,466 B1 | 6/2003 | Gauchet |
| 6,592,624 B1 | 7/2003 | Fraser |
| 6,602,291 B1 | 8/2003 | Ray |
| 6,610,091 B1 | 8/2003 | Reiley |
| 6,679,915 B1 | 1/2004 | Cauthen |
| 6,682,562 B2 | 1/2004 | Viart |
| 6,743,257 B2 | 6/2004 | Castro |
| 6,770,095 B2 | 8/2004 | Grinberg |
| 6,783,550 B2 | 8/2004 | MacArthur |
| 6,793,678 B2 | 9/2004 | Hawkins |
| 6,899,716 B2 | 5/2005 | Cragg |
| 6,936,071 B1 | 8/2005 | Marnay |
| 7,001,433 B2 | 2/2006 | Songer |
| 7,156,876 B2 | 1/2007 | Moumene |
| 7,976,550 B2 | 7/2011 | Trudeau |
| 8,012,156 B2 * | 9/2011 | Marquez Alvarez ........... 606/99 |
| 8,118,872 B2 | 2/2012 | Trudeau |
| 8,241,360 B2 | 8/2012 | Bao |
| 8,262,731 B2 | 9/2012 | Songer |
| 8,372,084 B2 | 2/2013 | Pernsteiner |
| 8,388,684 B2 | 3/2013 | Bao |
| 8,409,213 B2 | 4/2013 | Trudeau |
| 8,425,529 B2 * | 4/2013 | Milz et al. ....................... 606/99 |
| 2001/0010021 A1 | 7/2001 | Boyd |
| 2001/0012938 A1 | 8/2001 | Zucherman |
| 2001/0016772 A1 | 8/2001 | Lee |
| 2001/0016773 A1 | 8/2001 | Serhan |
| 2001/0016776 A1 | 8/2001 | Zuckerman |
| 2001/0020476 A1 | 9/2001 | Gan |
| 2001/0027343 A1 | 10/2001 | Keller |
| 2001/0032019 A1 | 10/2001 | VanDyke |
| 2001/0032020 A1 | 10/2001 | Besselink |
| 2001/0047208 A1 | 11/2001 | Michelson |
| 2001/0051829 A1 | 12/2001 | Middleton |
| 2002/0013600 A1 | 1/2002 | Scribner |
| 2002/0022883 A1 | 2/2002 | Burg |
| 2002/0022888 A1 | 2/2002 | Serhan |
| 2002/0026244 A1 | 2/2002 | Trieu |
| 2002/0029082 A1 | 3/2002 | Muhanna |
| 2002/0029083 A1 | 3/2002 | Zucherman |
| 2002/0035400 A1 | 3/2002 | Bryan |
| 2002/0045942 A1 | 4/2002 | Ham |
| 2002/0045944 A1 | 4/2002 | Muhanna |
| 2002/0049498 A1 | 4/2002 | Yuksel |
| 2002/0082608 A1 | 6/2002 | Reiley |
| 2002/0082701 A1 | 6/2002 | Zdeblick |
| 2002/0087480 A1 | 7/2002 | Sauriol |
| 2002/0099444 A1 | 7/2002 | Boyd |
| 2002/0106393 A1 | 8/2002 | Bianchi |
| 2002/0107571 A1 | 8/2002 | Foley |
| 2002/0107572 A1 | 8/2002 | Foley |
| 2002/0107573 A1 | 8/2002 | Steinberg |
| 2002/0120269 A1 | 8/2002 | Lange |
| 2002/0120270 A1 | 8/2002 | Trieu |
| 2002/0120334 A1 | 8/2002 | Crozet |
| 2002/0120336 A1 | 8/2002 | Santilli |
| 2002/0156528 A1 | 10/2002 | Gau |
| 2002/0165612 A1 | 11/2002 | Gerber |
| 2003/0009226 A1 | 1/2003 | Graf |
| 2003/0023311 A1 | 1/2003 | Trieu |
| 2003/0028197 A1 | 2/2003 | Hanson |
| 2003/0028251 A1 | 2/2003 | Mathews |
| 2003/0040799 A1 | 2/2003 | Boyd |
| 2003/0045939 A1 | 3/2003 | Casutt |
| 2003/0055427 A1 | 3/2003 | Graf |
| 2003/0074076 A1 | 4/2003 | Ferree |
| 2003/0100951 A1 | 5/2003 | Serhan |
| 2003/0135276 A1 | 7/2003 | Eckman |
| 2003/0135277 A1 | 7/2003 | Bryan |
| 2003/0135278 A1 | 7/2003 | Eckman |
| 2003/0176921 A1 | 9/2003 | Lawson |
| 2003/0204260 A1 | 10/2003 | Ferree |
| 2003/0204261 A1 | 10/2003 | Eisermann |
| 2003/0220691 A1 | 11/2003 | Songer |
| 2004/0024462 A1 | 2/2004 | Ferree |
| 2004/0030391 A1 | 2/2004 | Ferree |
| 2004/0044410 A1 | 3/2004 | Ferree |
| 2004/0073315 A1 * | 4/2004 | Justin et al. ................. 623/20.15 |
| 2004/0082999 A1 | 4/2004 | Mathys |
| 2004/0093082 A1 | 5/2004 | Ferree |
| 2004/0102846 A1 | 5/2004 | Keller |
| 2004/0117019 A1 | 6/2004 | Trieu |
| 2004/0117022 A1 | 6/2004 | Marnay |
| 2004/0133278 A1 | 7/2004 | Marino |
| 2004/0153065 A1 * | 8/2004 | Lim .................................. 606/53 |
| 2004/0153157 A1 | 8/2004 | Keller |
| 2004/0204760 A1 | 10/2004 | Fitz |
| 2005/0021042 A1 | 1/2005 | Marnay |
| 2005/0021143 A1 | 1/2005 | Keller |
| 2005/0021149 A1 | 1/2005 | Borruto |
| 2005/0033437 A1 | 2/2005 | Bao |
| 2005/0060034 A1 | 3/2005 | Berry |
| 2005/0071011 A1 | 3/2005 | Ralph |
| 2005/0085911 A1 | 4/2005 | Link |
| 2005/0085917 A1 | 4/2005 | Marnay |
| 2005/0165485 A1 | 7/2005 | Trieu |
| 2005/0192671 A1 | 9/2005 | Bao |
| 2005/0266581 A1 | 12/2005 | Droit |
| 2005/0283245 A1 * | 12/2005 | Gordon et al. ............. 623/17.15 |
| 2006/0004453 A1 | 1/2006 | Bartish |
| 2006/0020342 A1 | 1/2006 | Ferree |
| 2006/0041614 A1 | 2/2006 | Oe |
| 2006/0212122 A1 | 9/2006 | Perera |
| 2006/0235426 A1 * | 10/2006 | Lim et al. ........................ 606/99 |
| 2006/0235527 A1 | 10/2006 | Buettner-Janz |
| 2006/0235528 A1 | 10/2006 | Buettner-Janz |
| 2006/0235531 A1 | 10/2006 | Buettner-Janz |
| 2007/0027547 A1 | 2/2007 | Rydell |
| 2007/0093850 A1 * | 4/2007 | Harris et al. .................... 606/99 |
| 2007/0100454 A1 | 5/2007 | Burgess |
| 2007/0142843 A1 * | 6/2007 | Dye .................................. 606/99 |
| 2008/0009880 A1 * | 1/2008 | Warnick et al. ................. 606/99 |
| 2008/0077153 A1 * | 3/2008 | Pernsteiner et al. ............. 606/99 |
| 2008/0077241 A1 * | 3/2008 | Nguyen ....................... 623/17.11 |
| 2008/0109081 A1 | 5/2008 | Bao |
| 2008/0288081 A1 | 11/2008 | Scrafton |
| 2008/0306488 A1 * | 12/2008 | Altarac et al. .................. 606/99 |
| 2008/0306489 A1 * | 12/2008 | Altarac et al. .................. 606/99 |
| 2009/0043390 A1 | 2/2009 | Meisel |
| 2009/0054901 A1 * | 2/2009 | Oh et al. ......................... 606/99 |
| 2009/0164023 A1 | 6/2009 | Devine |
| 2009/0185904 A1 | 7/2009 | Landberg |
| 2009/0228054 A1 * | 9/2009 | Hoffman et al. ............. 606/86 A |
| 2010/0249797 A1 * | 9/2010 | Trudeau et al. ................. 606/99 |
| 2011/0054621 A1 * | 3/2011 | Lim ............................. 623/17.16 |
| 2012/0185045 A1 * | 7/2012 | Morris et al. ............... 623/17.11 |
| 2012/0203344 A1 | 8/2012 | Trudeau |
| 2012/0310287 A1 | 12/2012 | Bao et al. |

FOREIGN PATENT DOCUMENTS

| | | |
|---|---|---|
| CA | 2548780 | 7/2005 |
| CN | 1697633 | 11/2005 |
| DE | 9000094 U1 | 1/1991 |
| DE | 29911422 U1 | 8/1999 |
| DE | 10130825 | 3/2002 |
| EP | 0179695 | 4/1986 |
| EP | 0346129 A1 | 12/1989 |
| EP | 0773008 A1 | 5/1997 |
| EP | 0919209 A1 | 6/1999 |
| EP | 1104665 A1 | 6/2001 |
| EP | 1205160 | 5/2002 |
| FR | 2372622 | 6/1978 |
| FR | 2723841 | 3/1996 |
| FR | 2787014 | 6/2000 |

(56) References Cited

FOREIGN PATENT DOCUMENTS

| | | |
|---|---|---|
| FR | 2797179 | 2/2001 |
| FR | 2799116 | 4/2001 |
| FR | 2805985 | 9/2001 |
| FR | 2824261 | 11/2002 |
| JP | 63300758 A2 | 12/1988 |
| JP | 1308557 A2 | 12/1989 |
| JP | 01142293 | 4/1990 |
| JP | 02111358 | 4/1990 |
| JP | 2215461 A2 | 8/1990 |
| JP | 2224659 A2 | 9/1990 |
| JP | 2224660 A2 | 9/1990 |
| JP | 04303444 A | 10/1992 |
| JP | 05277141 A | 10/1993 |
| JP | 06285099 | 10/1994 |
| JP | 08098850 A | 4/1996 |
| JP | 08098851 A2 | 4/1996 |
| JP | 11009618 A | 1/1999 |
| JP | 11137585 A | 5/1999 |
| JP | 2008284348 | 11/2008 |
| WO | 9011740 | 10/1990 |
| WO | 9105521 | 5/1991 |
| WO | 9116867 | 11/1991 |
| WO | 9316664 | 9/1993 |
| WO | 9500082 | 5/1995 |
| WO | 9601598 | 1/1996 |
| WO | 9611642 | 4/1996 |
| WO | 9627339 | 9/1996 |
| WO | 9805274 | 2/1998 |
| WO | 9819617 | 5/1998 |
| WO | 9855053 | 12/1998 |
| WO | 9911203 | 3/1999 |
| WO | 9922675 | 5/1999 |
| WO | 9930651 | 6/1999 |
| WO | 0013619 | 3/2000 |
| WO | 0042953 | 7/2000 |
| WO | 0059412 | 10/2000 |
| WO | 0115638 | 3/2001 |
| WO | 0132100 | 5/2001 |
| WO | 0168003 | 9/2001 |
| WO | 02087480 | 11/2002 |
| WO | 03035129 | 5/2003 |
| WO | 03099172 | 12/2003 |
| WO | 2005009298 | 2/2005 |
| WO | 2005041818 | 5/2005 |
| WO | 2005051240 | 6/2005 |
| WO | 2006016384 | 2/2006 |
| WO | 2006061114 | 6/2006 |

OTHER PUBLICATIONS

Depuy Spine, Inc., Charite Artificial Disc Centreline TDR Instrumentation Surgical Technique, Dec. 2004, 20 pp.
Depuy Spine, Inc., Charite Artificial Disc Product Catalog, Dec. 2004, 16 pp.
European Patent Office, Supplemental EPO Search Report for Application No. 03738960.8, Feb. 20, 2008, 6 pp.
Feder, B., "When FDA Says Yes, but Insurers Say No," The New York Times, Jul. 6, 2005, 2 pp.
Zdeblick, T., et al., "Cervical Interbody Fusion Cages", Spine, vol. 23, No. 7, 1998, 11 pp.
State Intellectual Property Office, First Notification of Office Action for Application No. 200780040650.7, Dec. 15, 2010, 9 pp.
European Patent Office, Supplemental EPO Search Report for Application No. EP07842616, Mar. 20, 2012, 7 pp.
European Patent Office, Supplemental EPO Search Report for Application No. EP04706064, Mar. 22, 2012, 8 pp.

* cited by examiner

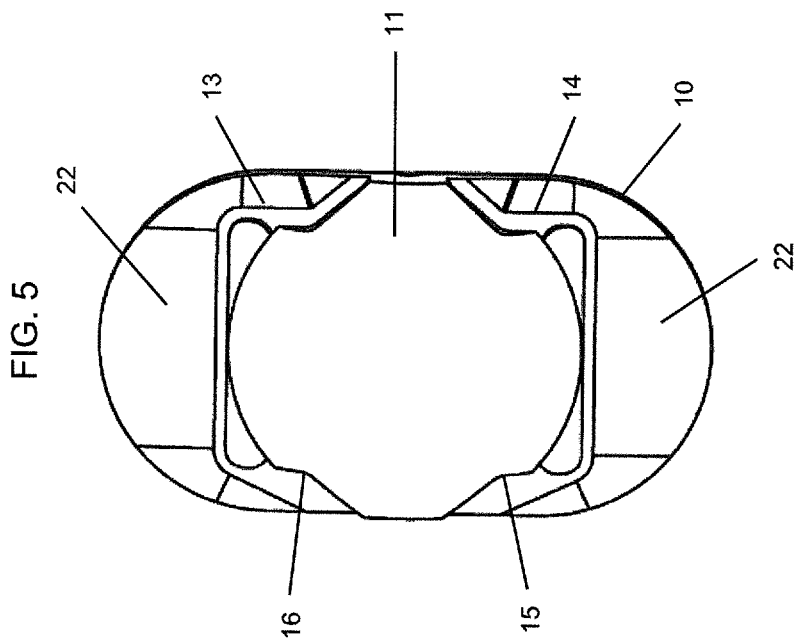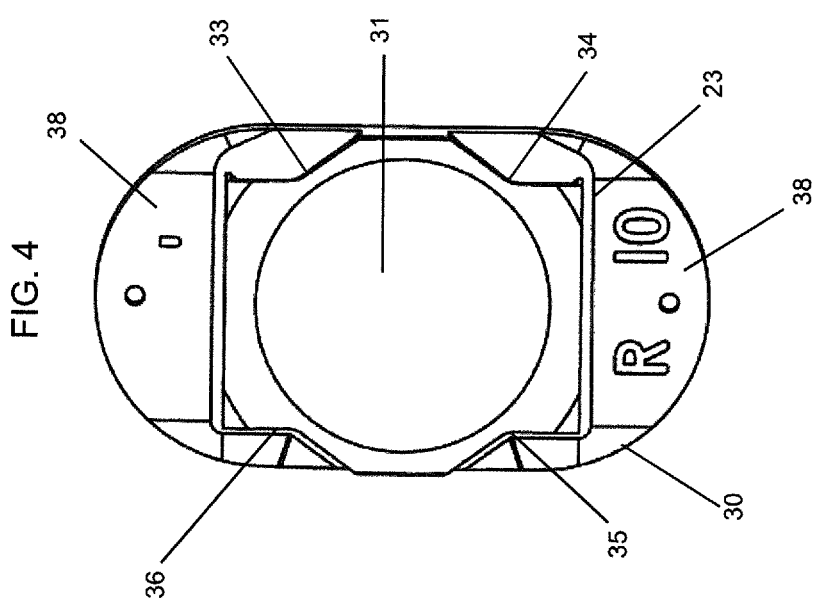

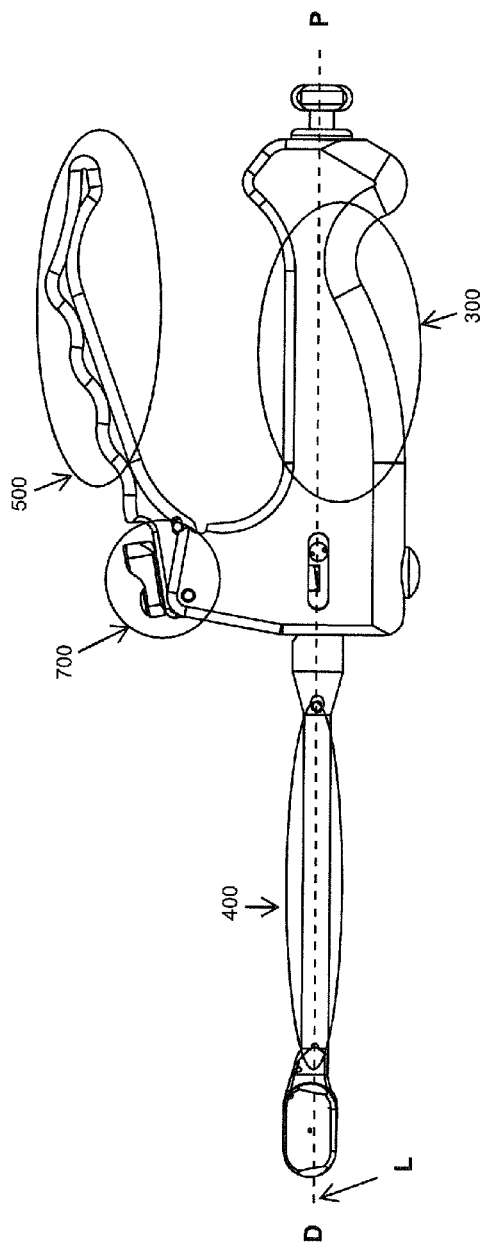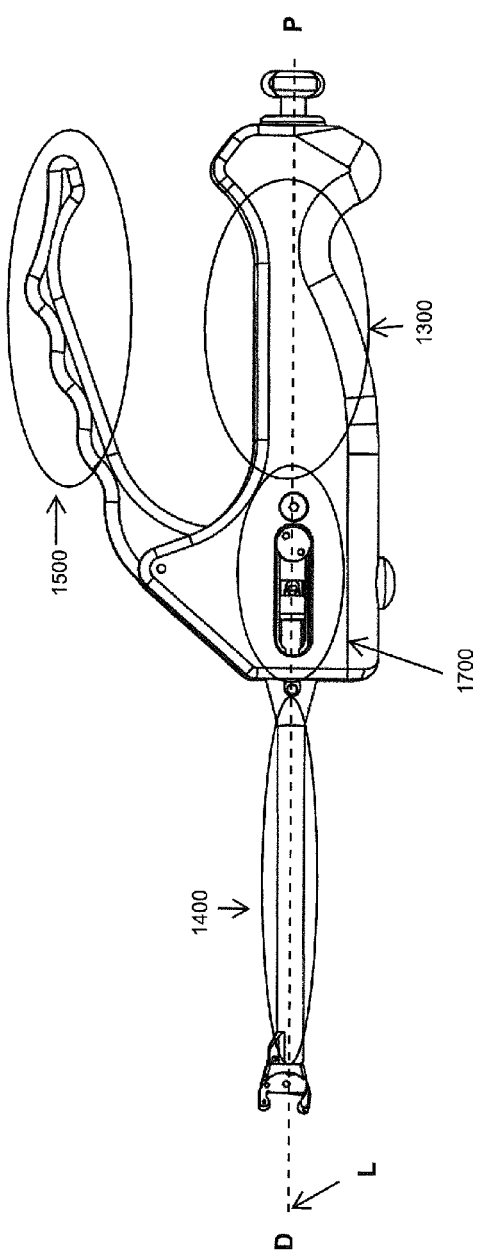
FIG. 13a
FIG. 13b

FIG. 19a
FIG. 19b
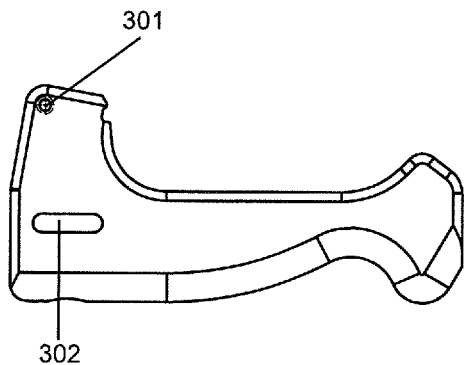
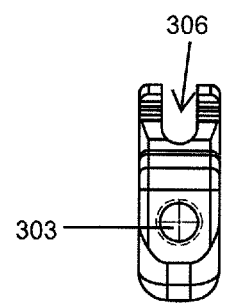
FIG. 19c
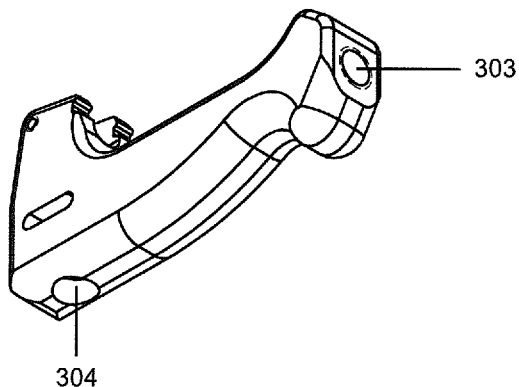
FIG. 19d
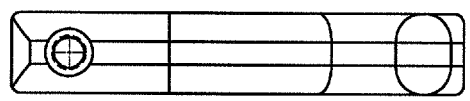

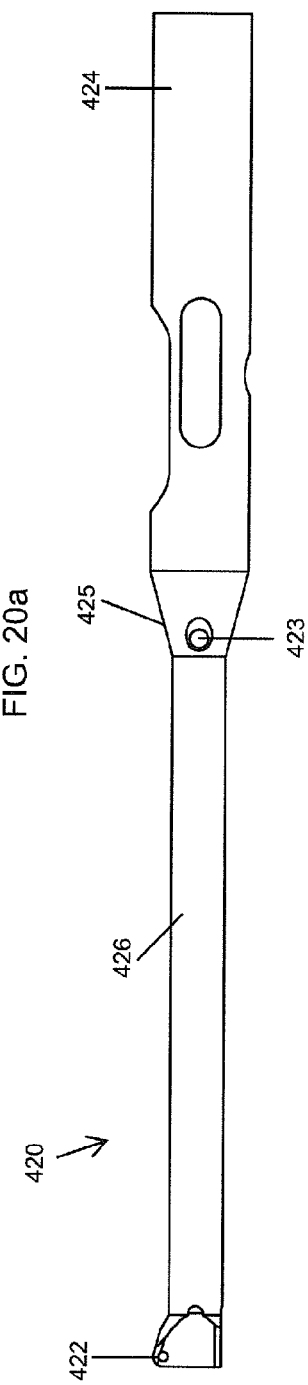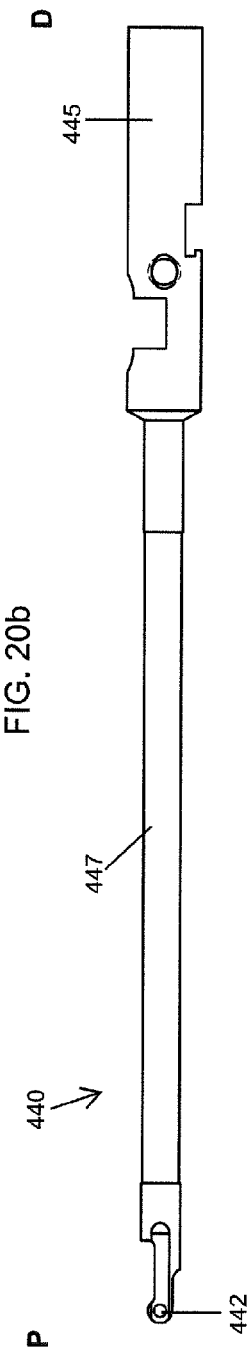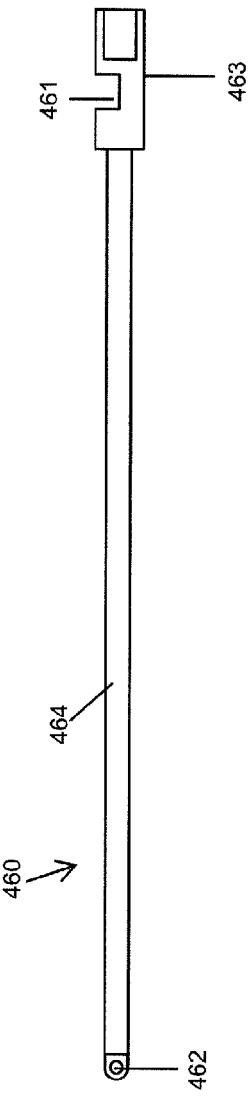

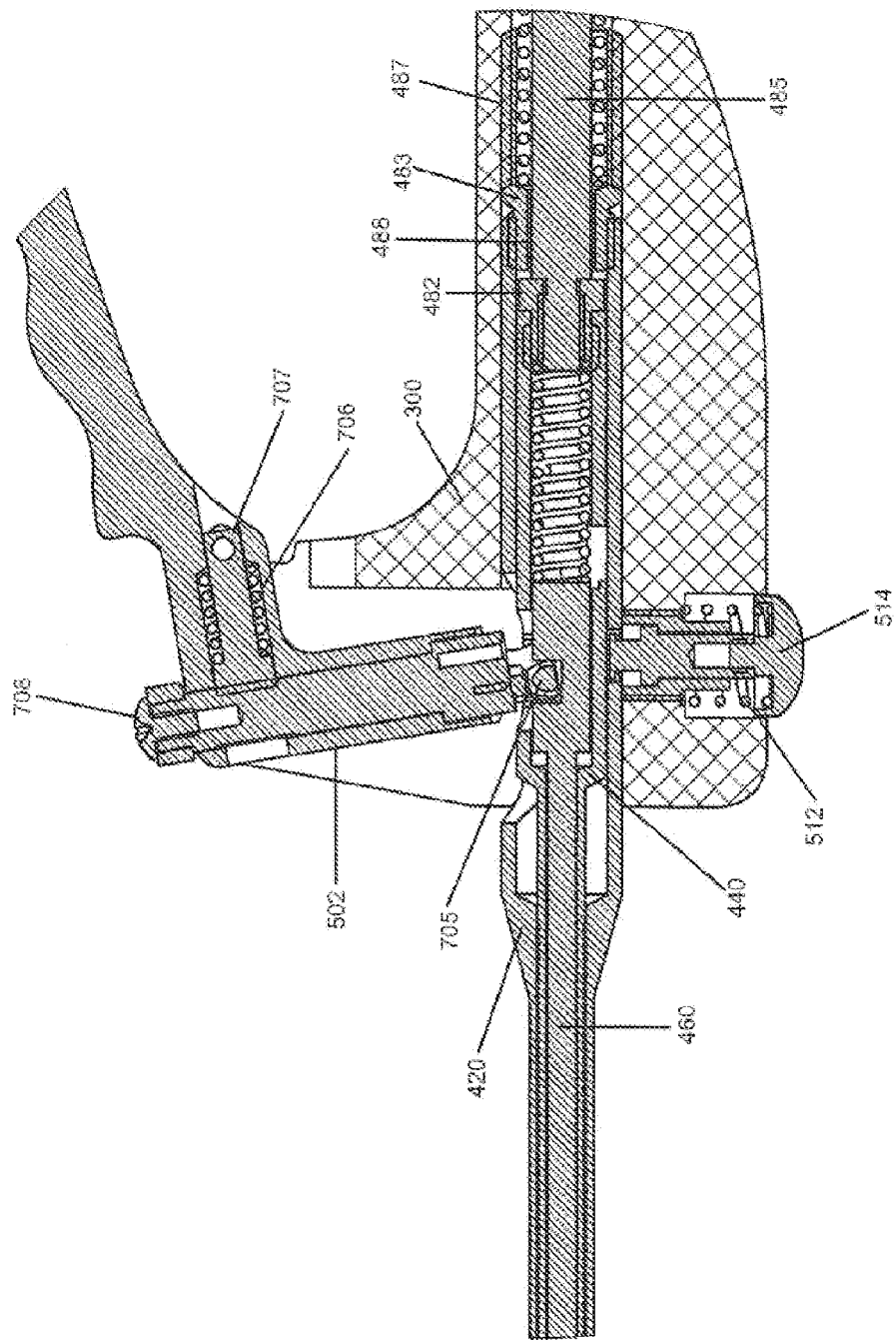

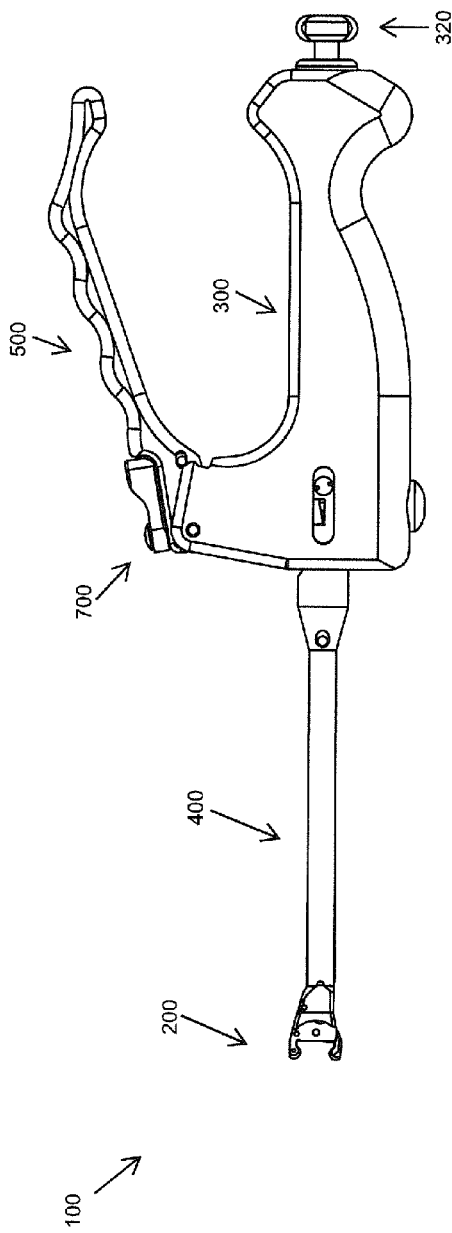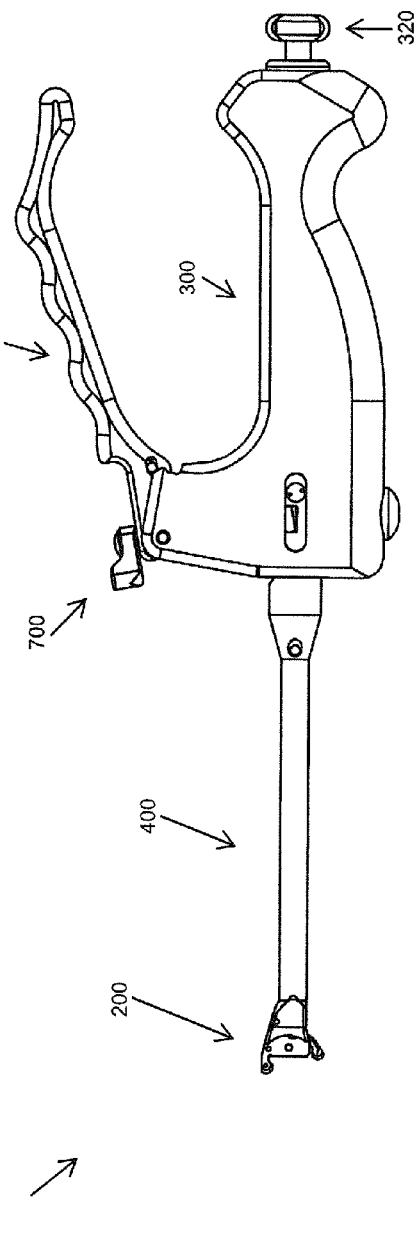

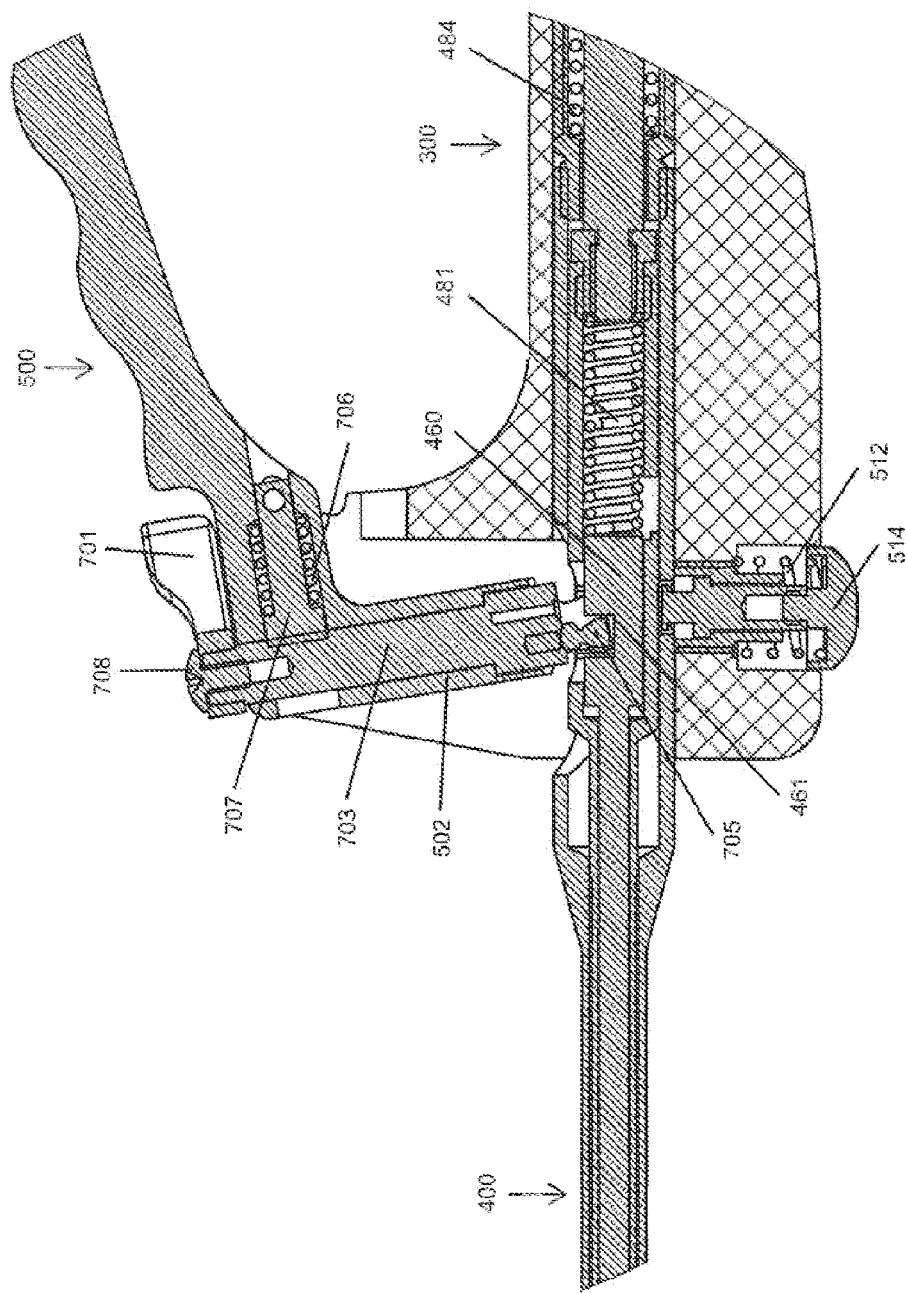

Fig. 33a
Fig. 33b
1300
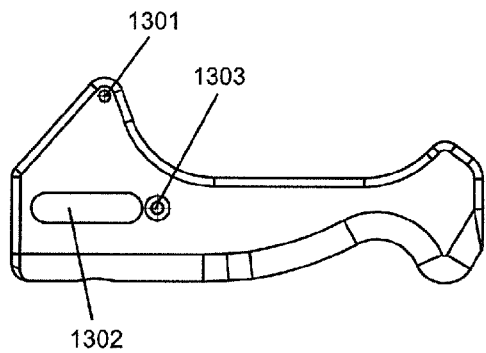
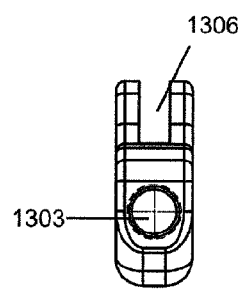
Fig. 33c
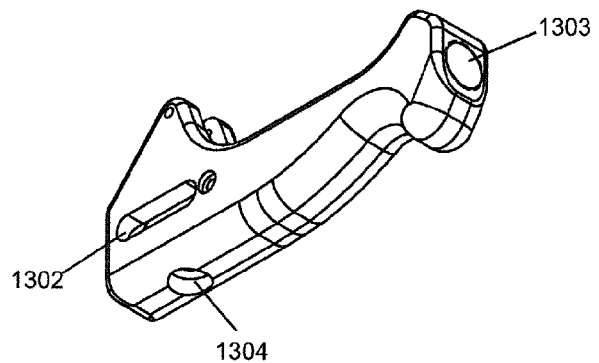
Fig. 33d
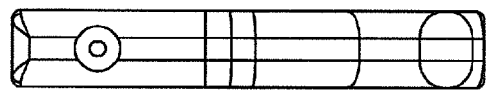

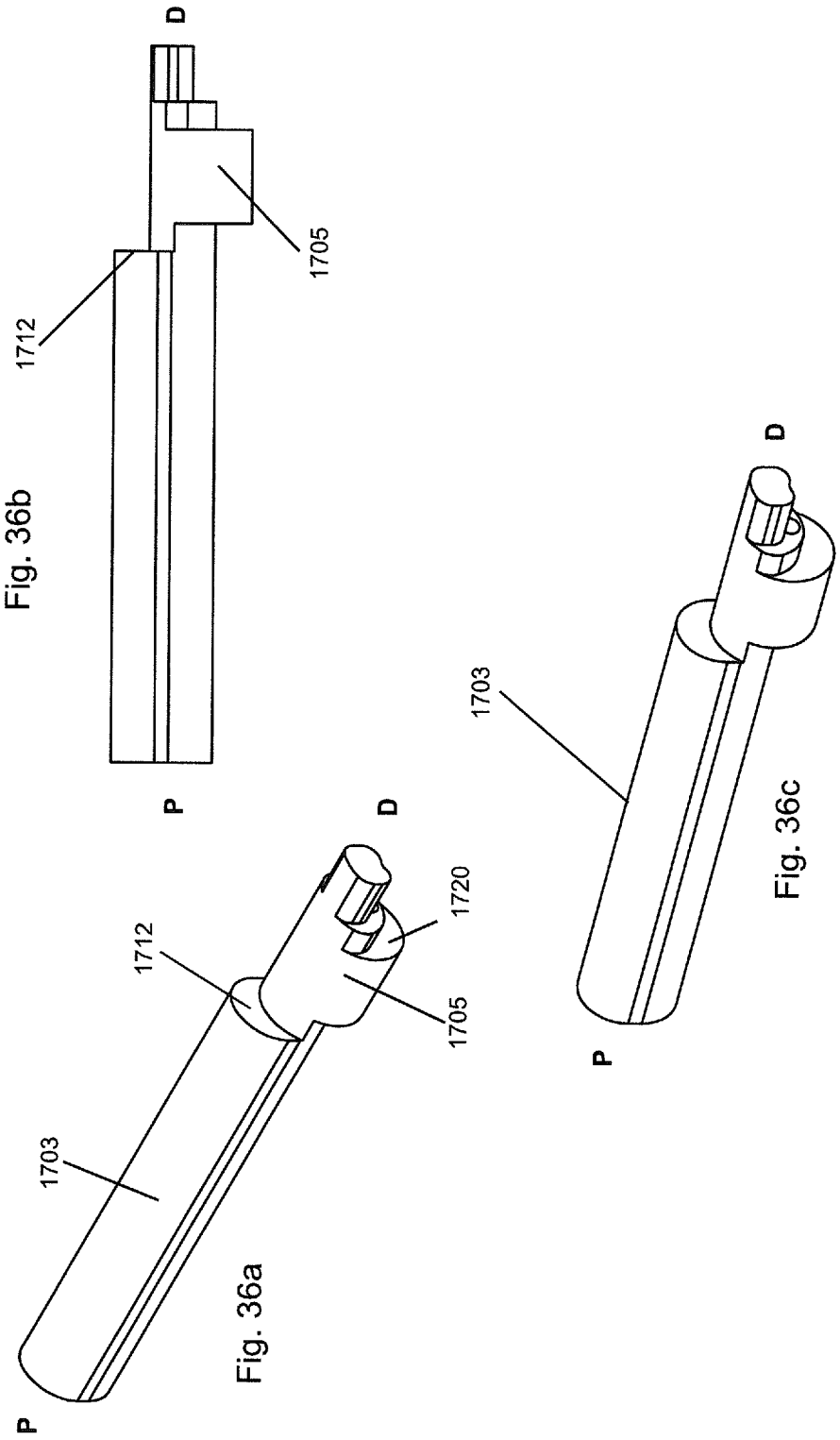

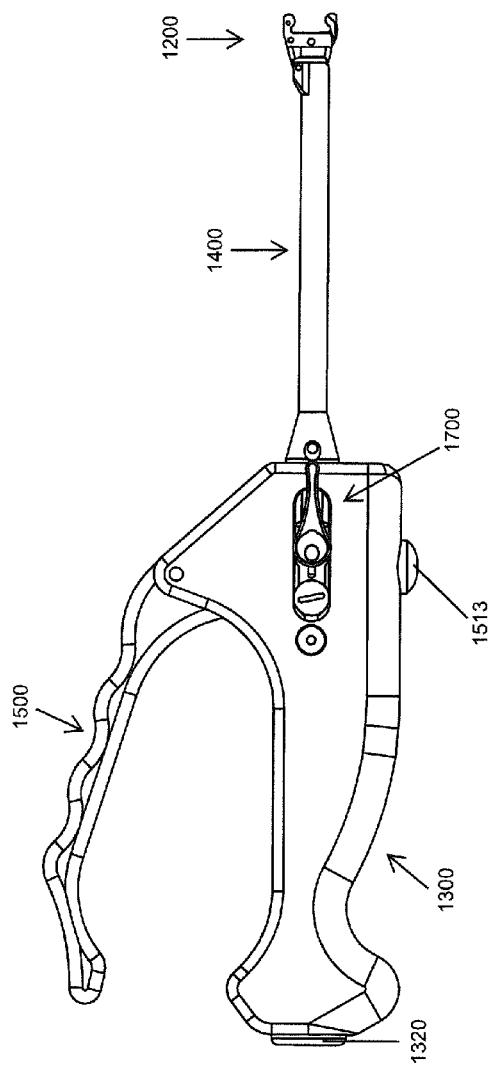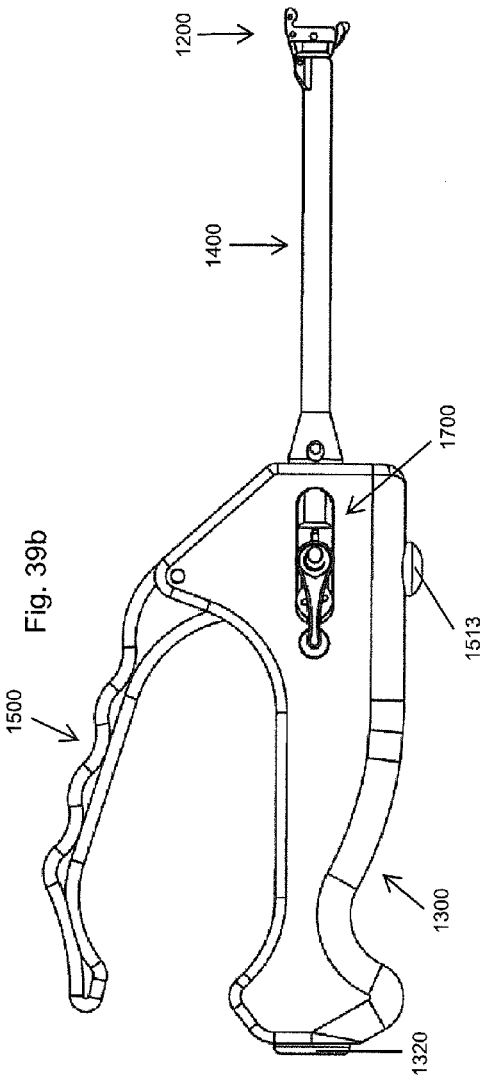

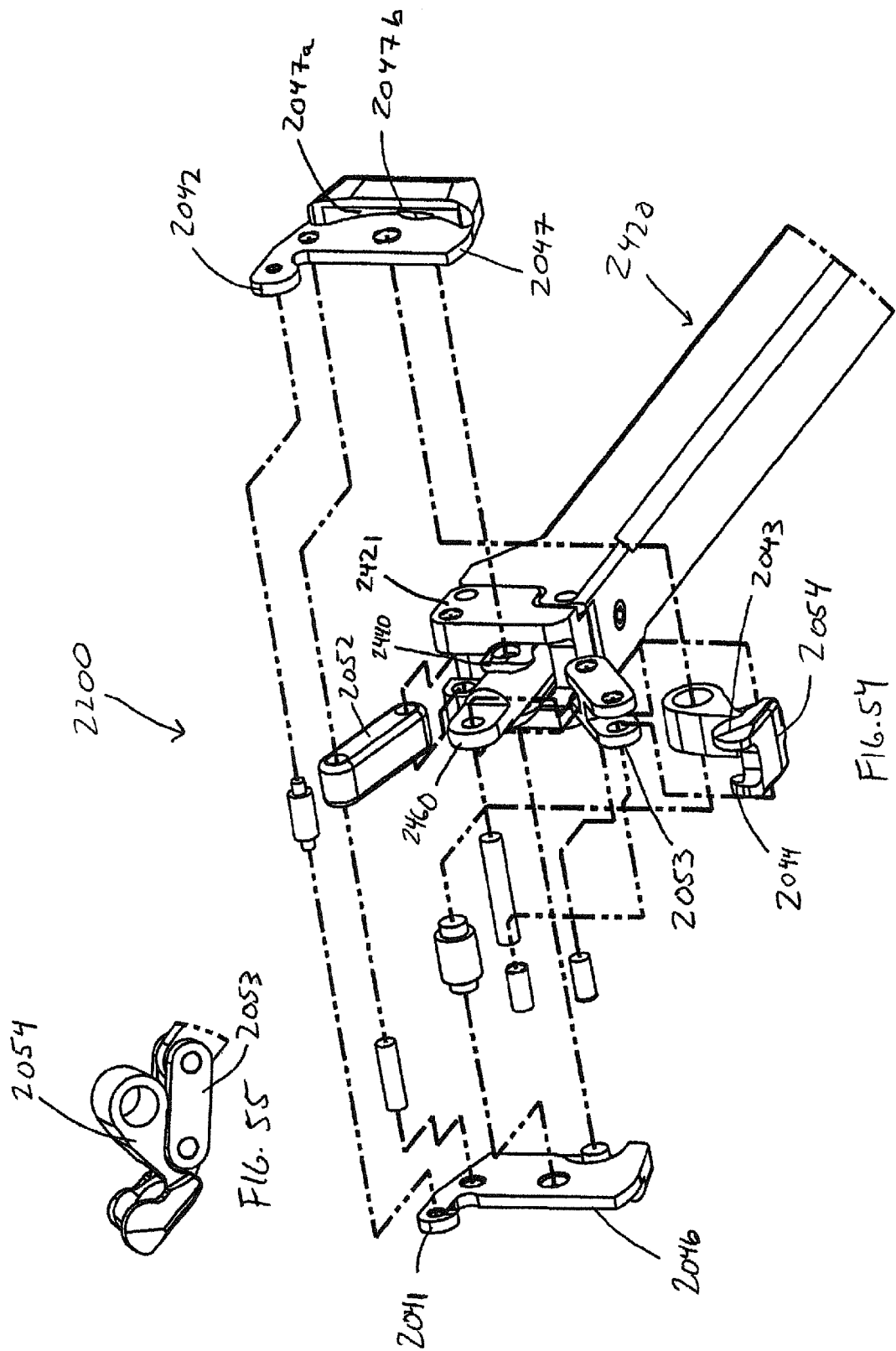

SYSTEMS AND METHODS FOR INSERTING A SPINAL DEVICE

CROSS-REFERENCE TO RELATED APPLICATION

This application claims the benefit of U.S. Provisional Application No. 61/580,055, filed Dec. 23, 2011, which is incorporated herein by reference in its entirety.

BACKGROUND

In the field of orthopedic surgery, in particular minimally invasive orthopedic surgery, the physician often works through a very small incision, a small cannulated tube or a retractor. Since the working space for the surgeon is a small confined channel, specialized instruments are necessary to safely navigate the distance from outside the skin of the patient to adjacent the surgical site within the body of the patient. These specialized instruments, depending on the type of surgery, may include custom rongeurs, rasps, curettes and spinal device insertion instruments.

When performing an orthopedic joint replacement surgery, in particular intervertebral disc or nucleus replacement surgery, it is often difficult to properly and confidently position an implant in the position desired by the surgeon. It is desirable to utilize an implant insertion instrument that firmly holds the implant, while allowing the surgeon to release the instrument to safely perform fluoroscopy. It is also desirable, after fluoroscopy, to be able to redirect, manipulate and release the implant percutaneously once the desired position of the implant has been achieved.

When performing an intervertebral disc or a nucleus replacement surgery, the surgeon may have a preference for, or patient anatomy may dictate, the origin and direction of entry into the body of the patient including anterior, lateral, or posterior approaches. Each method of entry presents the surgeon with specific challenges that are typically met with instruments corresponding to the decided method of entry. It would be desirable to have a spinal implant insertion instrument that would meet the specific surgeon challenges of anterior, lateral and posterior methods of entry.

Manipulating and steering a multiple piece implant presents additional challenges. It is desirable to be able to both steer a multiple piece implant, such as a two-piece motion preserving nucleus replacement device (NRD), while allowing for independent movement between the various pieces for promoting ease of insertion of the device. Thus, an implant and corresponding insertion instrument capable of reliably, safely, and simply gripping, steering, and releasing an implant, while allowing for the implant to be configured in a compact orientation is desirable.

Another problem in the art is the cleanability of surgical tools. In some circumstances, blood, tissue, or other matter may find its way into difficult-to-access portions of the instrument. While the tool may be sterilized using an autoclave, blood and other foreign matter may still remain within the instrument. Accordingly, it is desirable that an insertion instrument be configured to be cleanable, such as by using hand methods to clean, brush, wash or scrub any foreign matter from the interior of the instrument.

SUMMARY OF THE INVENTION

Implanting a spinal device, such as a spinal implant, from a posterior or posterolateral approach presents the surgeon with additional challenges and concerns, as this method requires the implant to be negotiated from either side of the spinal canal to within the intervertebral disc space. An insertion tool is described herein which can hold an articulating, multi-component artificial disc device firmly while permitting the implant to form a wedge shape for ease of insertion into the disc space, and be manipulated percutaneously within the disc space from a first posterior-anterior orientation to a second orientation substantially transverse to the first orientation to minimize the invasiveness of the insertion procedure.

Several embodiments of a system for inserting a motion preserving implant are described herein. More specifically, various embodiments of insertion instruments are described for manipulating and inserting an articulating spinal nucleus device. These embodiments are particularly adapted to meet the challenges of minimally invasive anterior, lateral, and especially posterior approaches to the spine.

A motion preserving implant according to the present invention may include upper and lower shell members having dome and arcuate recess portions for providing an articulating interface therebetween. Each shell member may include structure for interfacing with an insertion tool. Preferably, the tool engaging structure takes the form of opposing recessed portions disposed on opposite sides of the body of the shell members such that a portion of the body of each shell member may be gripped by the insertion instrument at the recessed portions between gripping portions of the insertion instrument in a clamping type configuration. In one form, the dome portion is located on the lower shell member and the tool engaging structure takes the form of a plurality of undercuts or recessed portions in the dome portion on opposite sides of the dome. The arcuate recessed portion similarly includes tool engaging structure in the form of a plurality of undercuts or recessed portions for engaging with a gripping portion of the tool.

In one form, a two-piece intervertebral implant for being inserted into an intervertebral space between adjacent upper and lower vertebrae includes upper and lower bearing member bodies each having an outer bearing surface and an inner facing surface. A dome portion of one of the bearing members extends away from the inner facing surface of one of the bearing members and includes a convex arcuate bearing surface. A raised portion of the other of the bearing members extends away from the inner facing surface thereof and includes a concave arcuate bearing surface portion configured for sliding engagement with the convex arcuate bearing surface of the dome portion to provide an articulation interface between the upper and lower bearing members. A plurality of recessed instrument engagement portions disposed on each of the dome and raised portions of the bearing members are provided for being gripped by an insertion instrument between the inner facing surfaces of the upper and lower bearing members.

In another form, a two-piece articulating implant includes an upper bearing member having an outer bearing surface and an inner facing surface, a lower bearing member having an outer bearing surface and an inner facing surface, a dome portion of one of the bearing members that extends away from the inner facing surface of one of the bearing members including a convex arcuate bearing surface, a concave arcuate bearing surface portion of the other bearing member configured for sliding engagement with the convex arcuate bearing surface of the dome portion to provide an articulation interface between the upper and lower bearing members, and a plurality of opposed recessed cutouts disposed in the dome portion for receiving gripping portions of an insertion instrument.

The tool engaging portions may be similarly shaped or have different configurations. In one form the tool engaging portions on the upper shell member may have an enlarged dimension, such as an enlarged height to allow the upper shell to move with respect to the insertion tool and the lower shell member, while still being grasped by the tool. Preferably, the tool and the tool engaging portions of the implant are configured to allow the upper shell member to be shifted with the leading end of the implant shifted towards the leading end of the lower shell member to decrease the overall height of the implant at the insertion end. Consequently, the trailing end of the upper shell is shifted away from the trailing end of the lower shell such that the height of the implant at the trailing end is increased. This configuration looks akin to a "wedge." As the implant is inserted into an intervertebral space, the trailing end of the implant will tend to abut the adjacent tissue or bone and cause the upper shell to return to a neutral position with the ends of the upper and lower shells approximately evenly spaced apart such that the implant has a relatively uniform height from one end to another. The implant and the tool may be configured such that the upper shell may only form a wedge with one end being the shorter, leading end. The permitted movement of the upper shell may be limited to a desired range, such as between a neutral position and a wedge configuration. The lower shell and tool are preferably configured such that the lower shell may not shift with respect to the tool, but alternatively may be configured for limited movement as well, or alternatively, the upper shell may be configured to be held without shifting with respect to the tool and the lower shell may be configured to shift with respect to the tool and the upper shell in a like manner.

An insertion tool according to another aspect of the present invention may be configured to grip or release an implant at an insertion configuration, such as with the longitudinal axis of the implant substantially aligned with the longitudinal axis of the tool; at a fully rotated configuration, with the longitudinal axis of the implant transverse to the longitudinal axis of the tool; or at any intermediate position between the insertion configuration and the fully rotated configuration. This allows the user to release the implant at any desired position. The insertion tool may also be configured to automatically return to an insertion configuration from a rotated configuration. The tool may also be configured to return from an implant releasing orientation to an implant gripping orientation when the tool returns to the insertion configuration from a rotated configuration. Such features can reduce the profile of the tool at the distal end and help prevent unnecessary trauma to the implantation site, such as an opening created in an annulus for replacing the nucleus of a spinal disc.

In one form, a tool for inserting a two-piece articulating implant may include a pivotable head portion including a pair of opposing clamping jaws, wherein at least one clamping jaw is stationary and one clamping jaw is moveable between clamped and unclamped configurations via a single actuator. Each jaw may comprise a pair of gripping portions or fingers for engaging with the implant. Preferably, one gripping portion of each jaw engages with one piece of the implant, and the other gripping portion of each jaw engages with the other piece of the implant, such that both jaw members engage both pieces of the implant. The stationary clamping jaw preferably includes a pair of gripping fingers and the moveable jaw preferably includes an opposing pair of gripping fingers, such that when the moveable jaw member is pivoted, the gripping fingers of the moveable jaw pivot relative to the stationary gripping fingers. An outer shaft having a longitudinal axis is pivotally connected to the pivotable head portion and a shiftable intermediate interior shaft is disposed within the outer shaft and is shiftable with respect thereto for causing the head portion to pivot with respect to the outer shaft. A shiftable central release shaft is disposed within the middle interior shaft and is shiftable with respect thereto for pivoting the moveable jaw to alternatively grip the implant pieces between the moveable jaw and the stationary jaw and release the implant by pivoting the moveable jaw away from the stationary jaw.

An insertion tool according to the present invention may be configured to have improved cleanability. In one form, an insertion tool may have a split shaft configuration such that one or more shafts are releasably connected to one another or to other tool components to allow the components to be easily partially or completely disassembled into individual components or subassemblies to be individually cleaned. For example, one or more shaft members may be releasably connected to a handle or actuator of the tool. In another form, one or more shaft members may be configured to splay apart from one another at one end such that each shaft member may be more easily cleaned. In one embodiment, the shaft members are operably connected near the distal end of the tool such that the proximal ends of the shafts may be distracted apart from one another to allow for better accessibility for cleaning.

BRIEF DESCRIPTION OF THE DRAWINGS

FIG. 4 is a plan view of an upper shell member of the NRD of FIG. 1;

FIG. 5 is a plan view of a lower shell member of the NRD of FIG. 1;

FIG. 13a is an elevation view of an insertion instrument according to the present invention holding an NRD at its distal end;

FIG. 13b is an elevation view of an alternate insertion instrument according to the present invention;

FIG. 18 is an exploded view of the insertion instrument of FIG. 13a;

FIGS. 19a-19d are various views of a handle portion of the insertion instrument according to FIG. 13a;

FIGS. 20a-20c are elevation views of shaft members of the insertion instrument according to FIG. 13a;

FIG. 21 is an exploded view of an actuator assembly of the insertion instrument according to FIG. 13a;

FIGS. 22a-22d are various views of a release lever shaft of the insertion instrument according to FIG. 13a;

FIGS. 23-31 are various views of the instrument of FIG. 13a demonstrating the operation of the instrument;

FIGS. 33a-33d are various views of a handle portion of the insertion instrument of FIG. 32;

FIGS. 36a-36c are various views of a release lever shaft of the insertion instrument of FIG. 32;

FIGS. 37-46 are various views of the instrument of FIG. 32 demonstrating the operation of the instrument;

FIGS. 54-58 are various exploded views of portions of the instrument of FIG. 47.

DESCRIPTION OF PREFERRED EMBODIMENTS

Figure 1:
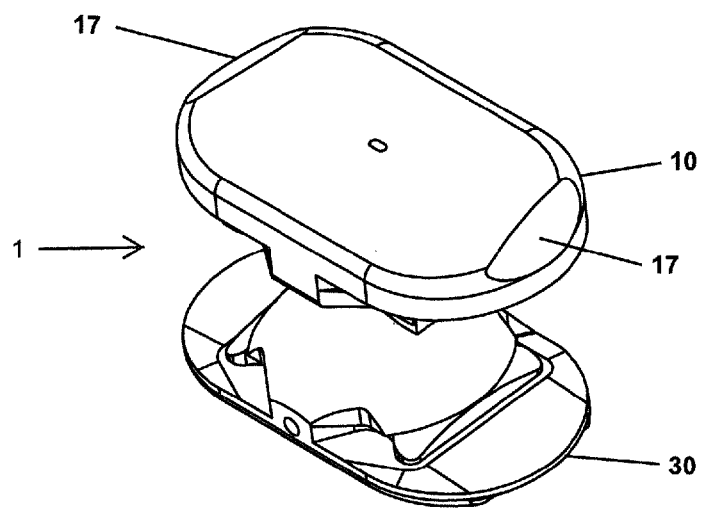
FIG. 1 is a exploded perspective view of an NRD according to the present invention.

One embodiment of the invention includes an instrument for positioning an intervertebral implant or spacer between adjacent vertebral members. FIG. 12B illustrates an intervertebral implant or spacer 1 movably connected to an implant insertion instrument 100. Spacer 1 is configured to be positioned between adjacent vertebrae and is selectively adjustable between an orientation wherein the longitudinal axis 1L of spacer 1 is generally aligned with longitudinal axis L of instrument 100 to an orientation wherein axis 1L is generally perpendicular (i.e., within 30 degrees) to instrument axis L, and any position therebetween. Instrument 100 allows the surgeon to manipulate, and release the implant at any desired orientation within the range of the instrument.

FIGS. 1-7 illustrate one embodiment of an intervertebral spacer, in particular a two-piece articulating spinal nucleus replacement device (NRD) according to the present invention. Additional details regarding additional aspects of the NRD according to the present invention may be found in U.S. Pat. No. 8,241,360 and U.S. Published Patent Application 2008-0109081, both of which are incorporated herein by reference. The NRD 1 comprises a top shell 10 and a bottom shell 30. Top shell 10 has a raised portion 23 which includes an inner concave articulating surface 11 with a radius of curvature, and bottom shell 30 includes a dome portion 40 with an inner convex articulating surface 31 with a radius of curvature. It is preferable that the radii of curvature of the articulating surfaces match, but other configurations may be used as is known in the art. Inner articulating surfaces of shells 10, 30 once implanted, interact to mimic the natural motion of the spine. Both shells comprise bodies including outer vertebral engaging surfaces 12, 32 configured to slidingly engage the surface of an endplate of a vertebral body while allowing the implant to translate relative thereto. It should be noted the arrangement of top and bottom shells 10, 30 could be reversed such that the top or superior shell 10 could be placed inferior to shell 30. Opposing ends of implant bodies 10, 30 comprise beveled entry surfaces 17, 37 configured to reduce insertion forces upon entry into the nuclear space. Entry surfaces 17, 37 may take the form of radiused or tapered ends. The tapered ends ease the introduction of the implant into the nuclear space. The implant insertion instruments 100, 1100, 2100 may also be configured to hold the implant in a wedge configuration as will be described below to help further reduce the insertion force upon entry of the implant into the nuclear space.

Both top and bottom shells 10, 30 have one or more instrument engaging portions. The lower shell 30 comprises instrument engaging portions 33-36, while upper shell 10 comprises instrument engaging portions 13-16. The location, shape and configuration of engaging portions 13-16 of top shell 10 are substantially equivalent. Engagement portions 33-36 of shell 30 are also substantially equivalent, but differ from that of portions 13-16. While engagement portions of the individual shells may be equivalent, it should be understood that other arrangements may be contemplated. The engaging portions of both shells are generally located between the inner facing surfaces 22, 38 of the upper and lower shells 10, 30, and are formed recessed within bearing surfaces 31, 11 located on lateral sides generally opposite one another along the outer proximity of the bearing surfaces. The location and configuration of recesses 33-36, 13-16 do not interrupt or protrude beyond the contour of the bearing surfaces and therefore do not interfere with the polyaxial articulation of the top and bottom shells 10, 30. Accordingly, the bearing surfaces 11, 31 provide consistent smooth surface contact between the top and bottom shells which helps reduce wear debris. The configuration of clamping fingers 41-44 of one embodiment of the insertion tool residing within the recesses of the bearing surfaces allows for the exterior surfaces of the clamping fingers to remain within side walls 20, 21 of implant 1, providing a preferred arrangement for minimally invasive insertion. In other words, when the clamping fingers 41-44 are operably engaged within the tool engaging recessed portions 13-16, 33-36, the outer surfaces of the fingers 41-44 will preferably not project beyond the side walls 20 and 21 of the implant 1. Engaging portions 13-16, 33-36 generally are in the form of an undercut that creates a shelf with a pocket or recess comprising top portions 10T, 30T, and bottom portions 10B, 30B having heights 10H, 30H therebetween. The top and bottom portions of the implant engaging recesses are designed to cooperate with the superior and inferior surfaces of implant clamping fingers 41-44 for capturing and retaining the substantially flat implant clamping fingers of insertion instrument 100, 1100 therein.

Figure 8:
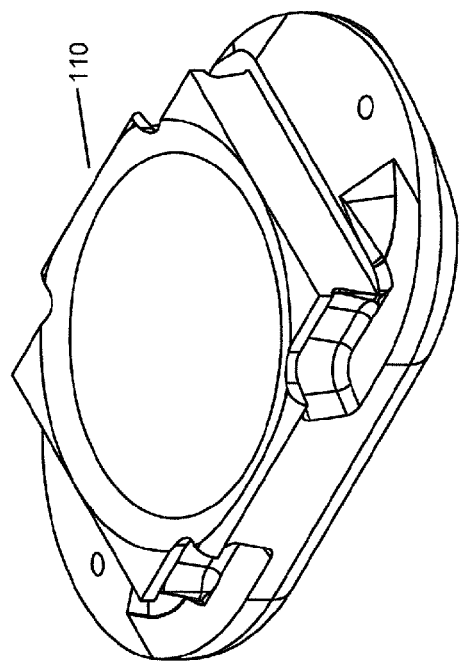
Figure 10:
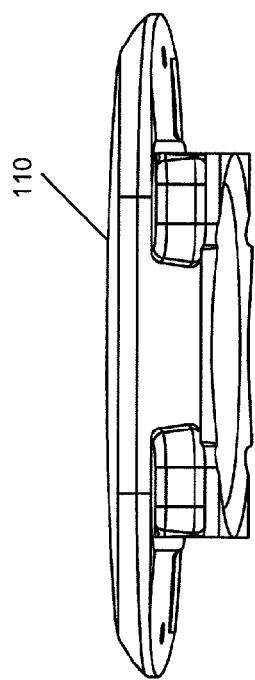

The instrument engagement portions of both shells 10, 30 of the present invention are similar with the exception of the relative height of the recesses. As best seen in FIG. 8, the recesses have an inner configuration to compliment that of implant clamping fingers 41-44; in the case of the present invention the inner recess surfaces have an arcuate configuration comprising a radius that is substantially equal to that of the radius of the inwardly facing surfaces of clamping fingers 41-44. Optionally, the geometries of the clamping fingers and engaging portions employed could be any of a variety of shapes.

Figure 2:
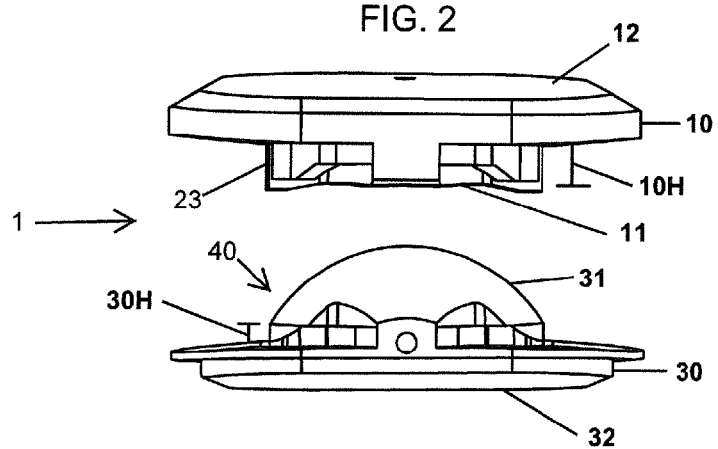
FIG. 2 is an exploded elevation view of the NRD of FIG. 1.

As shown in FIG. 2, the relative height 30H of recesses 33-36 formed in lower shell 30 are consistent throughout. Heights 10H, 30H are preferably slightly larger than the thickness of implant clamping fingers 41-44. Upper shell 10 comprises recesses 13-16 which include height 10H, 10H2 and transition zone 18. Height 10H is substantially equivalent to height 30H of lower shell 30. Transition zone 18, in the form of a radius or angle, makes the transition from height 10H to substantially greater height 10H2 disposed adjacent the outer perimeter of articulating surface 11. The arrangement of varying heights with a transition zone allows the surgeon to manually urge the distal ends of the top and bottom shells closer together causing clamping fingers 41, 44 to travel inferiorly within their corresponding recesses of the upper shell. The proximal end of upper shell 10 may be shifted and held at different locations within recesses 13-16, including a position wherein the inferior portion of clamping fingers 41, 44 contact the inferior portion of height 10H2 in recesses 13-16 near the outer proximity of bearing surface 12. The urging of the distal end of shell 10 inferiorly toward that of firmly held lower shell 30 results in upper shell 10 being held at an angle with respect to lower shell 30 with their respective longitudinal axes at an oblique angle to each other such that the distal ends of the upper and lower shells are positioned more closely together thus giving the implant a wedge configuration for promoting ease of insertion of the implant.

Figure 3:
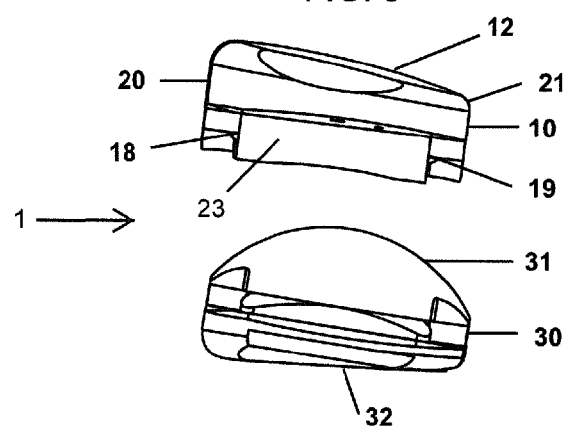
FIG. 3 is an exploded end view of the NRD of FIG. 1.
Figure 6:
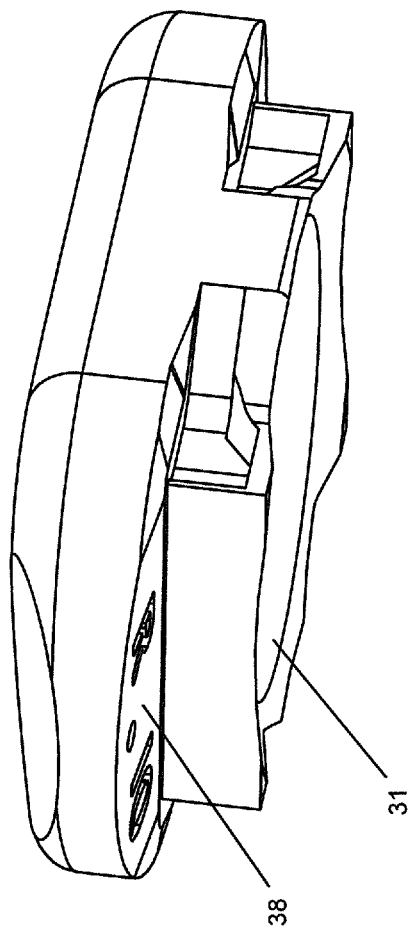
FIG. 6 is a perspective view of the upper shell member of the NRD of FIG. 1.
Figure 7:
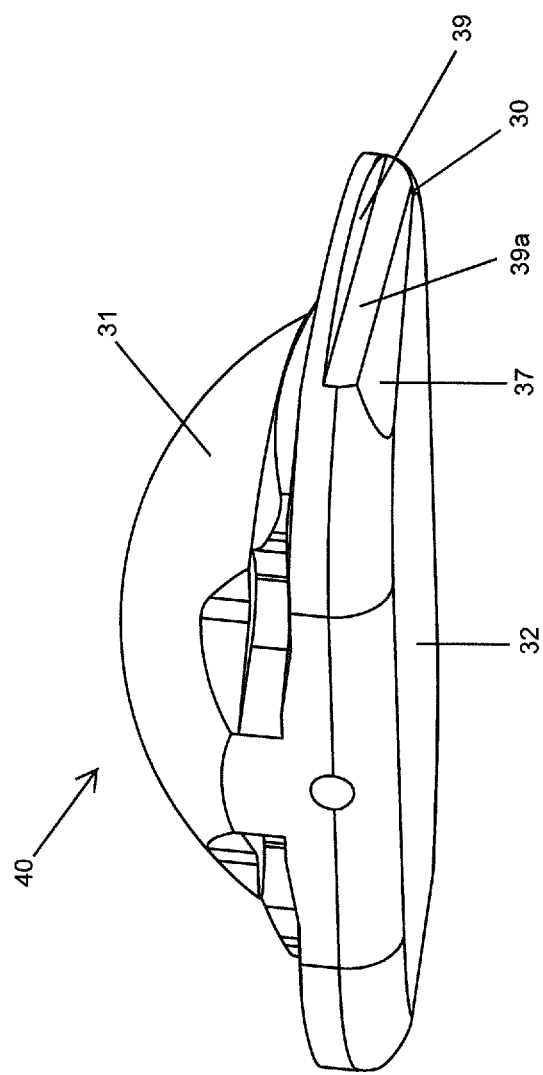
FIG. 7 is a perspective view of the lower shell member of the NRD of FIG. 1.
Figure 9:
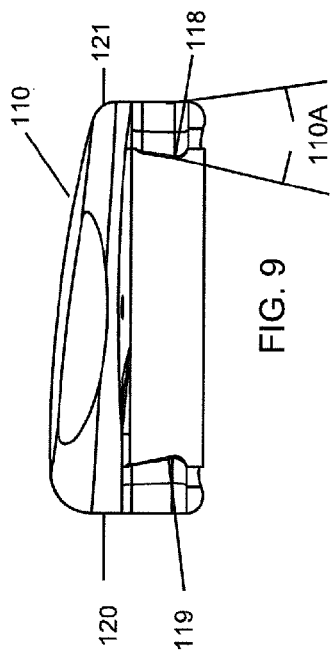
FIGS. 8-11 are various views of an upper shell member of an alternate embodiment of an NRD according to the present invention.
Figure 11:
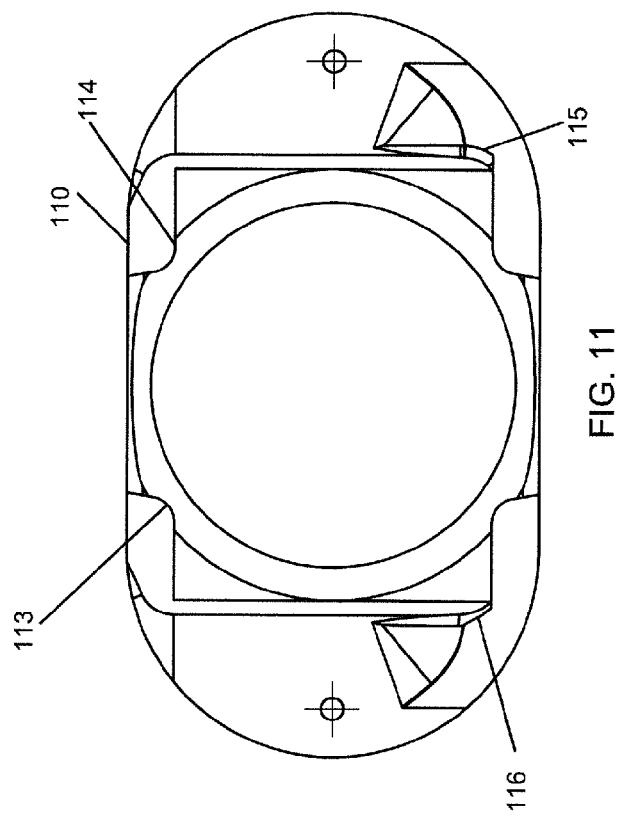

An alternative embodiment of a top shell 10A for NRD 1 is illustrated in FIGS. 8-11, bottom shell 30 remains unchanged. Shell 10A is substantially identical to top shell 10 with the exception of the angle of the walls within pockets 113-116, and the absence of varying heights. In FIG. 3, walls 18, 19 of top shell 10 are shown as being substantially parallel to side walls 20, 21. In the alternative embodiment 10A, the walls 18A, 19A of pockets 13A, 16A are at a slight angle 10B with respect to implant side walls 120 and 121. The superior portions of recess sidewalls 18A, 19A are in proximity to implant sidewalls 20A, 21A and angle slightly inward toward the inferior portions nearer the longitudinal axis. This slight angle encourages the clamping fingers of the insertion instrument to move inferiorly, urging the proximal end of top shell 10A superiorly relative to lower shell 30. The encouraged movement of the upper shell causes the distal end of shell 10A to move adjacent to lower shell 30, thus achieving, automatically, the same wedge configuration achieved manually with shells 10 and 30. Transition zone 18 and angled sidewalls 20A, 21A additionally allow shell 10, 10A while being firmly grasped during implant insertion, to assume any number of configurations as dictated by insertion angle and patient anatomy.

Figure 12:
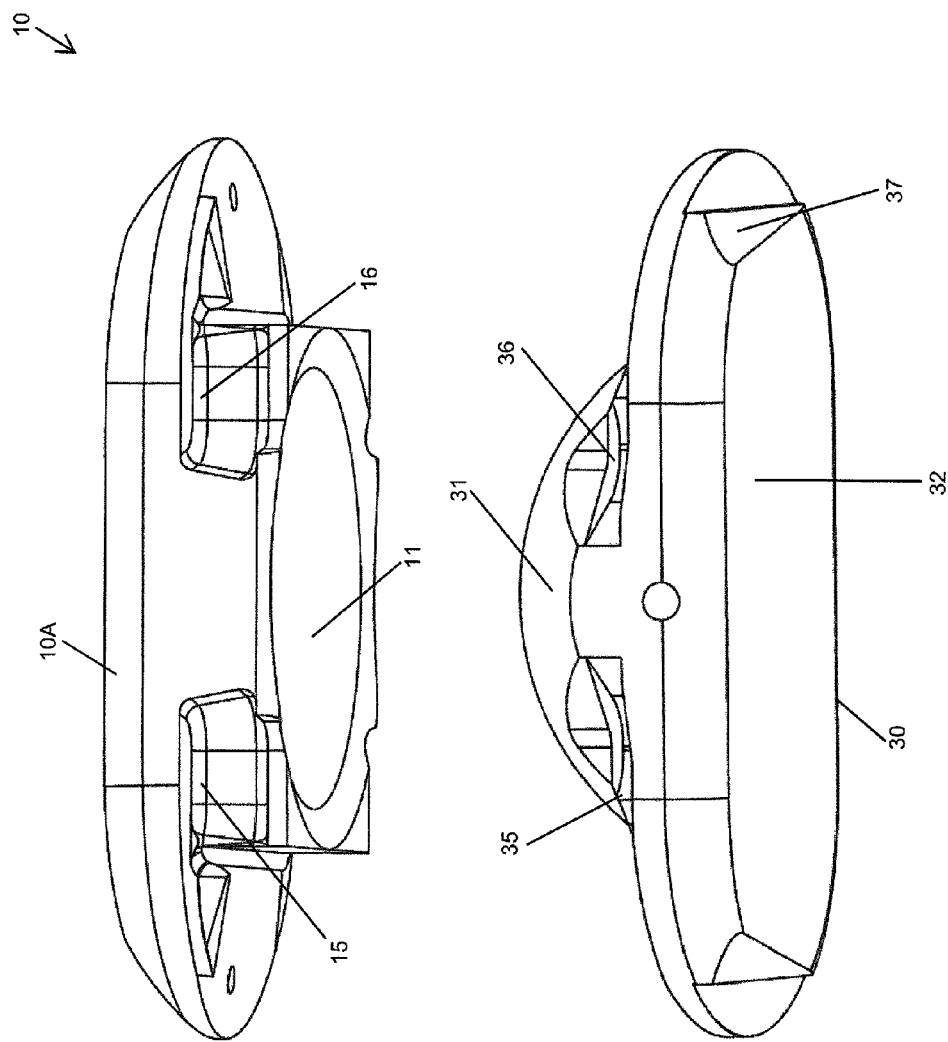
FIG. 12 is an exploded perspective view of the upper shell member of FIGS. 8-11 and a lower shell of the NRD of FIG. 1.
Figure 14A:
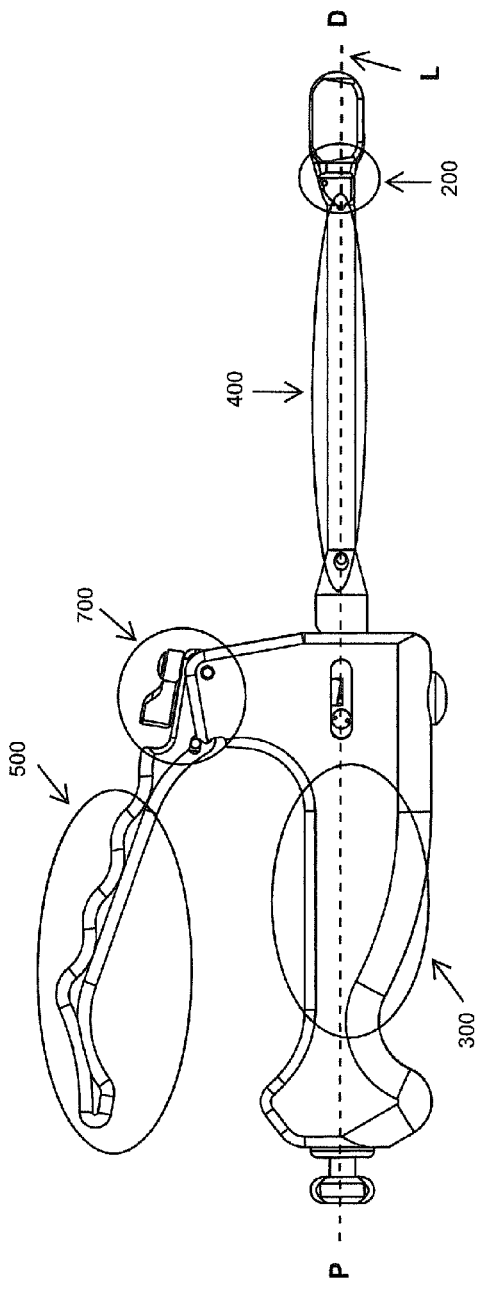
FIGS. 14a and 14b are elevation views from the opposite side of the respective insertion instruments according to FIGS. 13a and 13b.
Figure 14B:
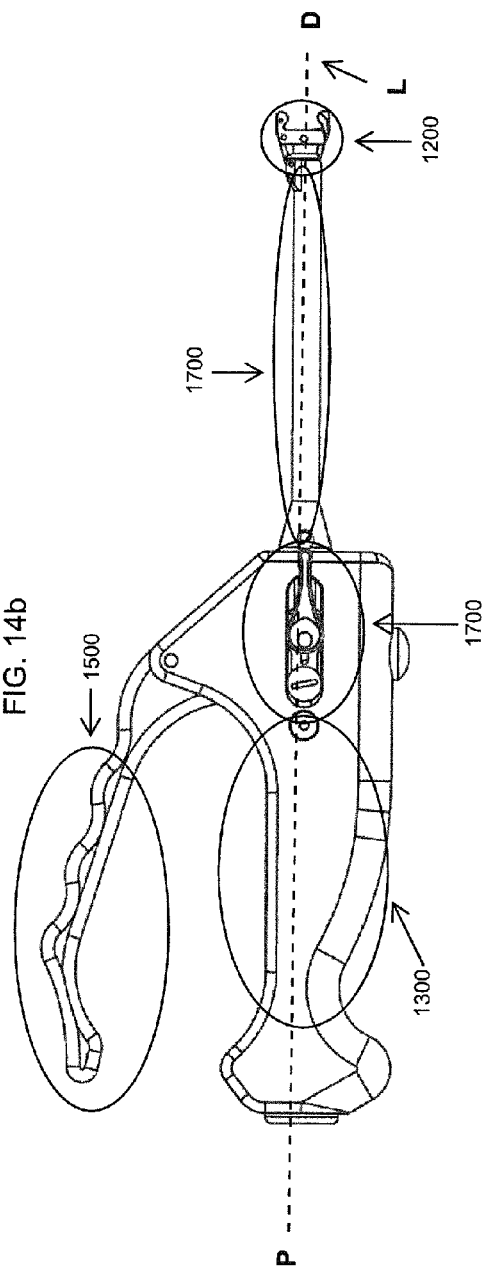

FIGS. 12-14 illustrate first and second embodiments 100, 1100 of aspects of the present invention. Both embodiments are configured to minimally invasively insert an orthopedic implant, actively steer the implant from between at least 0 to 90 degrees percutaneously, and release the implant in any surgeon-desired orientation. Embodiments 100, 1100 share some common elements.

FIGS. 13 and 14 depict two elongate implant insertion instruments 100, 1100. Instrument 100 and 1100 have a distal end D and a Proximal end P with a longitudinal axis L. For the purposes of describing similar elements, correlating numbers (i.e. 100 and 1100) will be used. Elongate implant insertion instruments 100 and 1100 have elongate external shaft members 400, 1400 with implant engaging portions 200, 1200 extending distally therefrom. Movably housed within the external shaft members are rotation shafts 440, 1440 and inner elongate release shafts 460, 1460. Instruments 100, 1100 have handle portions 300, 1300 housing a portion the elongate external shaft members 400, 1400 and slap hammer knobs 320, 1320 extending proximally therefrom. Implant rotating levers 500, 1500 extend and are pivotally hinged to handle portions 300, 1300. Implant release mechanisms 700, 1700 respectively are present on both instrument embodiments, but appear in different forms and locations.

Figure 15:
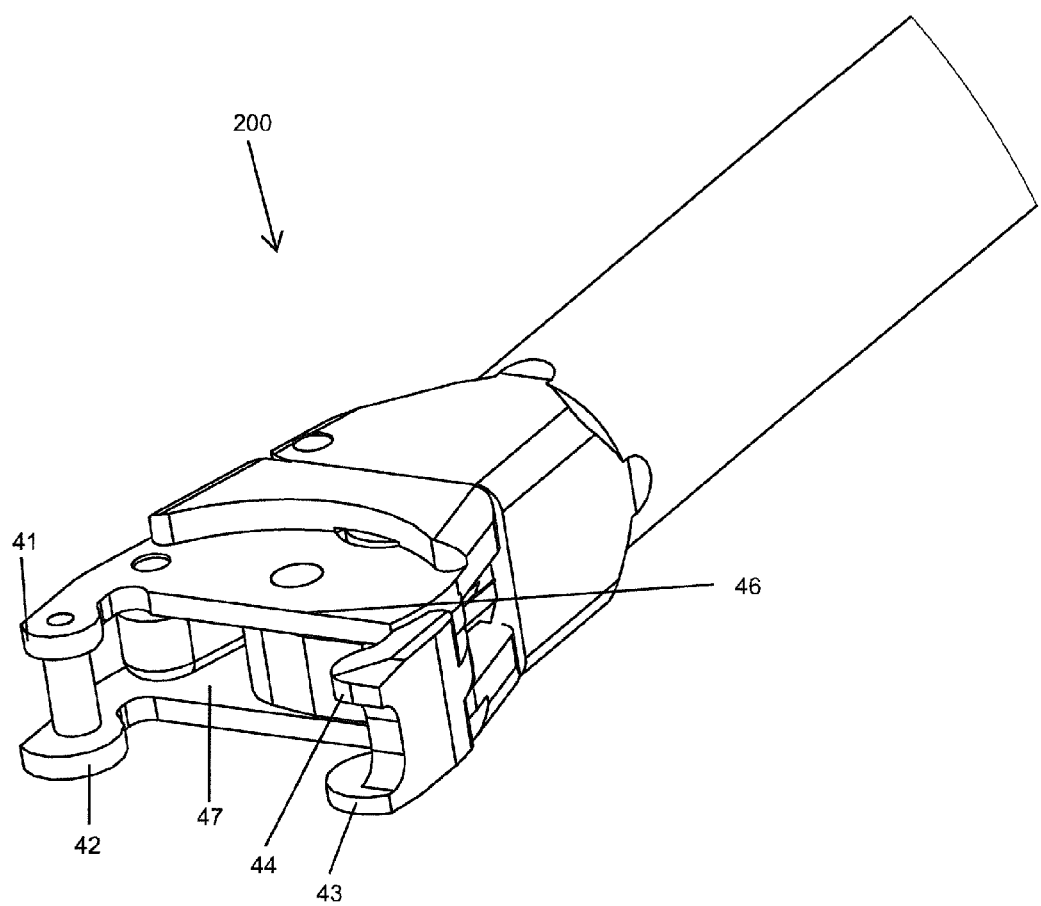
FIG. 15 is a perspective view of the distal end of the head or implant engagement portion of the insertion instruments of FIGS. 13a and 13b.
Figure 16:
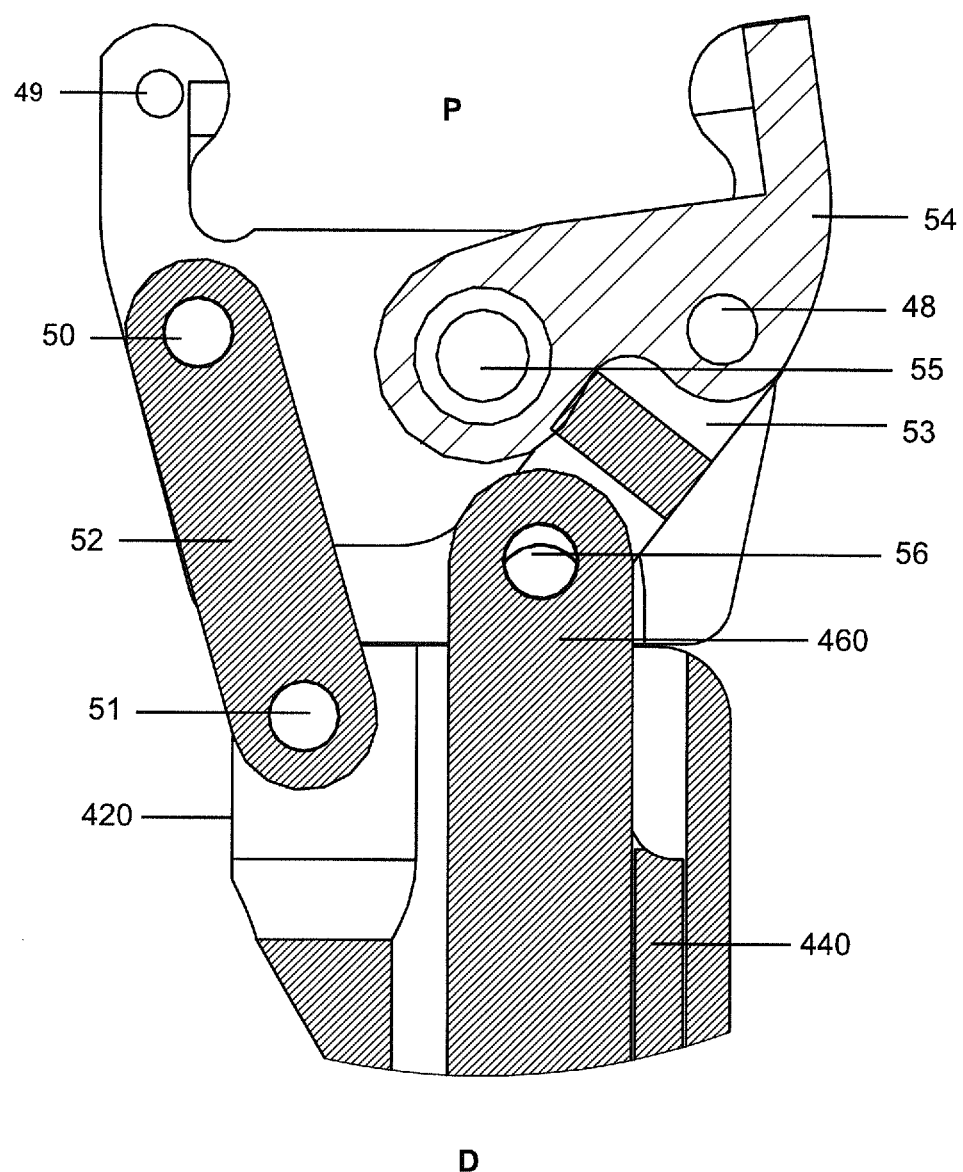
FIG. 16 is a section view of the head or implant engagement portion of the insertion instruments of FIGS. 13a and 13b.
Figure 17:
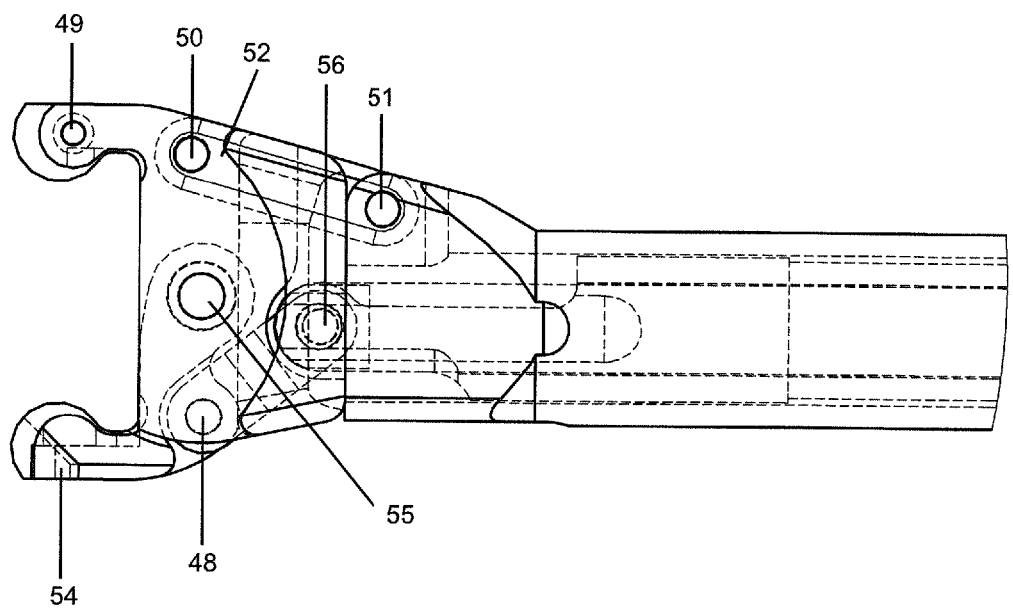
FIG. 17 is an elevation view of the head portion of the insertion instruments of FIGS. 13a and 13b, with hidden objects in dotted line.

Turning now to FIGS. 15-17 depicting implant engagement portions 200, 1200. The implant engagement mechanisms are alike on both inserters 100 and 1100 as are their respective operations of grasping, rotation and release of the NRD. Engagement mechanisms comprise implant clamping fingers, 41-44 which are configured to reside in the undercut or recesses of instrument engaging portions, 13-16, 113-116 and 33-36 of both upper 10, 10A and lower 30 implant shells respectively.

Engagement mechanism 200 includes two external plates 46, 47 which are pinned together at pivot points 48-51. This arrangement allows for the housing of linkage bars 52-54, with arcuate clamping fingers 41-44 disposed on the distal ends thereof for facilitating the ability to steer and release implant 1. Linkage bar 53 is movably pinned at its distal end to linkage 54 at point 55 and at its proximal end it is movably pinned to distal end of inner release shaft 460, 1460 at point 56. Detents (not shown) are machined on the inside of both external plates, 46 and 47 that mate with corresponding holes 442, 1442 located on the distal end of the insertion instrument's rotating shaft 440, 1440. Linkage bar 52 is movably pinned at hole 51 concentric to hole 422, 1422 of elongate external shaft 420, 1420 of instruments 100, 1100.

To ready instrument 100, 1100 to receive implant 1, the implant release shaft 460, 1460 is advanced proximally independent of middle rotation shaft 440, 1440 and fixed external shaft 420, 1420. Because of the pinned relationship of release shaft 460, 1460 to linkage bar 53 and the relationship of linkage element 53 with linkage element 54, the urging of the release shaft in a proximal direction causes linkage elements 53, 54 to move proximally about hinge pin 55 resulting in the distal end of linkage element 54 moving away from longitudinal axis L. With the distal end of linkage element 54 moved away from the longitudinal axis, the implant 1 can easily be inserted onto the clamping fingers. With the implant 1 placed in the insertion position, the operator allows inner release shaft 460, 1460 to return distally to its original position, bringing the clamping fingers into engagement with the implant engaging recesses 13-16, 33-36, thus firmly grasping implant 1.

Figure 18:
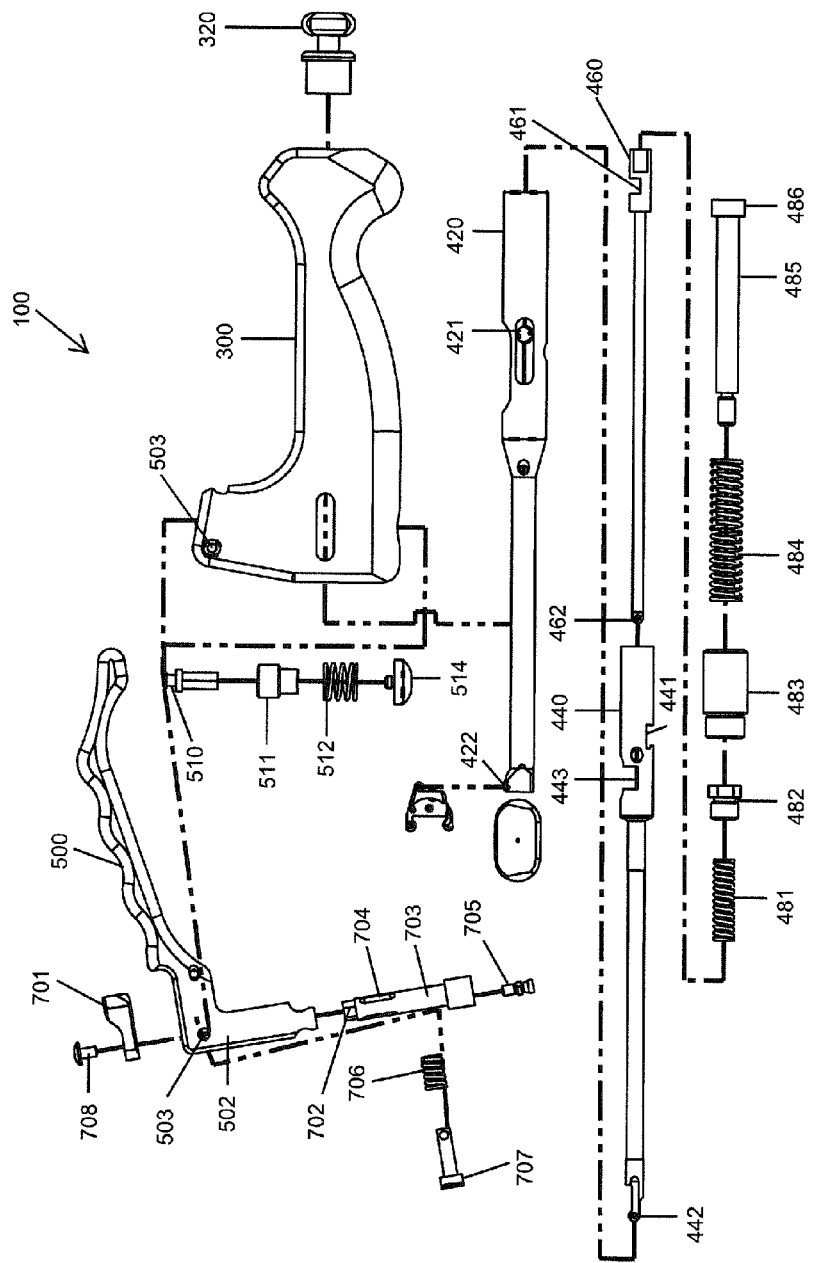

Implant insertion instrument 100, 1100, 2100 has an elongate shape enabling the physician to position, manipulate, and release an implant through a narrow working corridor within the patient. FIG. 18 illustrates an exploded view of embodiment 100 of an implant insertion device comprising a first elongate external shaft 420, a second elongate intermediate rotation shaft 440 and a third inner release shaft 460. External shaft 420 is fixedly attached to handle 300. Rotation shaft 440 movably resides in fixed external shaft 420. Release shaft 460 resides within the rotation shaft and translates, independently of or cooperatively with rotation shaft 440.

Rotation spring housing 483 comprises proximal end 487 and distal end 488 consisting of varying diameters with male threads disposed thereon. Threaded proximal end 487 of housing 483 engage female threads within handle 300, distal end threads 488 engage female threads in proximal end of the external shaft (not shown) fixing proximal end of external shaft 420 to handle 300. External shaft 420 extends distally through bore 303 in handle 300 thus supporting and housing the shaft. Shoulder bolt 485 extends longitudinally through rotation spring 484 with the coils thereof extending thereabout and spring housing 483 with the distal end of bolt 485 threadedly residing in proximal end 489 of release spring nut 482. Distal end 490 of release spring nut 482 abuts release spring 481 and threadedly engages proximal end of rotation shaft 440. Elongate release shaft 460 movably resides in rotation shaft 440. The arrangement of shafts 420, 440, 460, in cooperation with shoulder bolt 485, rotation spring housing 483, release spring nut 482 and springs 484,484 permits the translational movement of the release shaft independently or cooperatively with the rotation shaft. Both the rotation shaft and the release shaft are configured to translate independent of stationary external shaft 420.

Proximal end of rotation spring 484 abuts shoulder 486 of shoulder bolt 485 while distal end of spring 484 resides within larger diameter of housing portion 487 abutting the proximal smaller diameter 488 of housing 483. The outer diameter of spring 484 is slightly less than the inner diameter of proximal end of housing portion 487, but larger than the inner diameter of distal portion 488 of housing 483. Spring 484 is captured between the housing and the shoulder of shoulder bolt 486. As rotation shaft is advanced proximally, rotation spring 484 is compressed thus urging rotation shaft in a proximal direction.

Referring now to FIG. 25 release spring 481 is captured within the inner diameter of rotation shaft 440 in a space defined by the proximal end of rotation shaft 440 and the distal end of release collar 482. During assembly release spring 481 is installed in instrument 100 in a compressed state. Since the release spring is in compressed and resides in the space previously described it constantly biases or urges release shaft 460 in a distal direction. Due to the pinned relationship of release shaft 460 with linkage bar 53 and the pinned relationship of linkage bar 53 with linkage bar 54, the distal urging of the release shaft urges the linkage bars distally and thus the implant is firmly grasped as clamping fingers 43,44 are persuaded toward the longitudinal axis of instrument 100.

Figure 21:
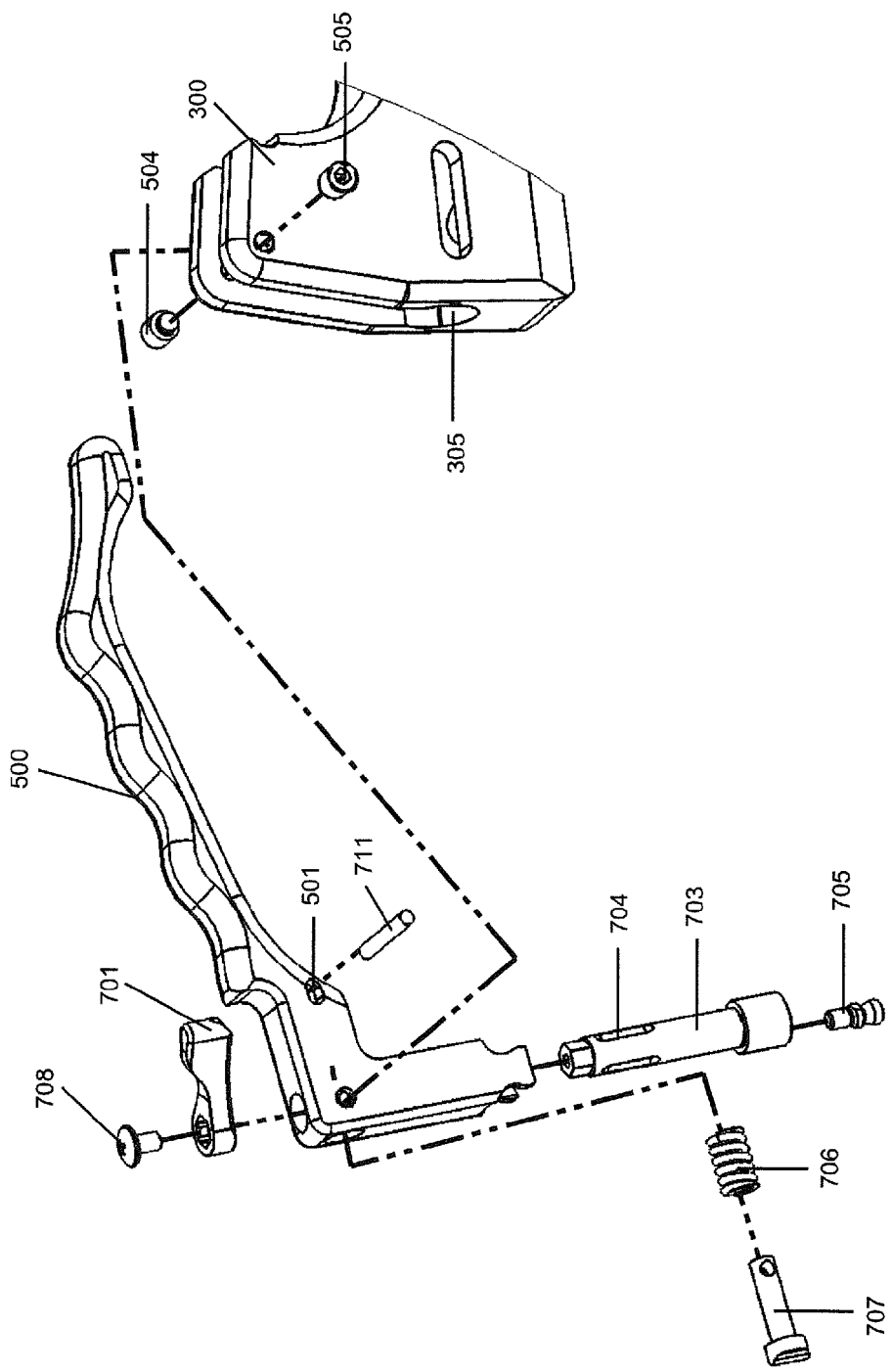
Figure 22A:
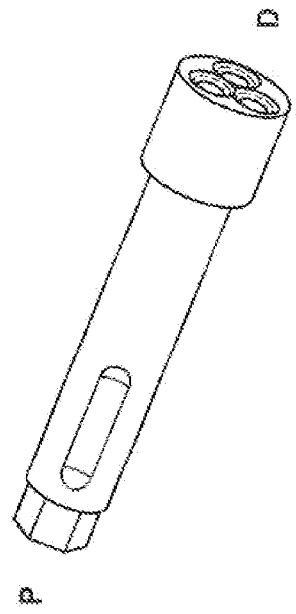
Figure 22B:
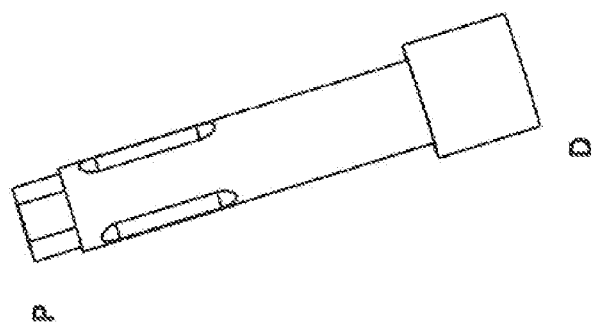
Figure 22C:
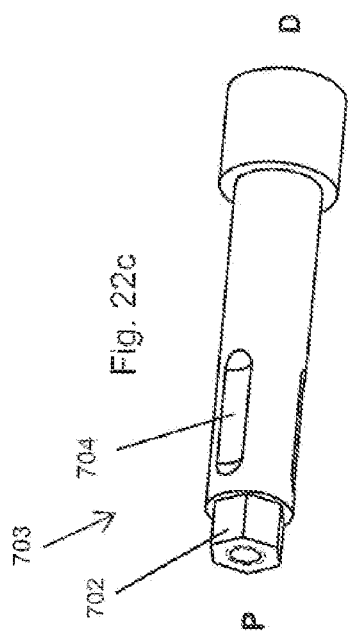
Figure 22D:
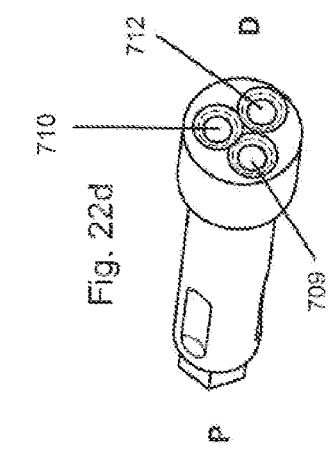

Turning now to FIGS. 21-31 relating to insertion instrument 100. FIG. 21 is an exploded view of the rotation and release mechanisms. Both the rotation and release mechanisms are housed within distal portion of rotation lever 500 and distal portion of handle 300. Release mechanism comprises a release lever 701, elongate release lever shaft 703, offset release post 705, locking post 707, and release lever locking spring 706.

Figure 27:
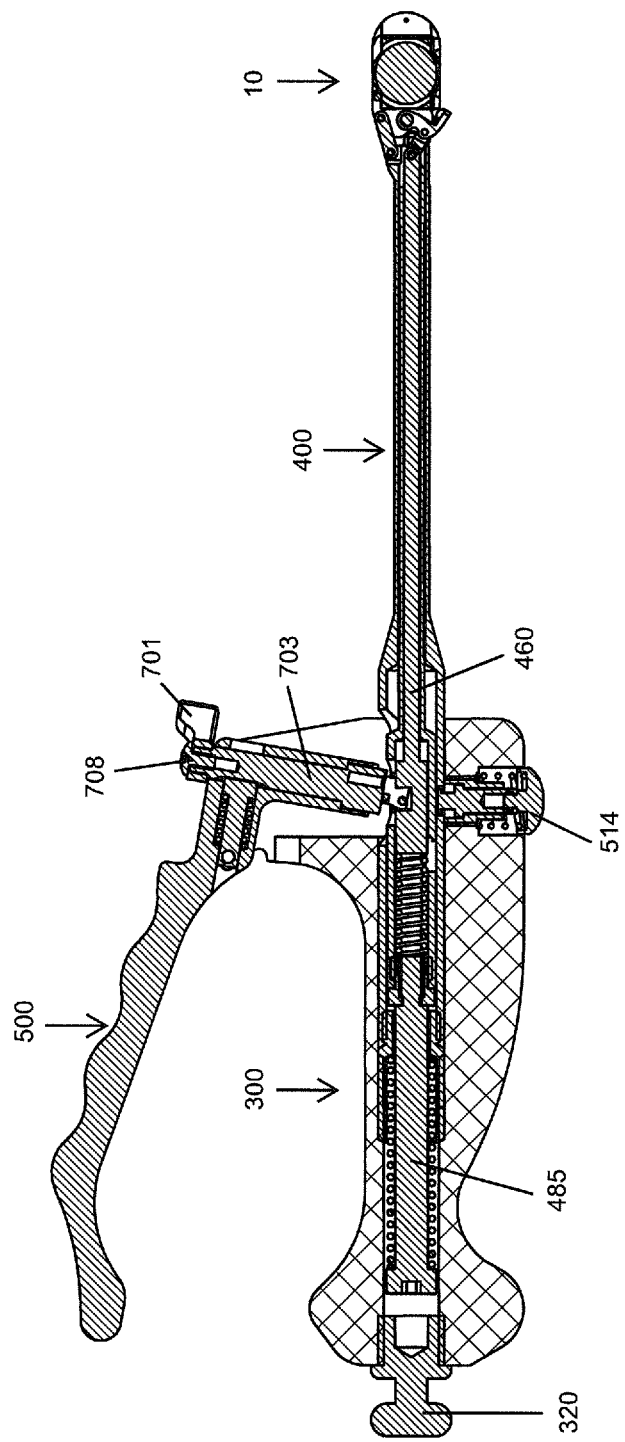
Figure 28:
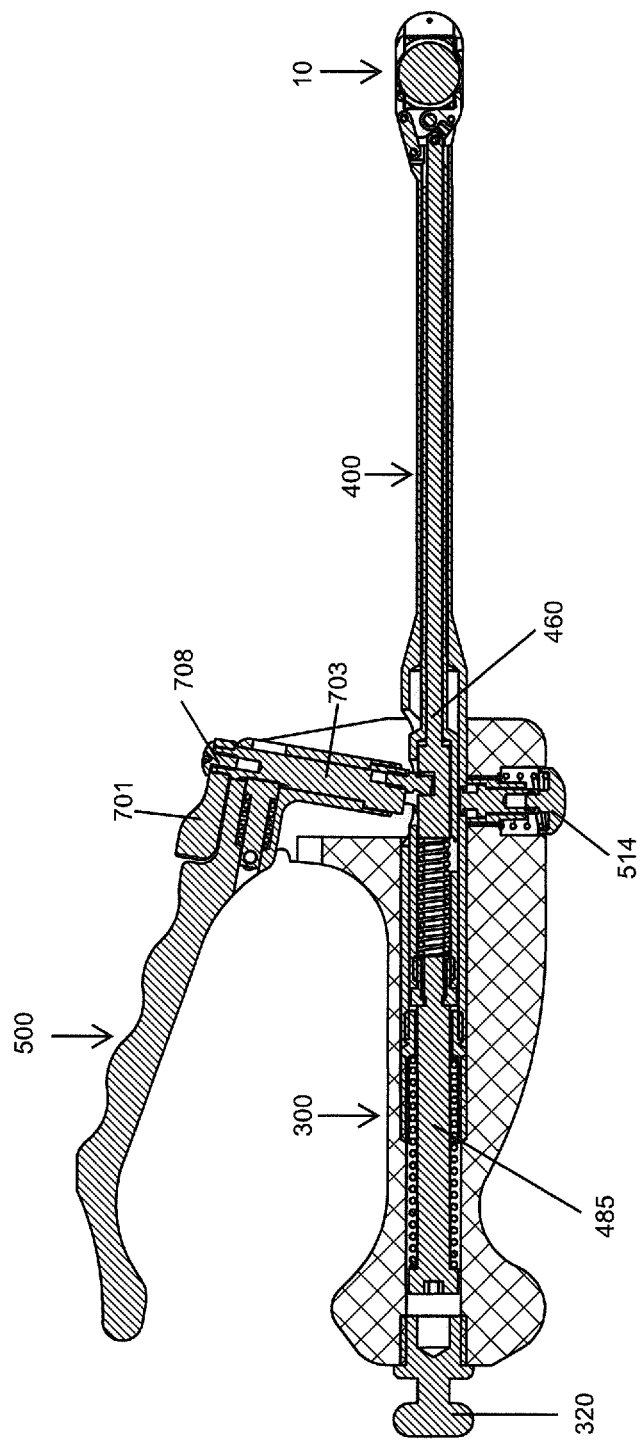
Figure 29:
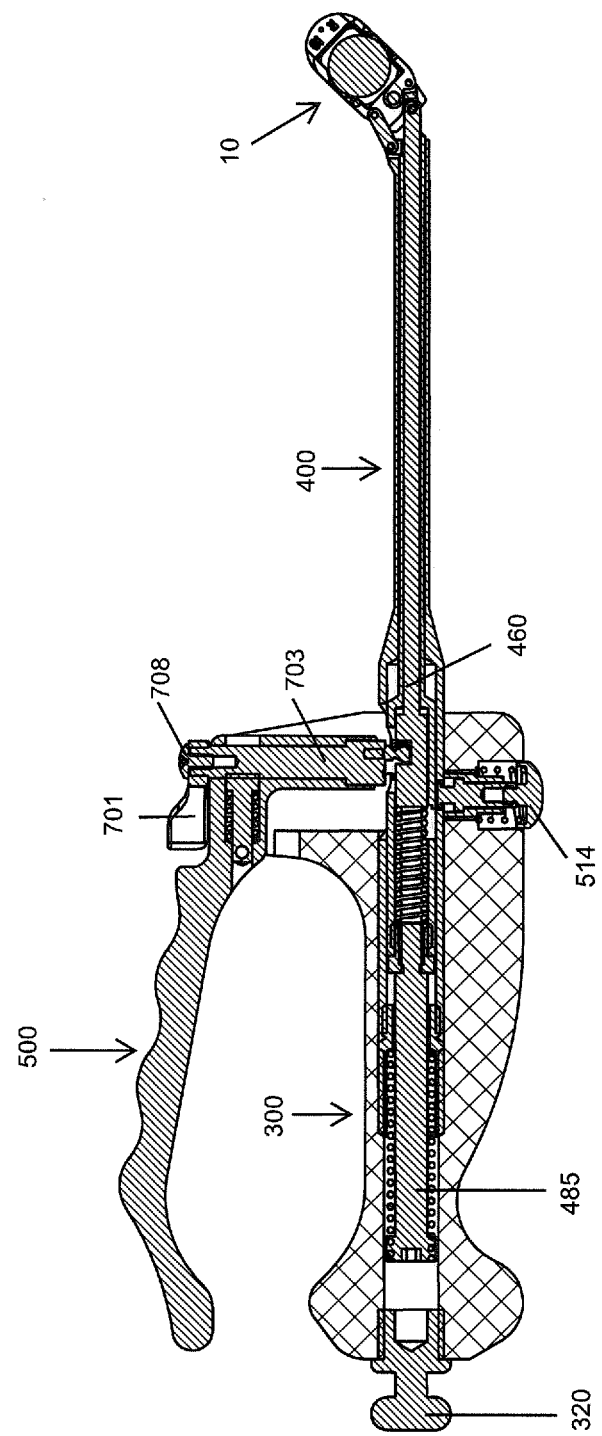

Elongate release lever shaft 703 comprises a proximal and distal end. Disposed on the proximal end P of the release lever shaft has a multi-faceted male configuration 702, in this case a hexagonal configuration that substantially matches the female configuration of aperture 701A of release lever 701. The diameter of distal end D of release shaft 703 is slightly larger than that of the main shaft body portion. Disposed on the distal end of release shaft 703 are three apertures 709, 710, 712 which house offset release post 705. The proximal end of post 705 is disposed in any of the three apertures and thus is radially offset from the central axis of release shaft 703. When release lever 708 is rotated to the open position as seen in FIG. 27 the central axis of the offset post is proximal the central axis of the release shaft. When release lever 708 is rotated to the closed position as seen in FIG. 28 the central axis of offset post 705 is distal the central axis of release shaft 703. Each of the three offset release post apertures are arranged at slightly differing distances from the central axis of the release shaft respectively. The variable distances allow for the post to be attached to the shaft in any of the three various positions thus allowing for minor adjustment when assembling instrument 100 to obtain the desired proximal and distal travel of the offset release post relative to release post activation slot 461 of release shaft 460.

With the release shaft 460 constantly being urged distally by release spring 484, it is desirable to be able to lock the release shaft in the open position while the implant is readied for placement on the instrument. The locking of release shaft 460 in the open position, as seen in FIG. 23, achieved by release lever locking post 707 in concert with release shaft locking slots 704, lever locking spring 706, lever locking pivot pin 711 and slot 501 and locking pin ramp 500R of handle 500. In addition to holding the lever in the open position for the mounting of implant 1, this arrangement also prevents the rotation of the implant while the lever is in the open position.

As can best be seen in FIG. 23, lever locking post 707, and spring 706 are disposed in bore 516 in rotation lever 500. Bore 516 has a proximal diameter 516P and a distal diameter 516D. Diameter 516P is slightly larger than the diameter of the shaft portion of locking post 707. Diameter 516D is slightly larger than that of spring 706 and the release slot engaging portion of locking post 707. Locking post pin 711 is disposed in slot 501 of handle 500 and press fit in the bore of the shaft portion of the locking post. Pin 711 translates freely within slot 501 and along ramp 500R, as rotation lever 500 is employed, while retaining the locking post within bore 516. Spring 706 urges locking post 707 in a proximal direction toward release lever shaft 703.

Turning now to FIG. 21, distal end of rotation lever 500 is disposed within handle 300. Rotation lever locking screws 504, 505 have a larger diameter threaded end with interior geometry to accept a tool for rotation during assembly. Inside portions 504S, 505S of the locking screws have a smooth surface with a smaller diameter which engage rotation lever 500 in lever pivot pin bore 503. The locking screws 504, 505 capture rotation lever 500 in handle 300 allowing the lever to pivot about the locking screws. The arrangement of two locking screws allows the interior of lever 500 to receive release lever shaft 703 therein.

When rotation lever 500 is moved toward handle 300 the rotation lever pivots about locking screws 504, 505 thus urging release lever shaft 703 and offset post 705 in a distal direction. The disposition of offset release post 705 in release lever engagement slot 461 of release shaft 460 forces the release shaft and rotation shaft 440 to move distally relative to elongate external shaft 420 in response to the movement of the rotation lever on rotation shaft. Rotation shaft 440 comprises a bore 442 at its distal end. The distal end of the rotation shaft is sandwiched by plates 46, 47 of the implant clamping mechanism and two bosses (not shown) secure the rotation shaft 440 to plates 46, 47. The bosses lie inferiorly on plate 46 and superiorly on plate 47. The location of the bosses is concentric with pivot point 56 which is attached to release shaft 460. The bosses do not protrude completely through distal bore 442 thus the release shaft is able move proximally independent of the rotation shaft.

With rotation shaft 440 moved distally relative to fixed elongate outer shaft 420, the longitudinal axis of implant has been shifted from being substantially parallel to longitudinal axis L of instrument 100 to being substantially transverse to the longitudinal axis of the instrument. It is preferable, but not required, to be able to temporarily lock rotation shaft 440 in this position so that the surgeon can remove himself from the fluoroscopic field.

The locking of rotation shaft 440 in the 90 degree configuration is accomplished by a rotation locking mechanism as seen in FIG. 23. The locking mechanism comprising rotation locking button 513, locking collar spring 512, locking collar 511, and rotation shaft locking post 510. Rotation locking collar 511 comprises a superior diameter and an inferior diameter 517. The inferior diameter of locking collar 511 is fixedly disposed, by threads, press fit or any other means known in the art, in aperture 304 of handle 300. Rotation shaft locking post 510 is disposed in locking collar 511. Collar spring 512 is disposed about inferior diameter 517 abutting superior diameter of collar 511. Shoulder of rotation locking button 514 abuts inferior portion of spring 512 and is fixedly attached to inferior end of post 510. Spring 512 urges button 514 and fixedly attached post 510 in a direction inferior to that of rotation shaft 440.

Figure 30A:
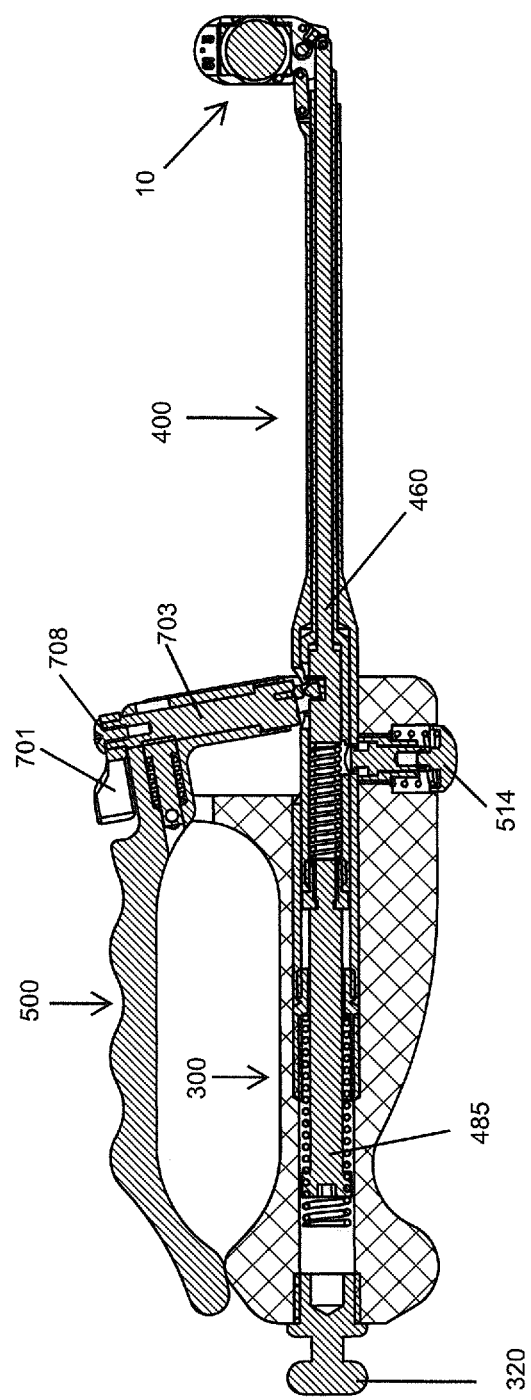
Figure 30B:
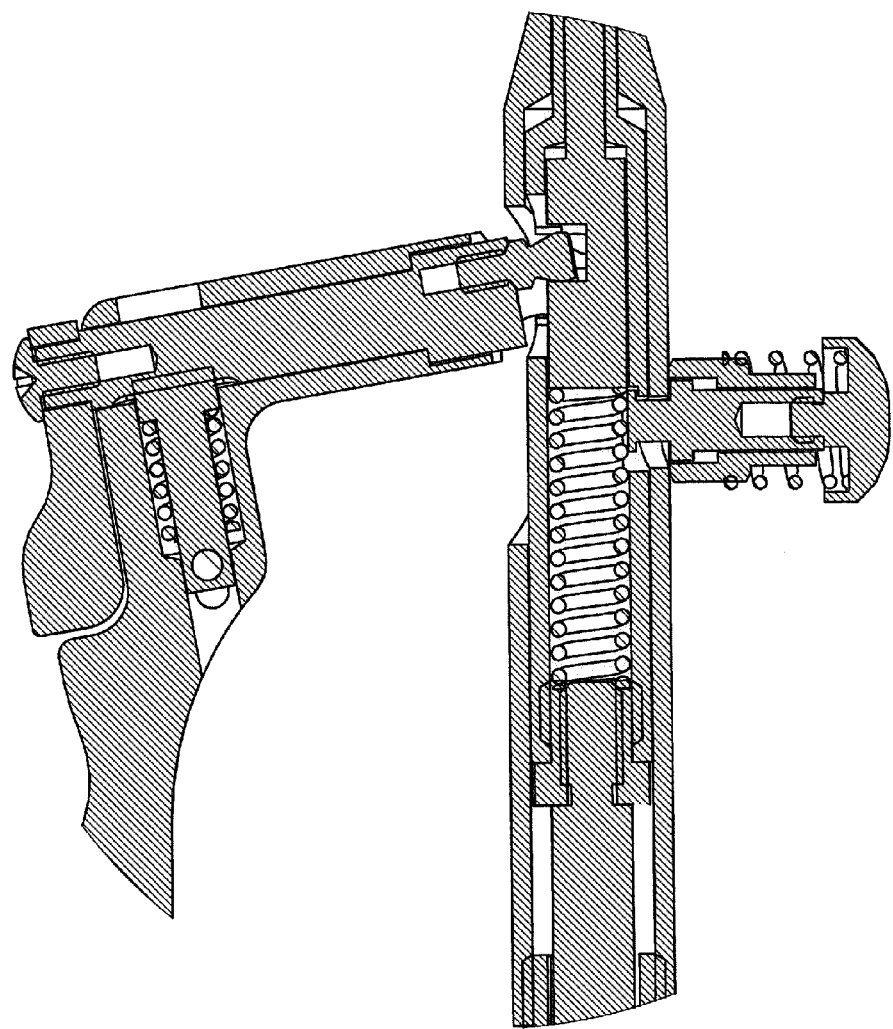

As seen in FIG. 30A, upon the distal advancement of rotation shaft 440 due to the employment of rotation lever 500 rotation locking engagement portion 441 of shaft 440 resides superior to that of rotation locking post 510. In this position, the surgeon depresses button 513 urging locking post 510 into the locking engagement portion 441 of rotation shaft 440. As lever 500 is released, spring 484 urges rotation shaft proximally resulting in the locking post 510 residing in the distal end of engagement portion 441 of rotation shaft 440, as can be seen in FIG. 30B. The locking post secures the rotation shaft in a distal position until such a time that rotation lever 500 is moved inferiorly toward handle 300. The inferior movement of lever 500 urges rotation shaft distally allowing rotation lock spring 512 to urge locking post 510 out of engagement with locking portion 441 of rotation shaft 440. Spring 484 urges the rotation shaft proximally returning the instrument back to a zero degree configuration.

Turning now to a method of employing embodiment 100 in the implantation of artificial nucleus 1. After the method and approach of insertion are determined and the target disc space identified, access is made to the surgical site via any number of surgically accepted methods. Access to the damaged disc is obtained by creating a small window in the annulus. Once the disc has been excised or otherwise prepared, instruments are deployed to determine the size of the implant to best suit the anatomy of the patient. Upon determining the appropriate size, the corresponding implant 1 is selected and placed in a jig (not shown) to hold implant 1 firmly while implant insertion instrument is prepared for clamping implant 1.

Figure 26:
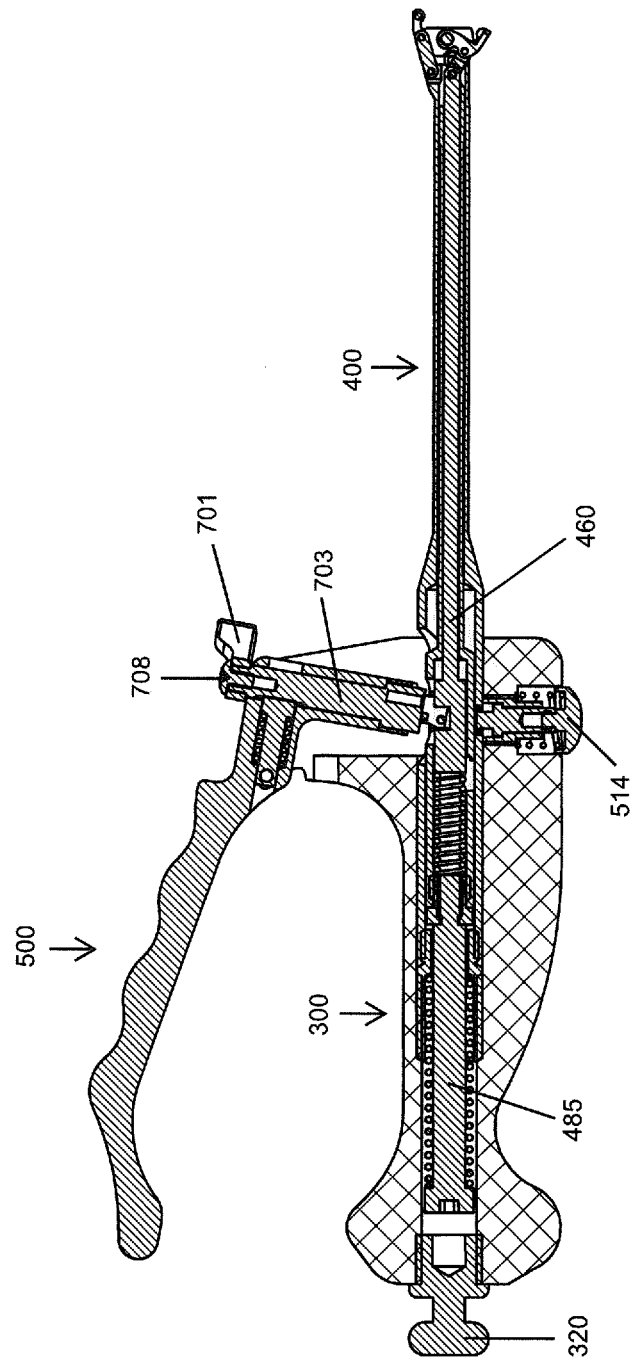

Turning now to FIGS. 26-31, instrument is grasped at handle 300 and implant release ever 701 is moved to the open position shown in FIG. 26. The clamping fingers 41-44 are placed near their respective instrument engagement recesses 13-16, 33-36 of the implant as shown in FIG. 27. Implant release lever 701 is manually returned to the closed position as seen in FIG. 28 resulting in the implant being firmly grasped, with the longitudinal axis of implant 1 substantially parallel to longitudinal axis L of instrument 100, and ready for insertion. The implant is placed through the annular window and eased into the disc space in the zero degree configuration so that the footprint of implant 1 and delivery device 100 is reduced.

The implant 1 is then rotated within the disc space to the substantially 90 degree configuration. The rotation shaft locking button 514 is depressed moving locking post 510 to engage slot 441 in rotation shaft 440 thus locking the instrument in the 90 degree configuration. The surgeon may then remove himself from the fluoroscopic field while the exact position of the implant is determined. Adjustments are made and location determination is repeated until the desired position of the implant within the intervertebral space is achieved.

Figure 31:
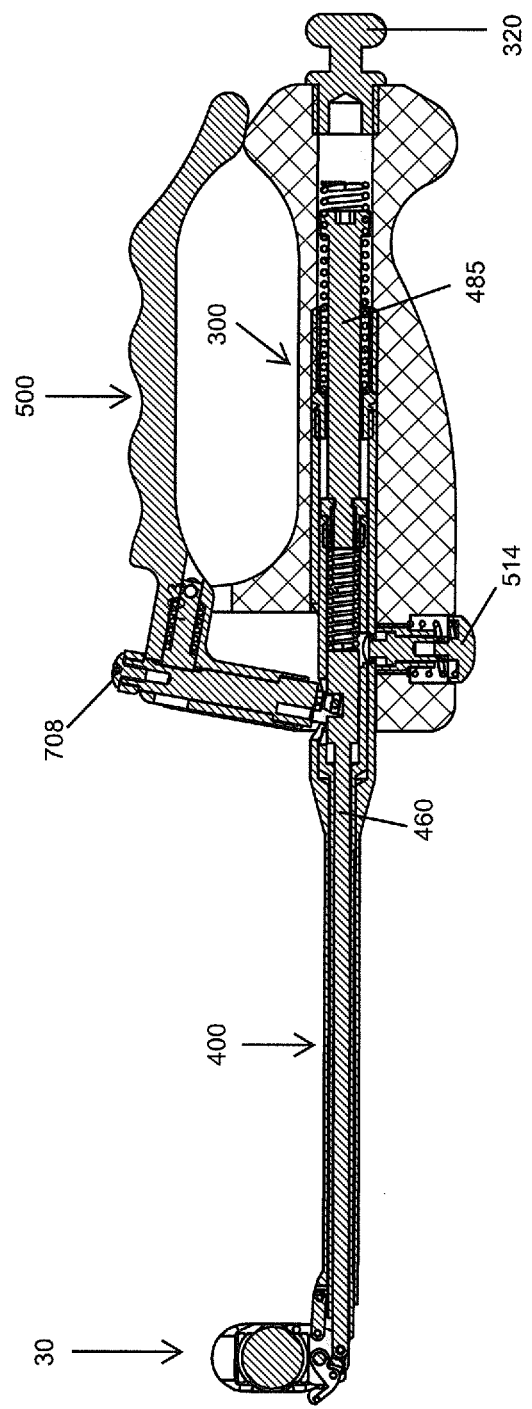

The surgeon then releases implant 1 from instrument 100 and removes distal end of the instrument through the annular window. Once removed from the implant, the instrument is preferably returned to the zero degree configuration and the clamping fingers returned to the grasping position so as to provide a smaller footprint. The smaller footprint limits damage that can be done to the interior of the annular window. To achieve this the surgeon turns release lever 701 to the release position as seen in FIG. 31 and slowly moves instrument 100 from contact with implant 1. A slight depression of rotation lever 500 toward handle 300 urges release shaft distally allowing spring 512 to force locking post 510 out of engagement with slot 441 of rotation shaft 440. Lever 500 is allowed to return to the neutral position causing pivot pin 711 to move proximally on ramp 500R. The proximal movement of pivot pin 711 in slot 501 disengages post 707 from slot 704. Spring 481 forces release shaft 460 distally thus returning clamping members 41-44 to the clamping position, as seen in FIG. 24A, providing a small footprint for removal via the annular window.

Figure 32:
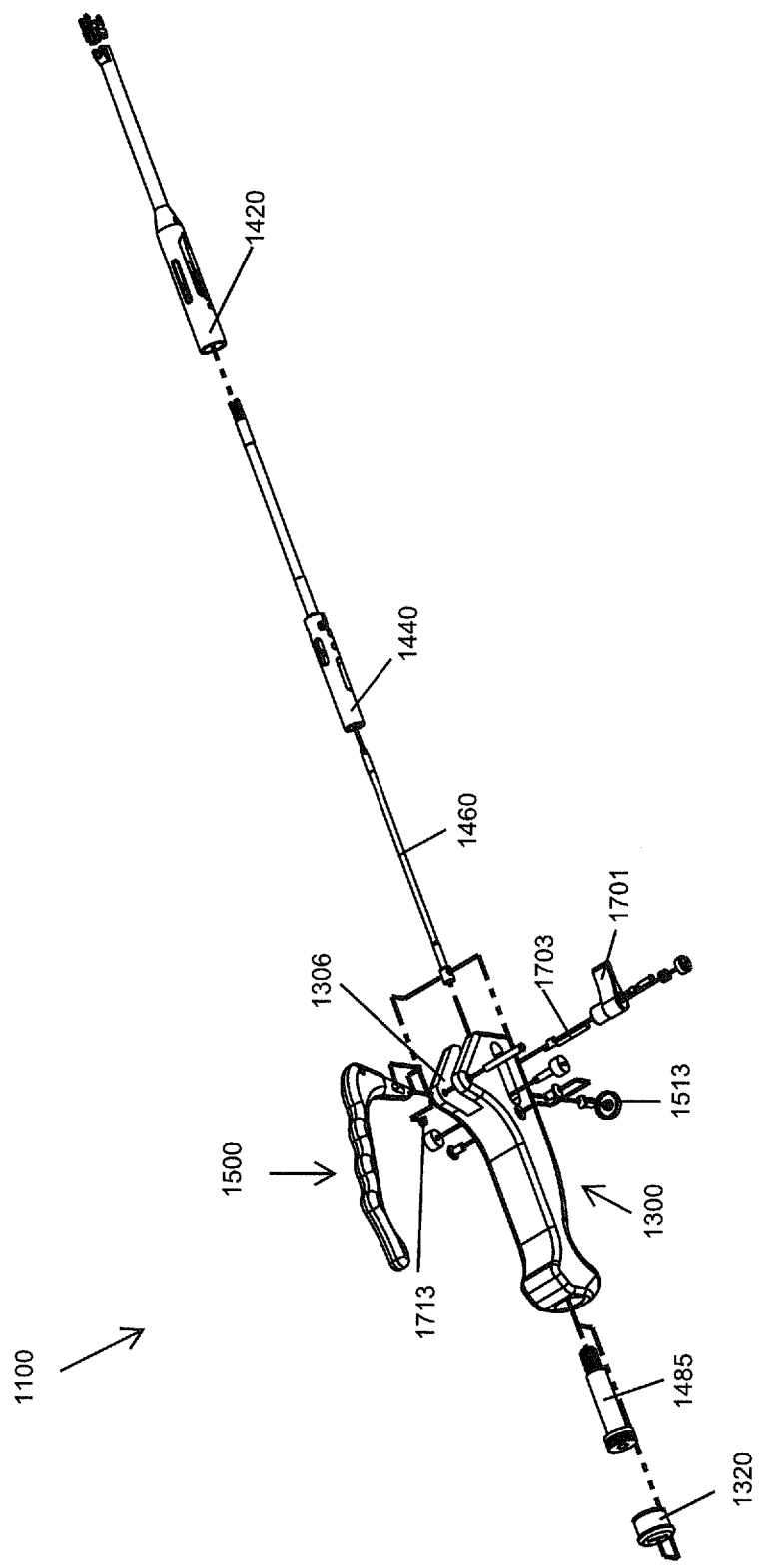
FIG. 32 is an exploded view of an alternate embodiment of an insertion instrument according to the present invention.
Figures 34A, 34B, 34C:
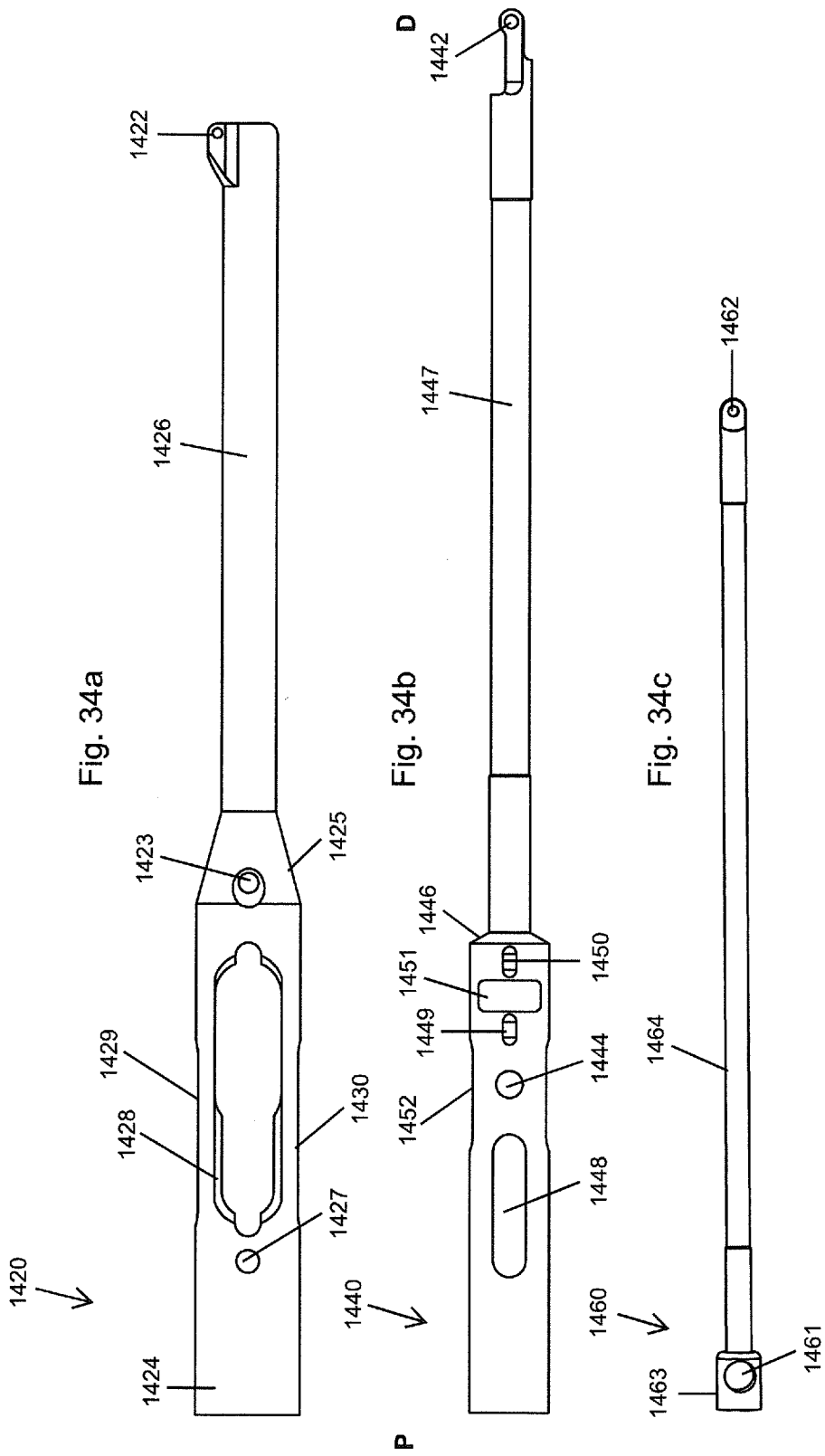
FIGS. 34a-34c are elevation views of shaft members of the insertion instrument of FIG. 32.

An alternative embodiment 1100 of an artificial disc insertion device can be seen in FIGS. 32-46. FIG. 32 is an exploded view of instrument 1100 comprising similar elements to that of instrument 100 including, but not limited to; fixed external shaft 1420, rotation shaft 1440, release shaft 1460, release lever 1701, handle 1300, implant engagement mechanism 1200, and rotation lever 1500. Instrument 1100 performs a similar function as instrument 100, with some design changes resulting in a slightly different method of operation.

In assembly, external shaft 1420 is fixedly attached to handle 1300 by fixation pins 1716, 1717 through aperture 1303 in handle 1300 and aperture 1427 in external shaft 1420. The pins 1716, 1717 breach the interior wall of external shaft 1420. Fixation pins may be attached to the external shaft by threads, press fit, welding or any fixation method commonly recognized in the art. Shaft 1420 comprises clamping mechanism engagement portion 1422 at its distal end, an aperture 1423 to receive a cleaning device (not shown) for sterilizing the inside, and disposed about the anterior and posterior of shaft 1420 are rotation lever slots 1429, 1430.

Movably disposed in external shaft 1420 is rotation shaft 1440 having an elongate configuration with proximal end P and distal end D. Proximal end has an internal female thread (not seen) that mates with male thread of shoulder bolt 1485. Rotation shaft spring 1484 is disposed between shoulder 1486 of shoulder bolt 1485 and proximal end of elongate external shaft 1420. Distal end D includes aperture 1442 for engaging the implant clamping mechanism. Rotation shaft 1440 further comprises a slot 1448 which houses the portion of fixation pins 1716,1717 that have breached the internal wall of external shaft 1420 and allows rotation shaft 1440 to move freely in a proximal and distal direction relative to external shaft 1420. Aperture 1444 receives rotation lever attachment bolt 1714 therethrough. Release shaft camming slot 1451 receives distal portion of offset release lever shaft 1703 therethrough. Distal to slot 1451 is slot 1450 which receives release lever locking ball 1719 in the closed position. Proximal to slot 1451 is slot 1449 which receives release lever locking ball in the open position. Disposed about the anterior and posterior of shaft 1440 is rotation lever slot 1452.

Movably disposed in rotation shaft 1440 is elongate release shaft 1460. Release shaft 1460 comprises proximal end P and distal end D. The release shaft further comprises an aperture 1462 disposed about the distal end of shaft 1460 for movable engagement with the implant clamping mechanism. Enlarged proximal shaft portion 1463 houses release lever engagement aperture 1461. In assembly, camming portion 1705 of offset release shaft 1703 is disposed within aperture 1460.

Figure 35A:
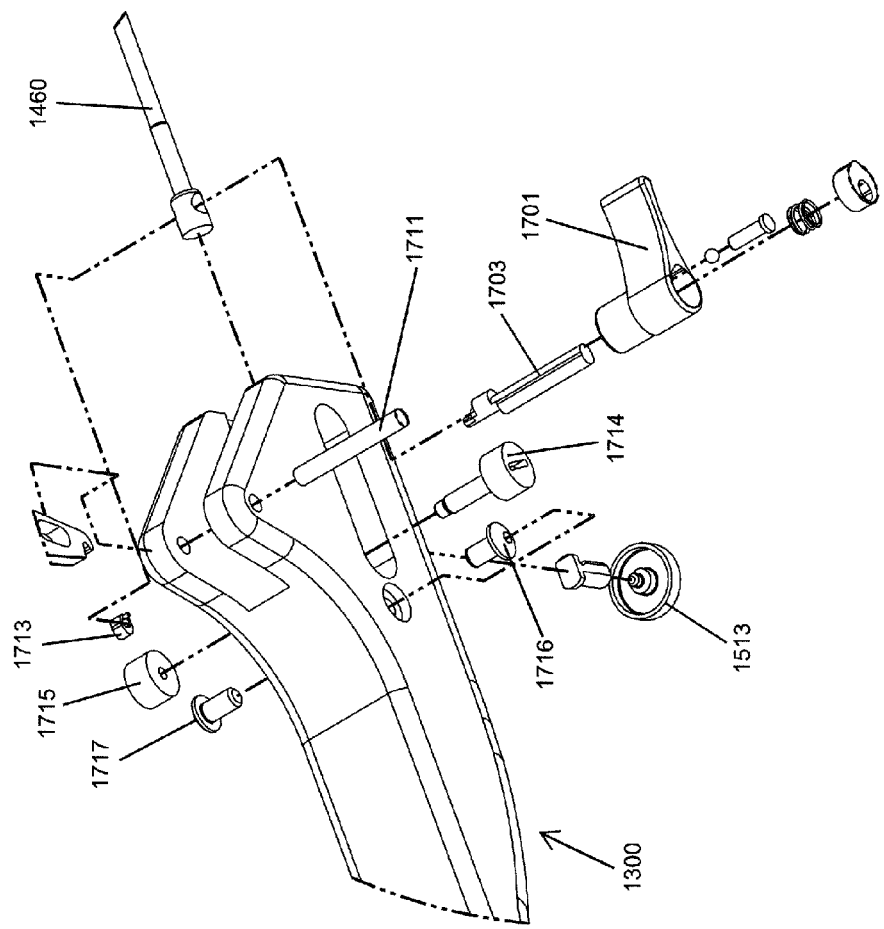
FIG. 35a is a exploded view of an actuator assembly of the insertion instrument of FIG. 32.
Figure 35B:
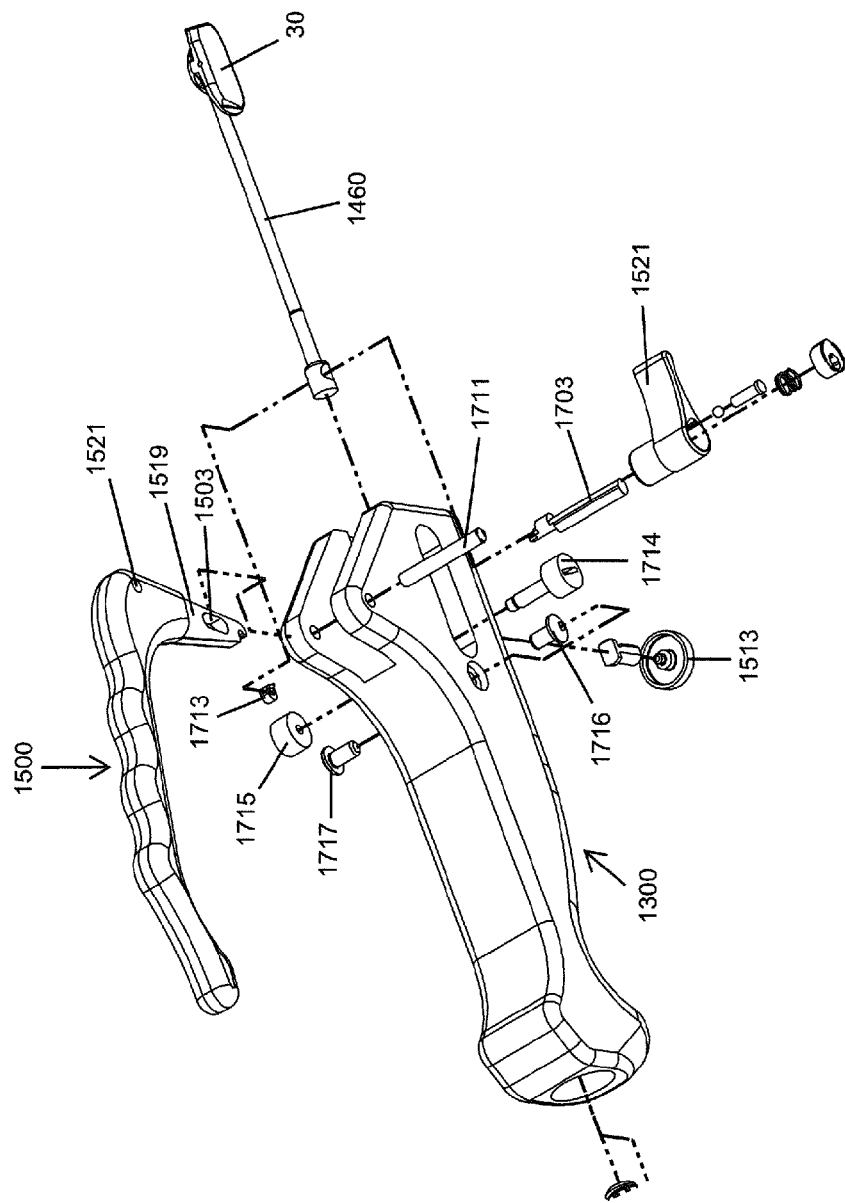
FIG. 35b is a partial exploded view of an actuator assembly of the insertion instrument of FIG. 32.
Figure 37:
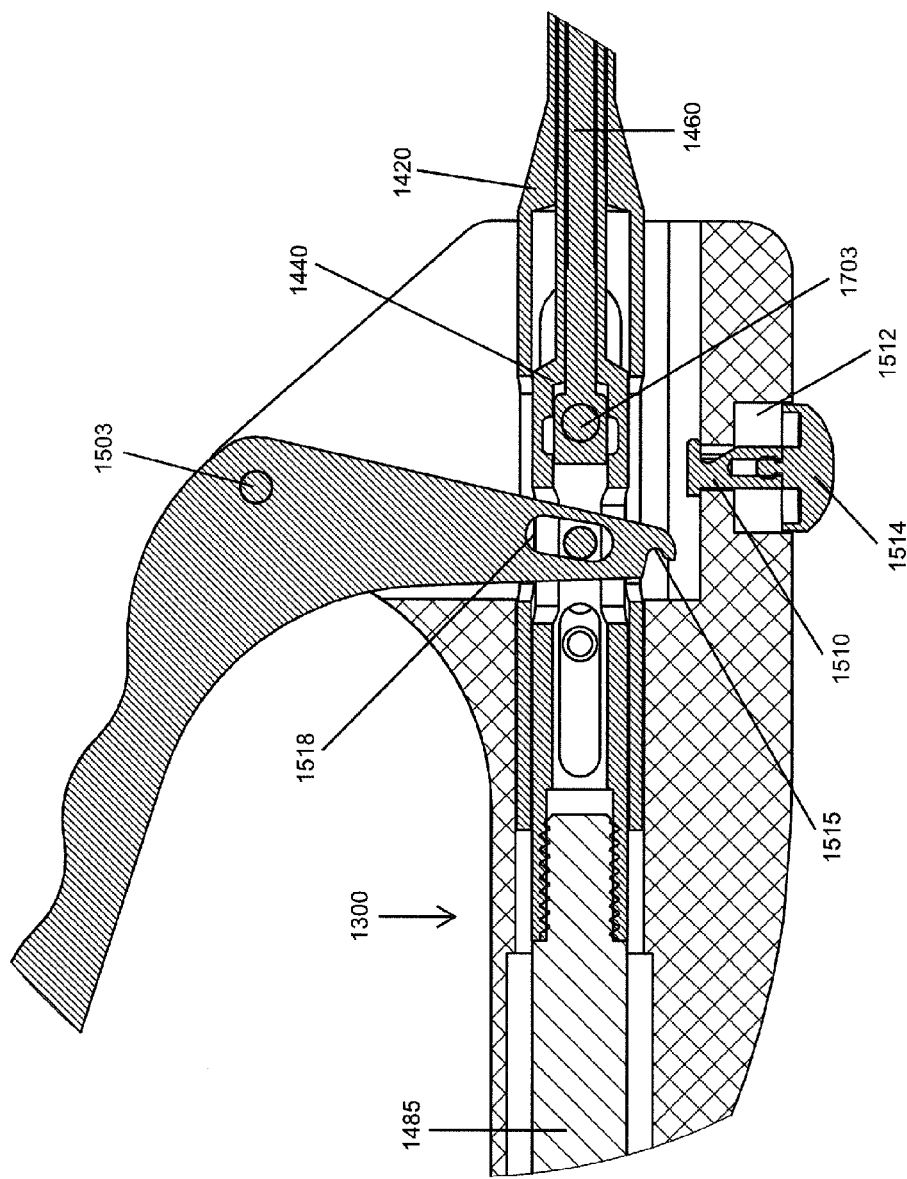

As best seen in FIG. 35B, rotation lever 1500 comprises a narrow shaft engaging portion 1519 having a width slightly less than the width of slots 1429, 1452 of external and rotation shafts respectively. Shaft engaging portion 1519 includes a slot 1520 therein for engaging the rotation lever attachment pin 1711. Inferior end of narrow engaging portion 1519 comprises a notch 1515 for engaging the superior portion of rotation shaft locking post 1510 for locking of the rotation shaft relative to the external shaft while the instrument is in the substantially 90 degree orientation. In assembly, inferior portion of rotation lever 1500 is deposited in slot 1306 of handle 1300. Narrow shaft engaging portion is disposed through slot 1429 of external shaft 1420, and slot 1452 of rotation shaft 1440 as seen in FIG. 37. Rotation lever pivot pin aperture 1521 is aligned with rotation lever pivot bore 1301 of handle 1300. Pivot pin 1711 is disposed in both bores and fixedly attached via press fit or laser weld. The arrangement allows rotation lever 1500 to move freely in handle slot 1306 and engage rotation shaft 1440. The bias force, in a distal direction, of rotation spring 1484 on shaft 1440 always urges distal portion of lever 1500 away from handle 1300.

Figure 45:
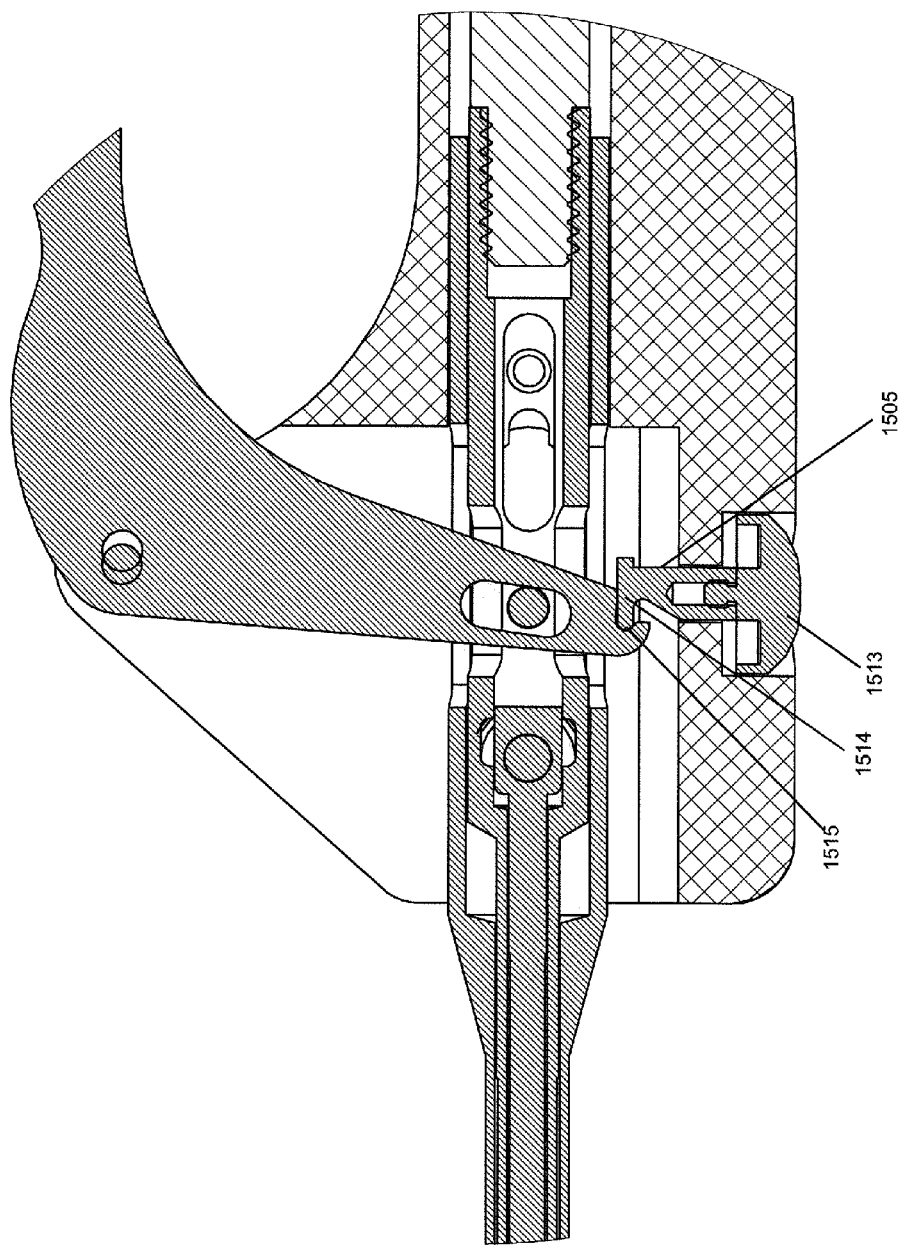
Figure 46:
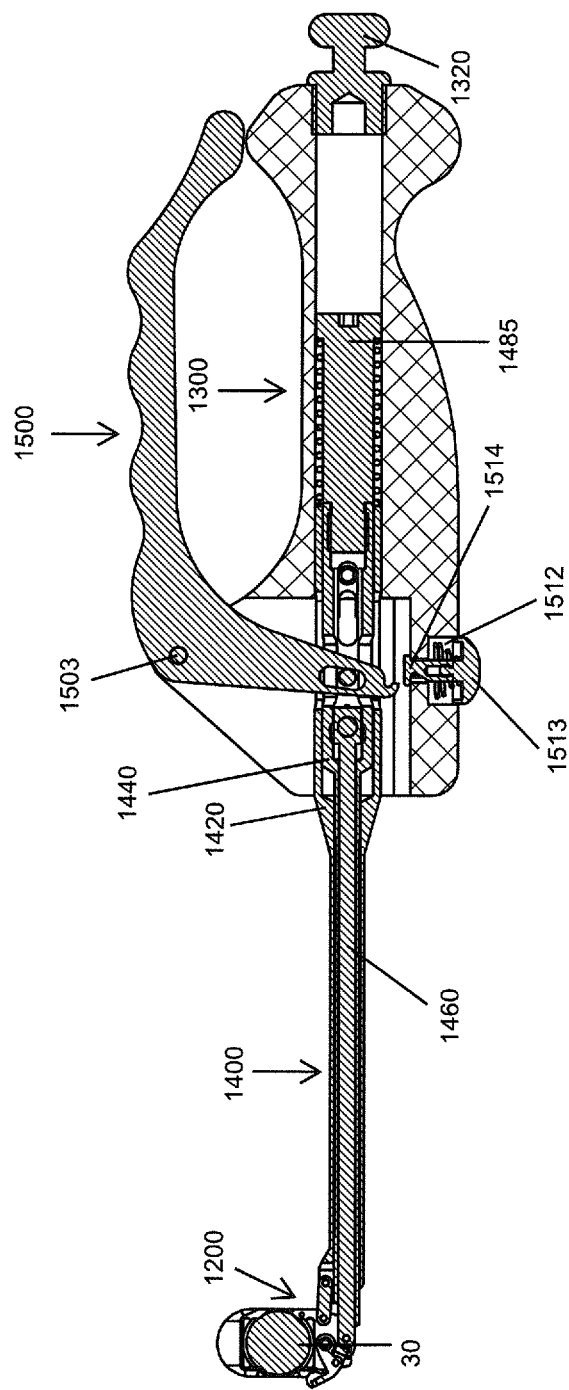

The locking of the rotation shaft in the 90 degree configuration is accomplished with a similar button, post, collar and spring configuration as that of instrument 100. As distal end of rotation lever 1500 is deployed about pivot pin 1711, locking notch 1515 nears locking post 1510 eventually residing distal post 1510. Locking button 1513 is depressed thus engaging locking post 1510 with locking notch 1515, as seen in FIG. 45, preventing rotation shaft 1440 from traveling in the proximal direction.

FIGS. 36A-C, 38 illustrate components of release mechanism 1700. Release mechanism 1700 comprises release lever 1701, release lever shaft 1703, fixed cap 1718, locking spring 1706, locking post 1707, locking ball 1719, and distal attachment cap 1713. The release mechanism 1700 performs the same function as that of previously disclosed mechanism 700 in that it engages release shaft urging release shaft 1460 proximally or distally thus engaging or disengaging implant 1 from clamping mechanism 1200.

Figure 38:
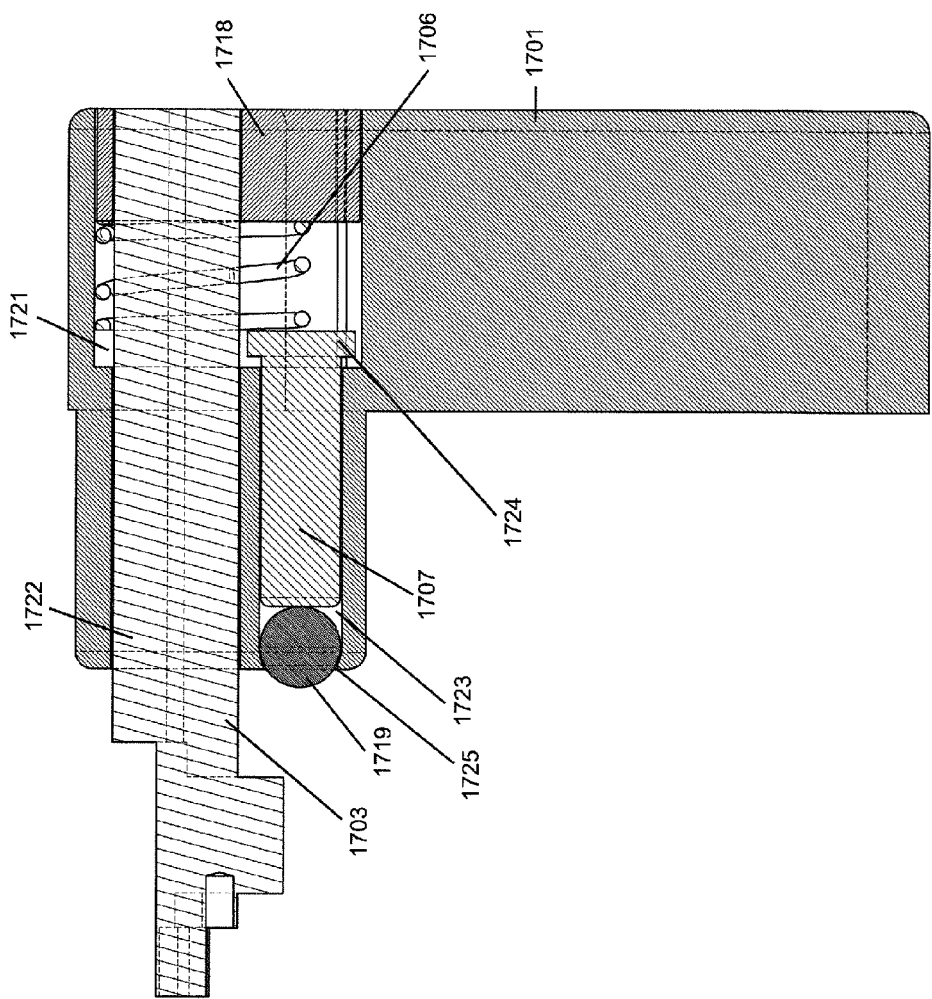
Figure 40:
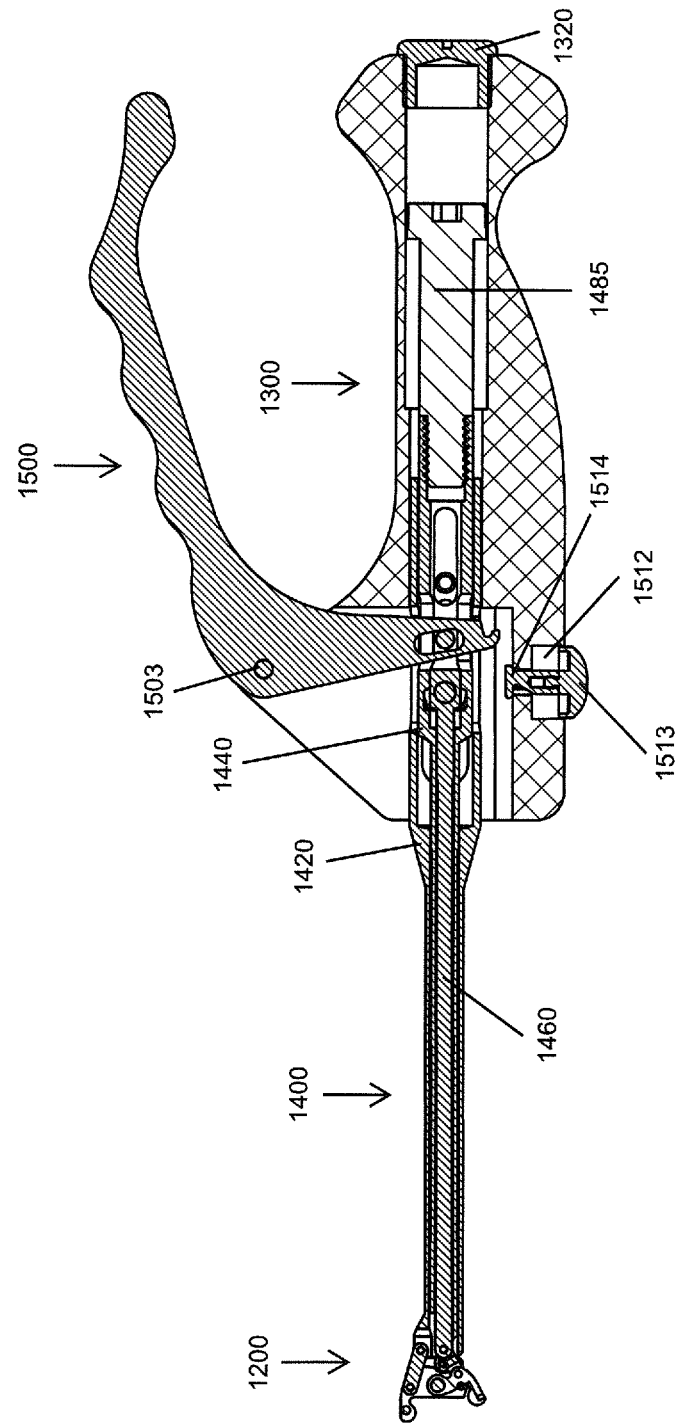
Figure 41:
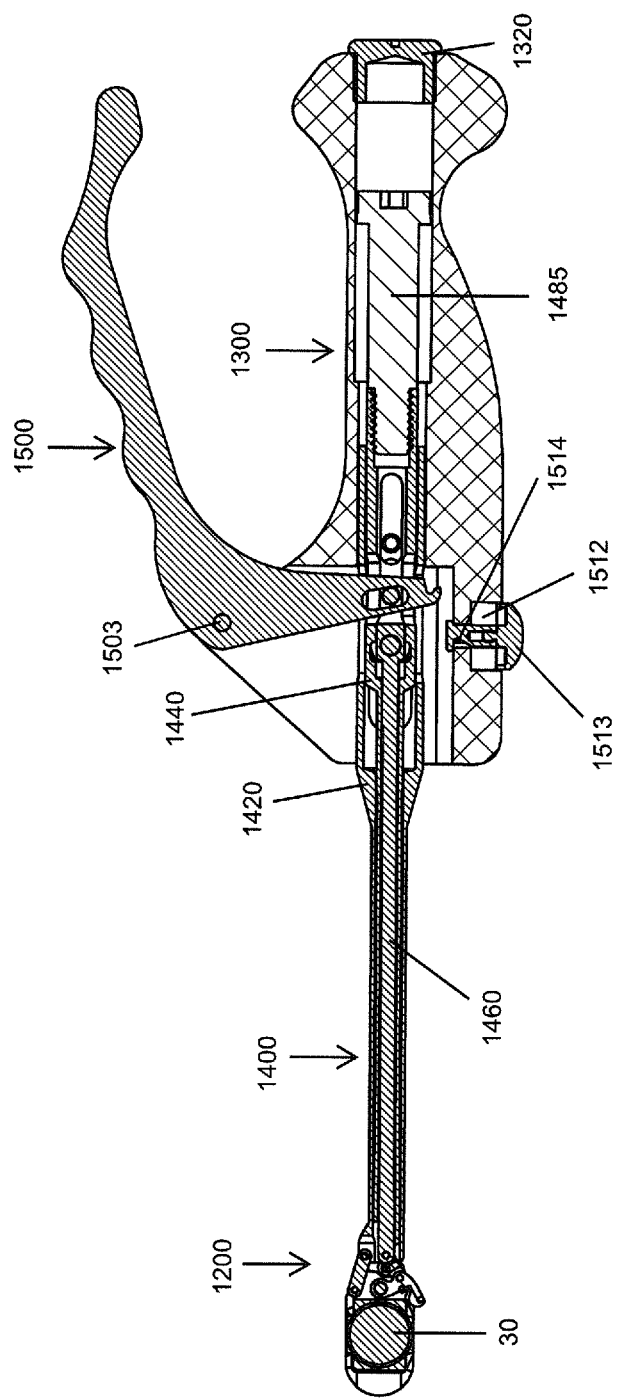
Figure 42:
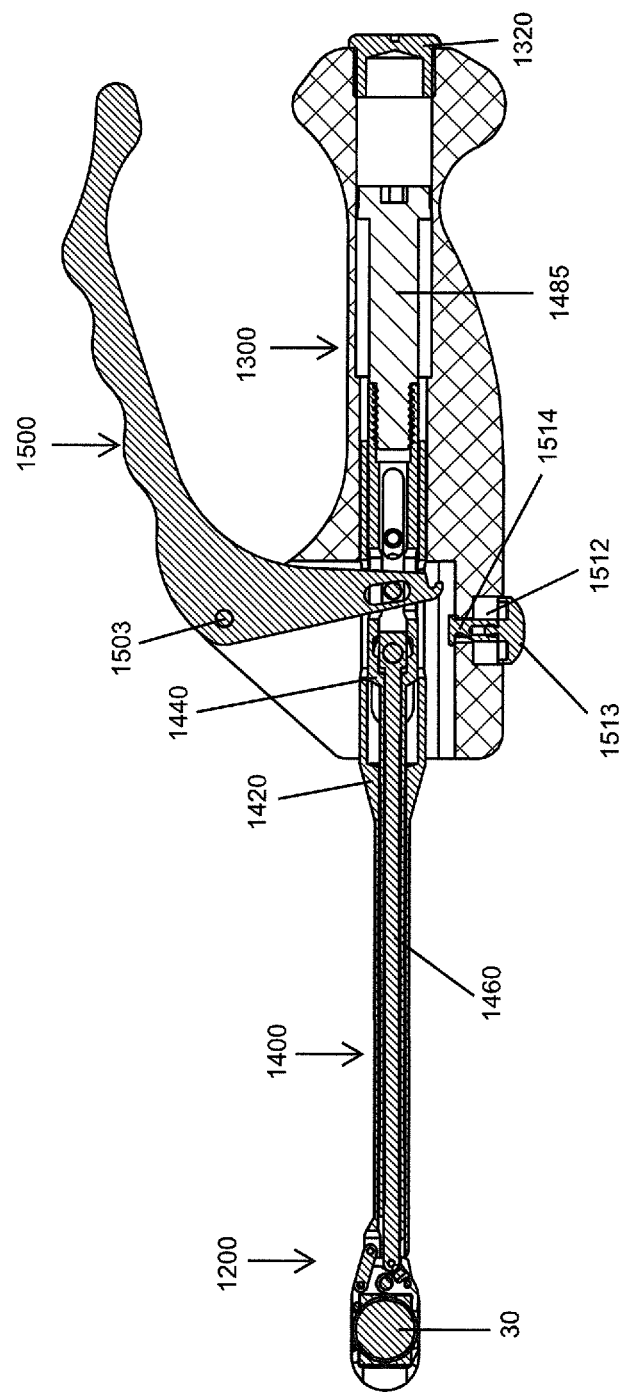
Figure 43:
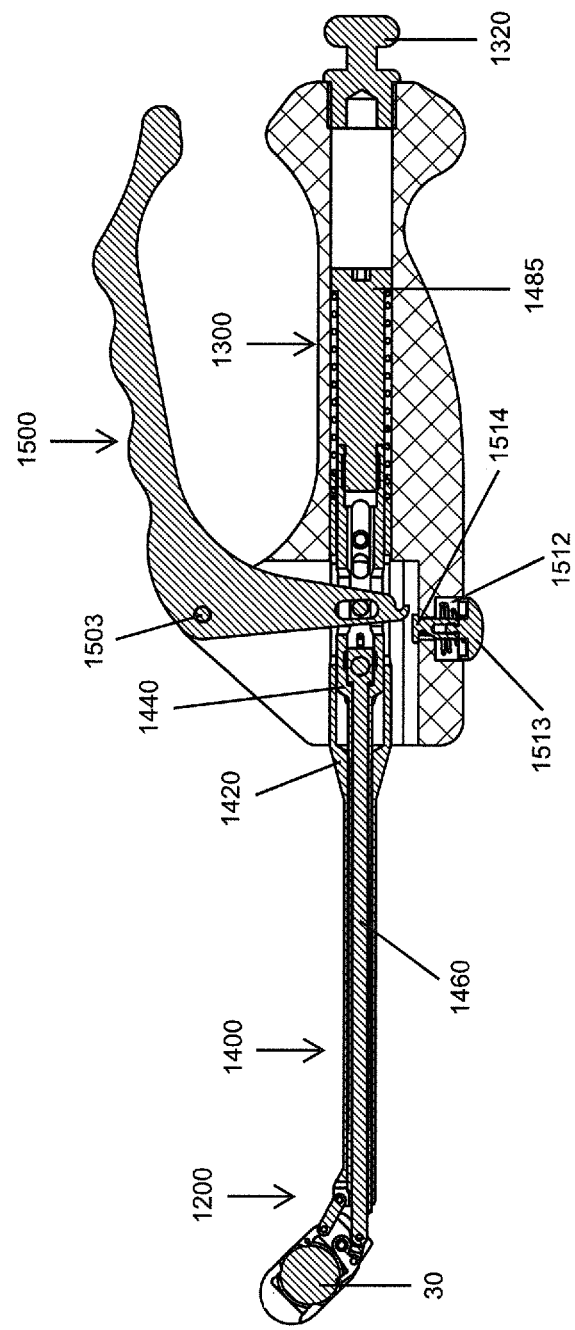
Figure 44:
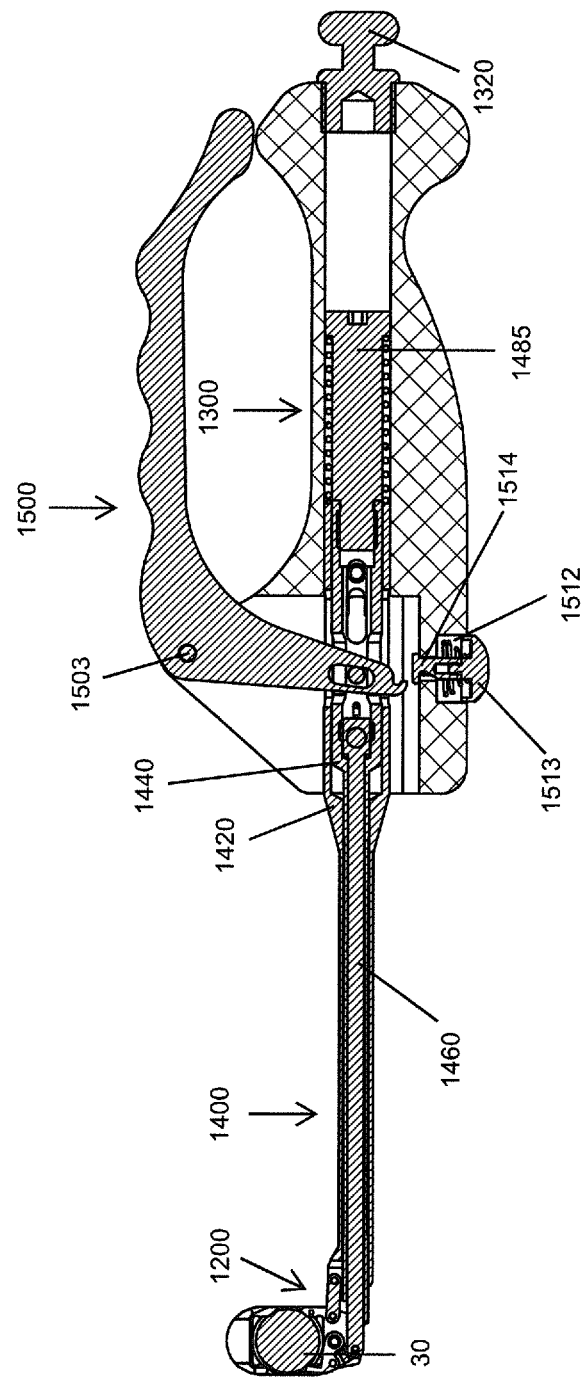

Elongate offset release shaft 1703 comprises a proximal end P, distal end D, camming portion 1705, release shaft abutment shoulder 1712, cap abutment shoulder 1720, lever cap bore, and elongate shaft portion bore 1722. As seen in FIG. 38 proximal end of offset shaft 1703 is fixedly attached to cap 1718 which resides in lever cap bore 1721. Elongate portion of offset shaft adjacent proximal end P is disposed in shaft portion bore 1722 of lever 1701. Parallel to shaft portion bore 1722 resides lever locking post bore 1723. Bore 1723 has tapered end 1725 with a diameter slightly less than that of the remainder of the bore 1723, post 1707 and locking ball 1719. Tapered end 1725 prevents locking ball 1719 and locking post 1707 from escaping locking post bore 1723. Coil Spring 1706 is disposed in bore 1721 extending about offset shaft 1703 and abutting cap 1718 and head 1724 of locking post 1707. Though offset shaft 1703 is fixed in lever 1701, locking ball 1719 and post 1707 may travel within bore 1723. Spring 1706 biases ball 1719 and post 1707 toward tapered end 1725, but allows movement in the opposite direction in reaction to forces placed on ball 1719.

In assembly, offset shaft 1703 is disposed in elongate slot 1302 of handle 1300 and elongate slot 1428 of external shaft 1420. Camming portion 1705 of shaft 1703 resides in bore 1461 of release shaft 1460. Shoulder 1712 of the offset shaft abuts external diameter of release shaft 1460. Distal end of shaft 1703 receives cap 1713 fixedly attached thereon and resides in slot 1451 of rotation shaft 1440. When release lever 1701 is rotated, distal end of offset shaft 1703 cams against the sides of slot 1451 of rotation shaft 1440 moving release shaft 1460 in a proximal or distal direction relative to rotation shaft 1440 thus opening or closing clamping fingers 43, 44.

In the release position, locking ball 1719 is engaged with slot 1449 thus locking instrument 1100 in the open or release configuration. As the release lever 1701 is turned, locking ball 1719 and locking post rotated about the central axis of lever 1701. Locking ball 1719 and locking post 1707 are urged into lever 1701 overcoming the force of spring 1706. When the release lever has reached the locking position, the locking ball is engaged with slot 1450 as spring 1706 biases locking post 1707 and ball 1719 toward instrument 1100. The instrument is now locked in the grasping configuration.

The preferred method of inserting a spinal implant with instrument 2100 is similar to the method of insertion with instrument 100. The release lever 701 of instrument 100 returns to the grasping or locked configuration automatically. Release lever 1701 of instrument 1100 must be returned manually. Although release lever 1701 need be rotated manually, instrument 1100 has fewer moving parts and is relatively less costly to manufacture than instrument 100.

In another form according to the present invention, an insertion instrument 2100 according to the present invention is shown in FIGS. 47-58 and described below. This embodiment is similar to the insertion instruments described above, and particularly the instrument shown in FIGS. 32-46. The insertion instrument 2100 grasps and steers a motion preserving implant in a similar manner to the other insertion instrument embodiments described herein. One distinction is that the instrument 2100 is configured to be more easily cleaned after use. To accomplish this objective, one or more components of the instrument may be a configured to be releasable or easily disassembled, as will be discussed in further detail below.

Figure 47:
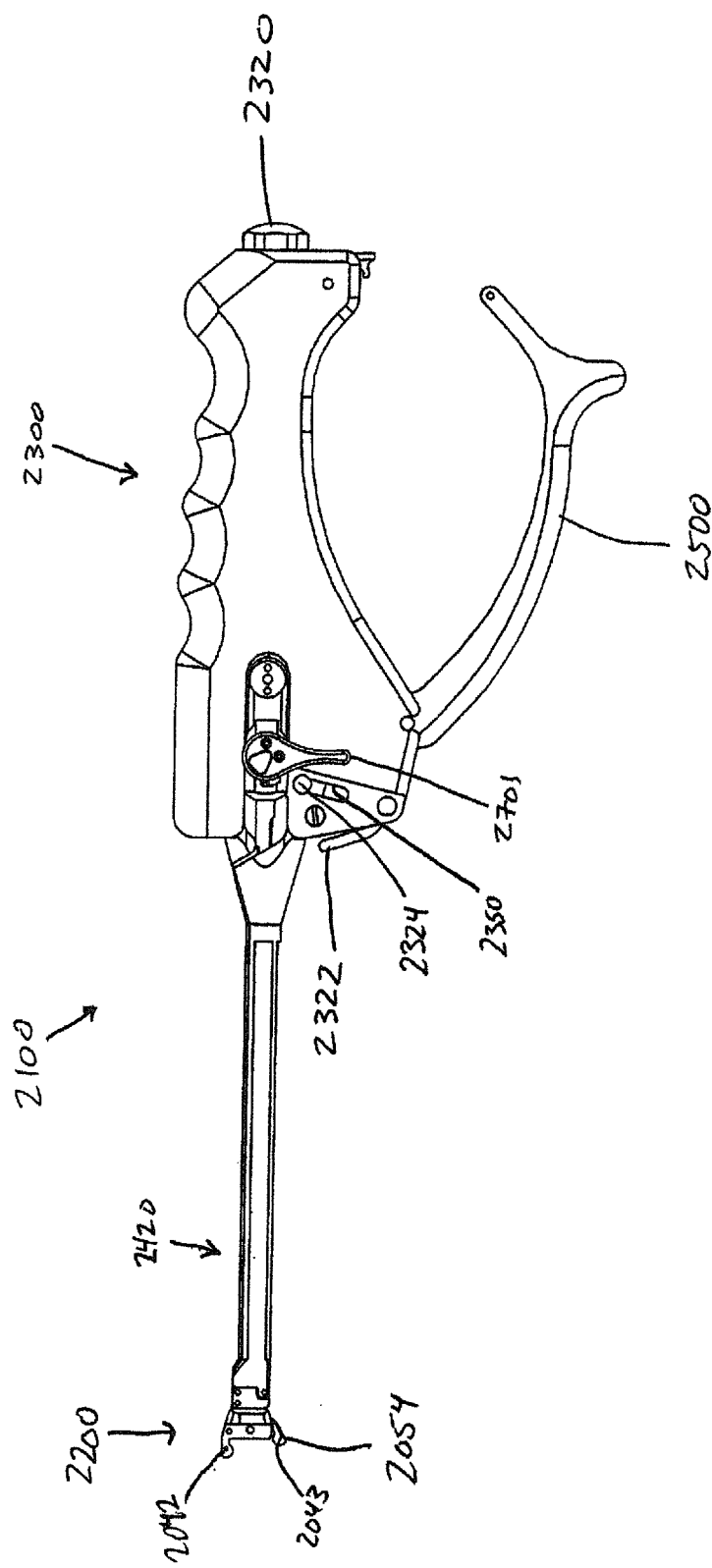
FIGS. 47-51 are various views of an alternate embodiment of an insertion instrument according to the present invention showing the operation of the instrument.
Figure 48:
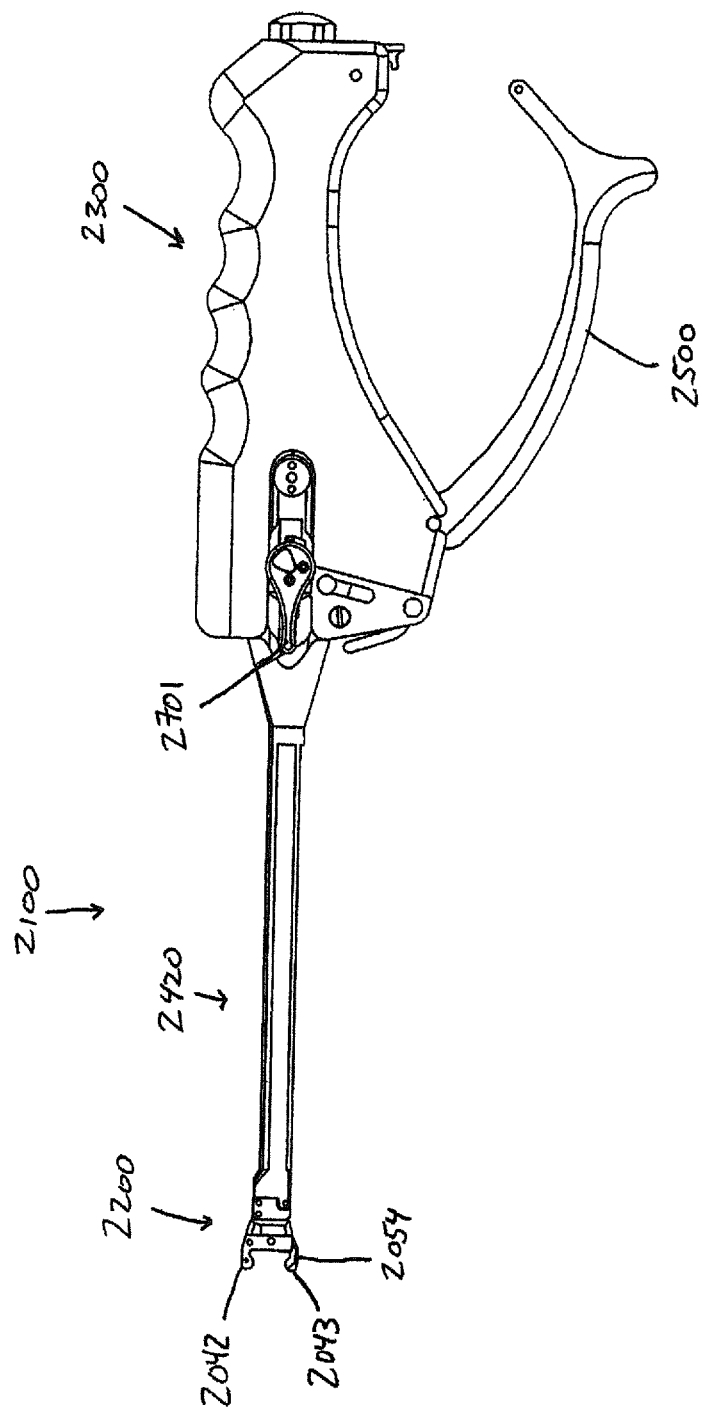
Figure 49:
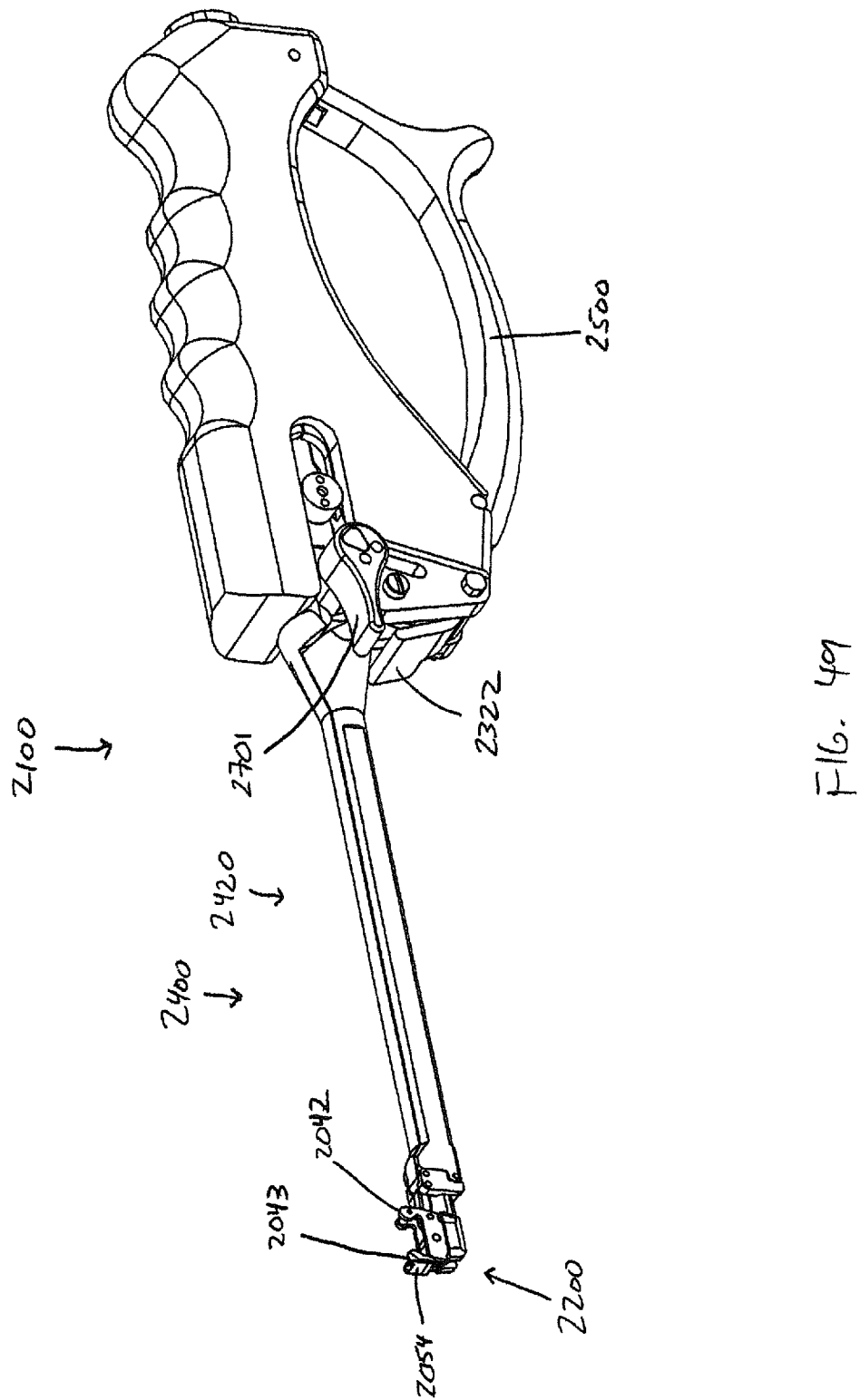
Figure 50:
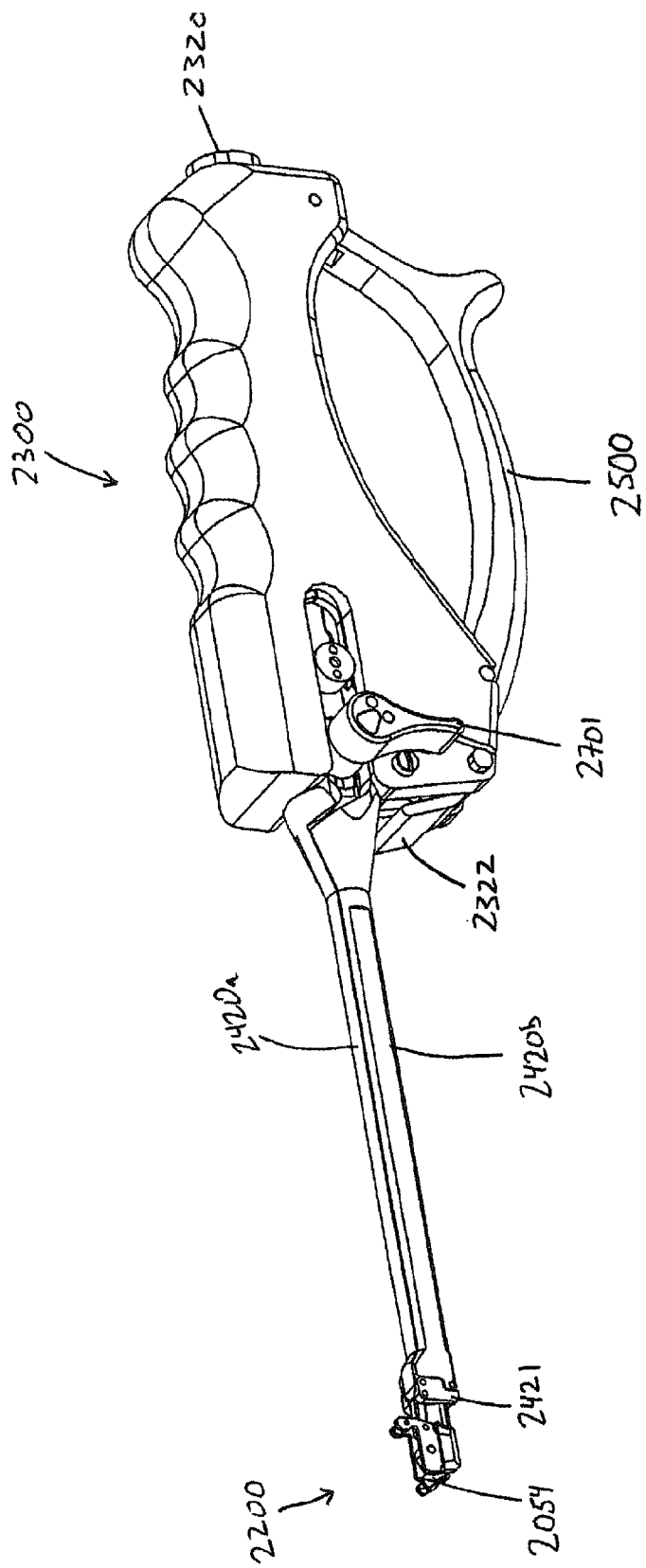

As shown in FIGS. 47-51, similar to instruments 100, 1100, insertion instrument 2100 includes a pivotable gripping mechanism or head portion 2200, which includes a pivotable jaw member 2054 for alternately gripping and releasing an implant. The gripping mechanism 2200 is pivoted from an insertion orientation to a transverse orientation by actuation of a lever 2500 toward the handle 2300. The gripping mechanism 2200 may be rotated approximately 90 degrees by actuation of the lever 2500 as shown in FIG. 49. The pivotable jaw member 2054 is actuated by release lever 2701. In FIGS. 47 and 50, the release lever 2701 is shown in a release orientation, wherein the lever is perpendicular to the tool axis. To grip an implant, the release lever is moved clockwise 90 degrees to move the pivotable jaw member 2054 towards the stationary clamp fingers 2041, 2042 to clamp the implant between the stationary fingers and the fingers 2043, 2044 of the pivotable jaw member 2054. Insertion instrument 2100 is provided with a slap hammer knob 2320 at its distal end for use during insertion of the implant. In addition, a spring-loaded latch member 2340 is provided to hold the lever 2500 in a depressed configuration to hold the gripping mechanism 2200 at a fully rotated position, so that the user may remove their hand from the tool temporarily. This feature is useful in situations when the user must temporarily remove themselves from the implantation site, such as during the use of a fluoroscope to determine the position of the implant within the patient. The lever 2500 may be released by depressing the latch 2340 and releasing the pressure on the lever such that the lever is allowed to return back towards an undepressed orientation.

Figure 51:
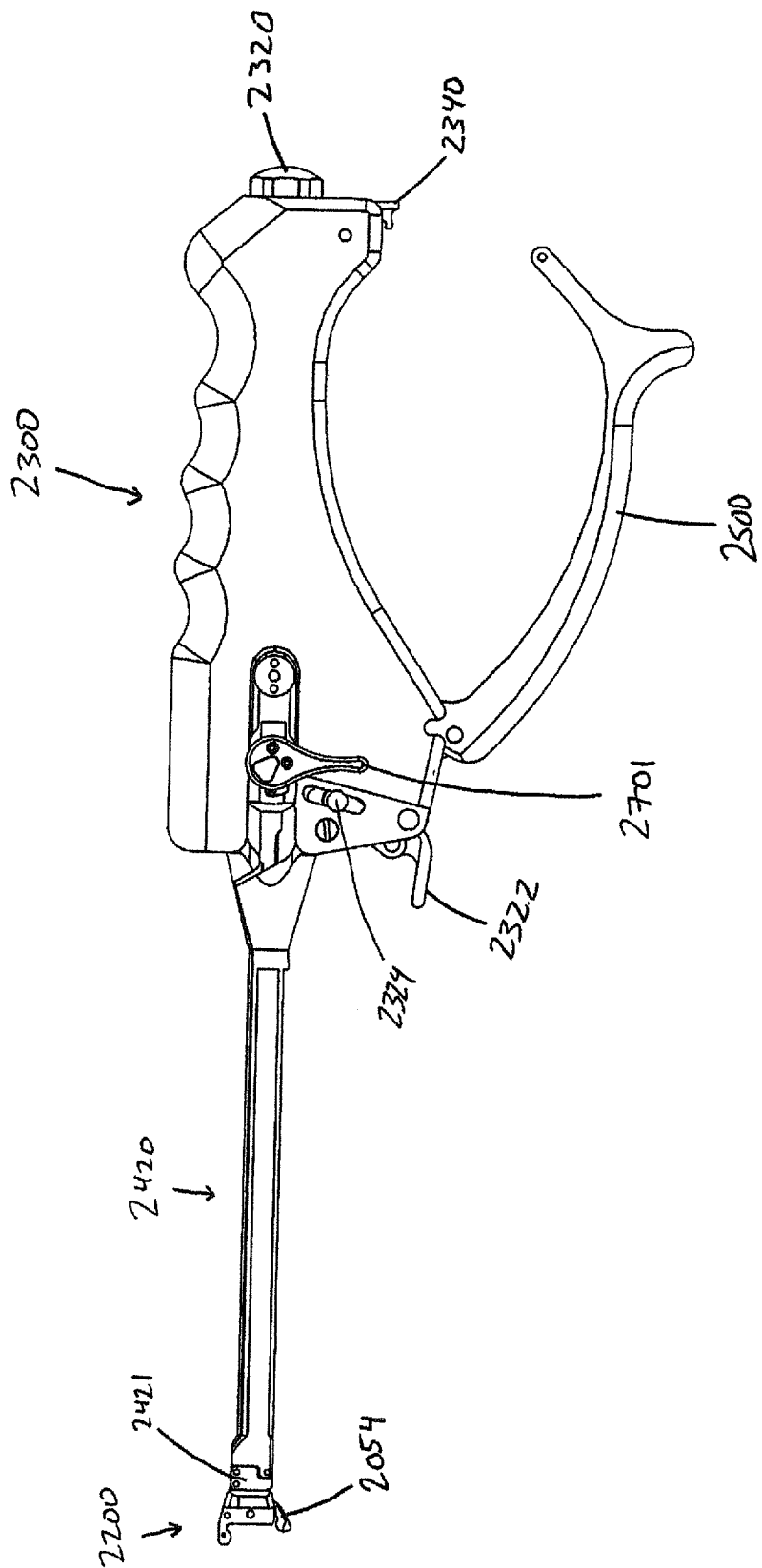
Figure 52:
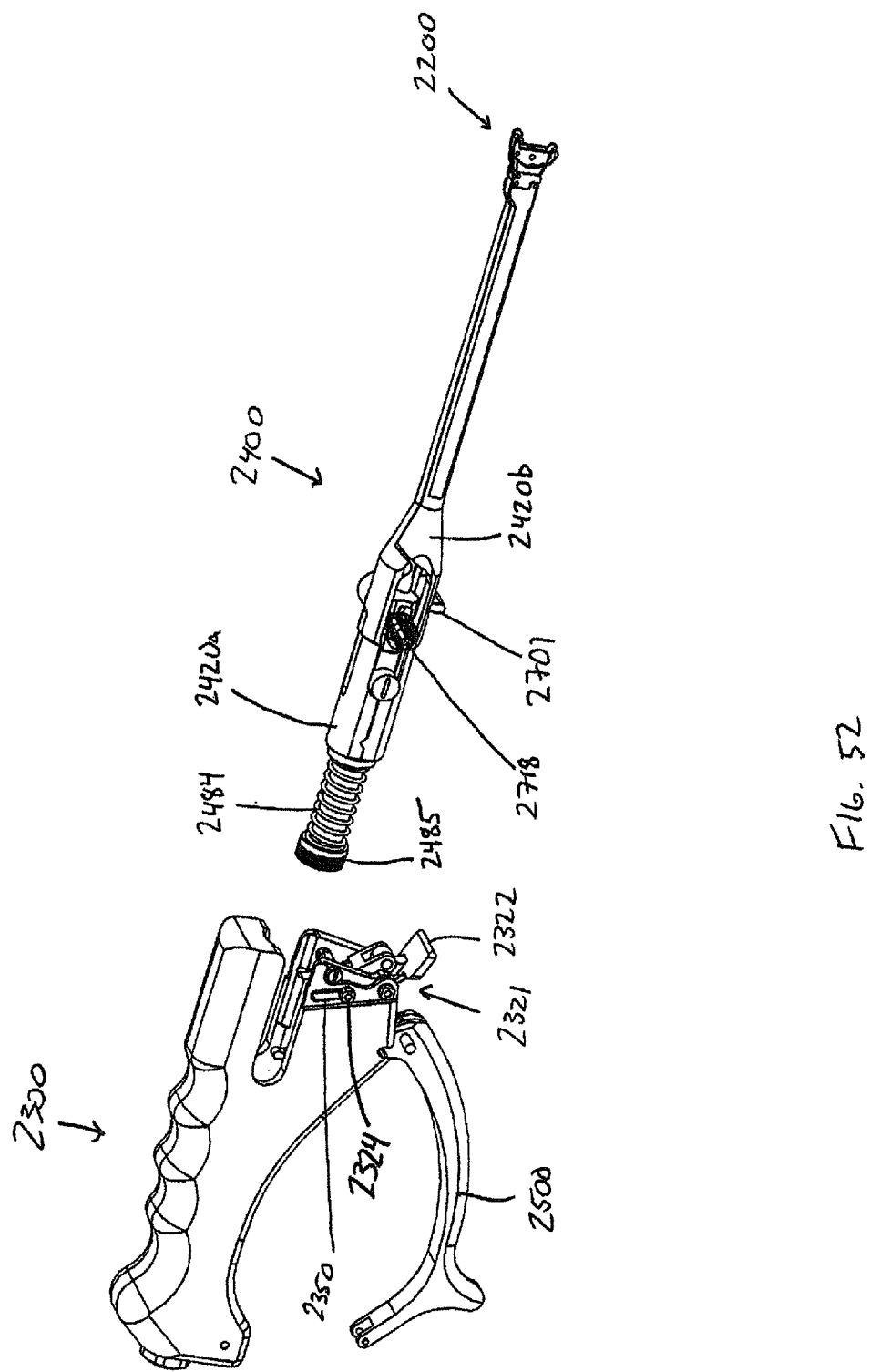
FIG. 52 is a perspective view of the instrument of FIG. 47 showing the shaft assembly of the instrument removed from the handle and actuator portions.
Figure 56:
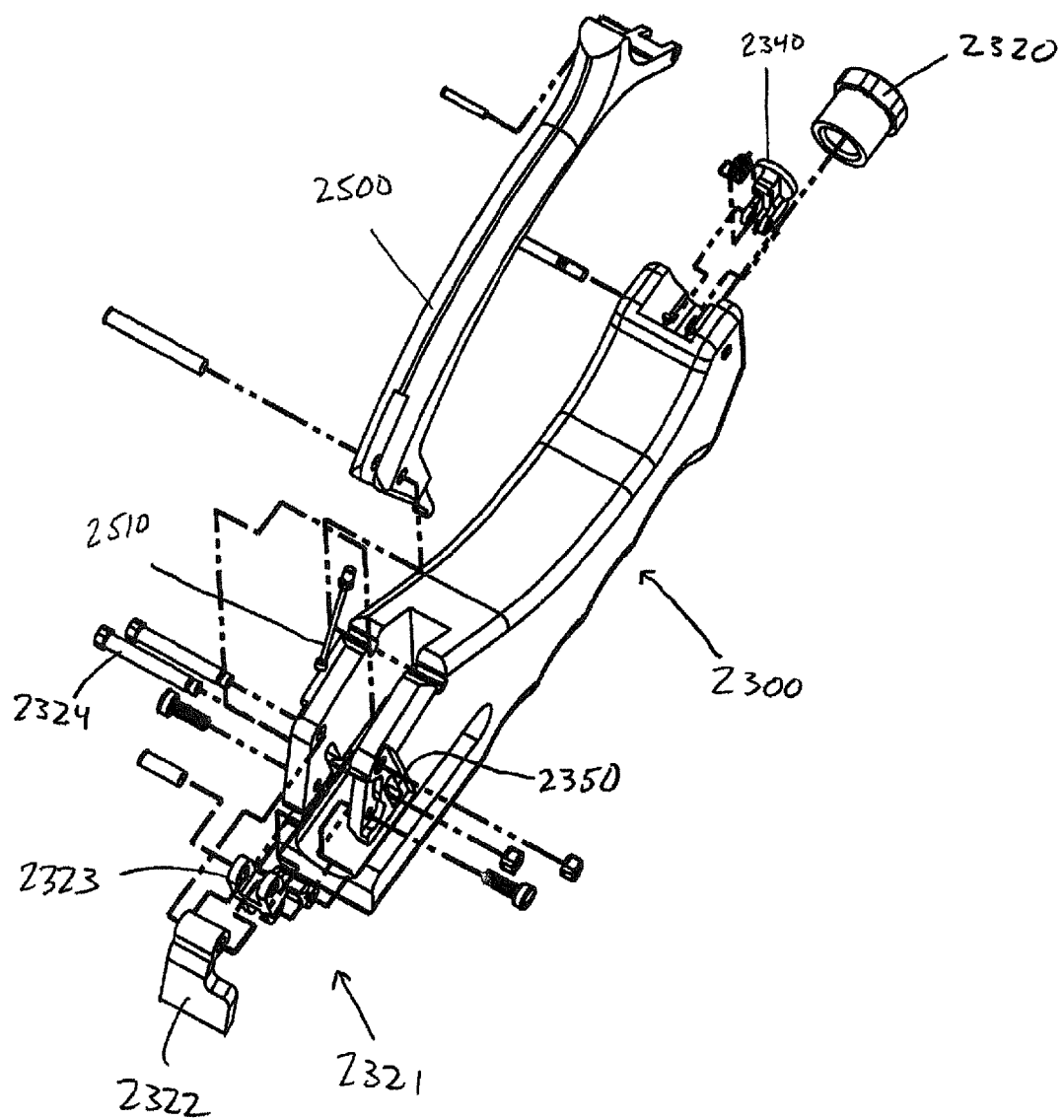

Insertion instrument 2100 is configured for improved cleanability. In this embodiment, the shaft assembly 2400 is releasably connected to the handle 2300 via a latch mechanism 2321 connected to the handle. As shown in FIGS. 51, 52, and 56, the latch mechanism 2321 keeps the shaft assembly 2400 locked to the handle when the latch 2322 is in a closed orientation, and allows the shaft assembly 2400 to be removed when the latch 2322 is in a released orientation, as shown in FIGS. 51 and 52. When the latch 2322 of the latch mechanism 2321 is released, a link member 2323 having a transversely oriented engagement pin 2324, which travels in a channel 2350 of handle 2300, is removed from an indentation in the lower portion 2420b of outer shaft 2420. Lever 2500 is pushed out of the way of the shaft assembly 2400 and the pivot shafts disposed on the lever 2500 are freed from handle due to its connection to the engagement pin 2324 via shaft 2510. The shaft assembly 2400 may then be removed from the handle 2300, as shown in FIG. 52. The shaft assembly 2400 may then be cleaned separately from the handle portion 2300 of the tool.

Figure 53:
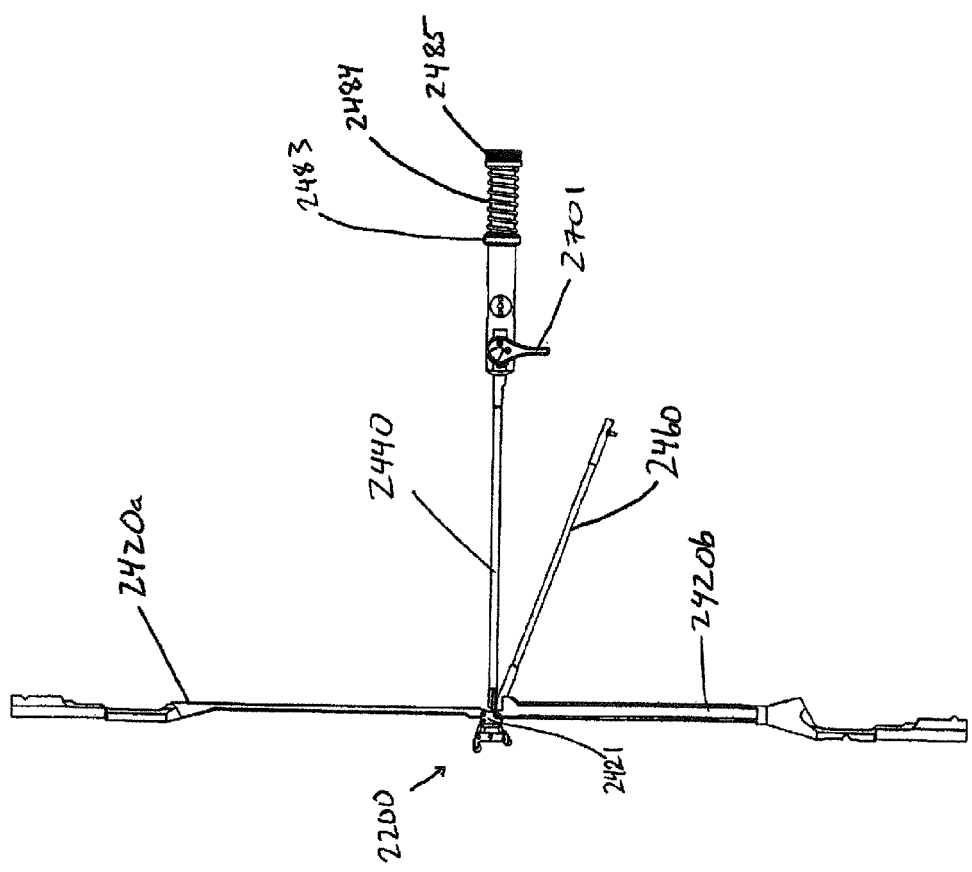
FIG. 53 is an elevation view of the shaft assembly of the instrument of FIG. 47 in an open or cleaning orientation.

The shaft assembly 2400 is further configured for improved cleanability as shown in FIGS. 52 and 53. Outer shaft 2420 has a split configuration and is divided into upper and lower shaft portions 2420a and 2420b. The outer shaft portions 2420a, 2420b are pivotally connected to a yoke 2421 at the distal end of the shaft portions so that the shaft portions may be pivoted apart to expose the interior portions of the outer shaft portions, as well as the middle rotation shaft 2440 and the inner release shaft 2460. The inner release shaft 2460 is removable from inside the middle rotation shaft 2440 at its proximal end to permit the entire shaft assembly to be accessed with cleaning implements, such as a brush.

FIGS. 54-58 are exploded views which show subassemblies of the insertion tool 2100 in greater detail. FIGS. 54 and 55 shows the components of the gripping mechanism 2200, which is similar to the gripping mechanisms described with regard to instruments 100 and 1100. Pivotable jaw member 2054 is pivotally connected to both link member 2053 and upper and lower plate members 2046, 2047. Link member 2053 is connected at its opposite end to the inner release shaft 2460, which in turn pivots the pivotable jaw member 2054 to an open orientation when the inner release shaft 2460 is retracted in a proximal direction. Middle rotation shaft 2440 is pivotally connected to both plate members 2046, 2047 such that gripping mechanism is rotated about end of the middle rotation shaft 2440 when the shaft is moved distally with respect to the outer shaft 2420. Lower plate member 2047 includes a recessed portion 2047a for receiving a projecting portion 39 of the lower shell member of the implant (See FIG. 7). In conjunction with flat 2047b, which engages with a corresponding flat 39a on the lower shell of the implant, the recessed portion 2047a increases the stability of the grip of the implant such that the lower shell is kept from shifting with respect to the lower plate member 2047. The upper plate member 2046 omits these features so that the upper shell member is allowed to pivot to form the wedge configuration.

Figure 58:
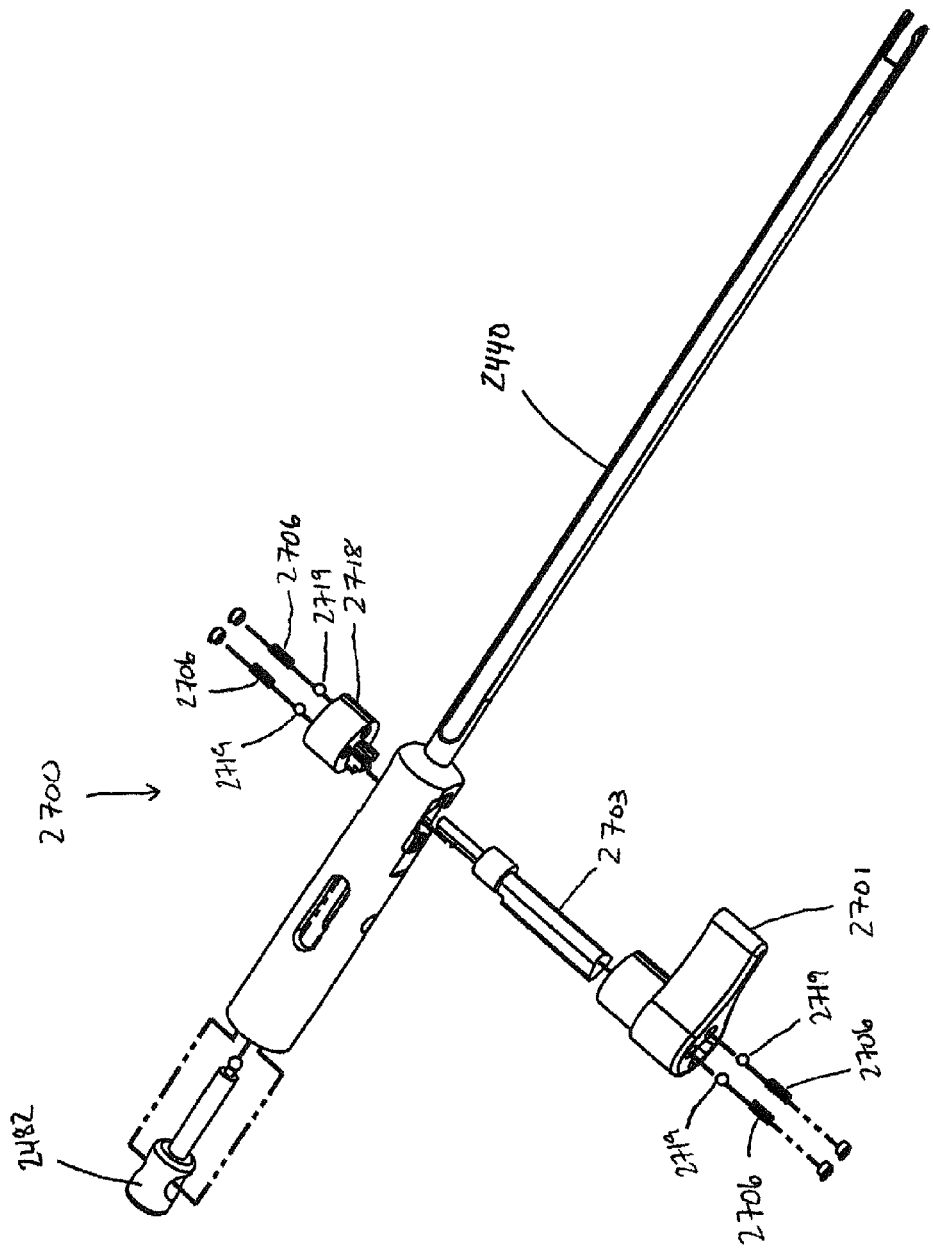

FIG. 58 illustrates components of release mechanism 2700. Release mechanism 2700 comprises release lever 2701, release lever shaft 2703, minor cam 2718, and locking springs 2706 which interact with balls 2719. Balls 2719 interact with detents located on the outer surface of middle shaft 2440 to temporarily hold the release lever 2701 in either the gripping or releasing configurations as desired. The release mechanism 2700 performs the same function as that of previously disclosed mechanisms 700 and 1700 in that it engages inner release shaft 2460 urging release shaft 2460 proximally or distally thus releasing or gripping implant 1 from clamping mechanism 2200. Release mechanism 2700 and handle 2300 are preferably configured to automatically return the release mechanism to the closed or gripping configuration upon release of the lever 2500. In one form, the minor cam 2718 and the body of release lever 2701 are provided with protruding camming surfaces which engage with raised camming surfaces disposed on surfaces of the channel of the handle 2300 on either side when the release mechanism 2700 travels proximally with respect to the handle 2300, i.e., when the tool is being returned to the insertion orientation. Accordingly, the release mechanism 2700 is forced to return to a closed position without need to manually move the release lever 2701 from open orientation to the closed, gripping orientation. This feature helps minimize the size of the gripping mechanism 2200 after the implant has been released in the intervertebral space, reducing the likelihood of causing trauma to the implantation site when removing the tool from the intervertebral space.

Figure 57:
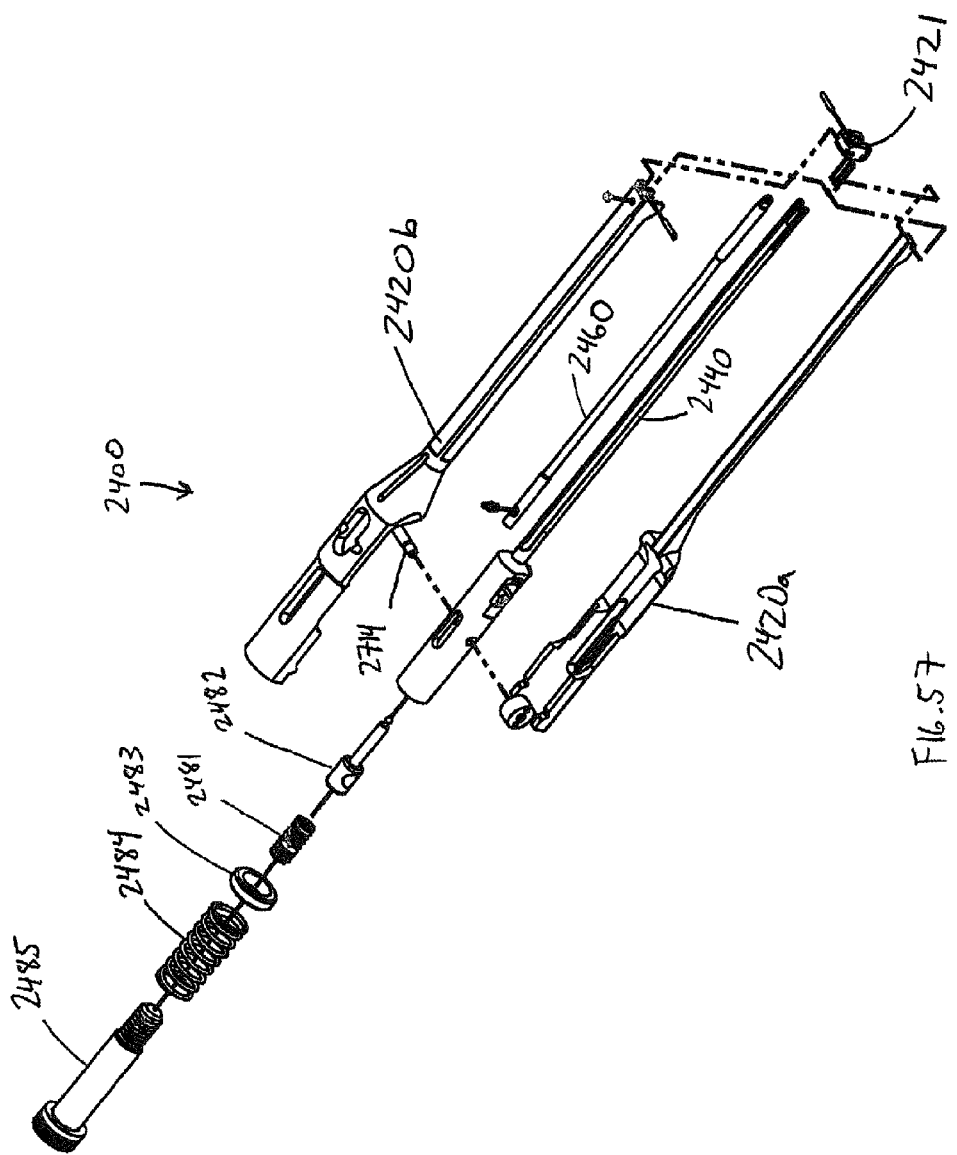

FIG. 57 illustrates components of the shaft assembly 2400, including upper and lower outer shaft portions 2420a, 2420b, middle rotation shaft 2440, inner release shaft 2460, and yoke 2421. Shaft assembly 2400 also includes inner shaft actuator 2482, spring 2481, which biases against the inner shaft actuator 2482 and rotation lever attachment bolt 2714 to bias inner release shaft 2460 distally towards a gripping or closed orientation of the pivotable jaw member 2054. Spring 2484 is biased between the shoulder of shoulder bolt 2485 and washer 2483, which in turn is biased against the proximal end of the outer shaft 2420. Because shoulder bolt 2485 is threaded into middle rotation shaft 2440, lever 2500 compresses spring 2484 when middle rotation shaft 2440 and shoulder bolt 2485 are moved distally as the lever is depressed towards the handle 2300. Thus, spring 2484 urges the rotation shaft 2440 proximally when the lever 2500 is released.

While the insertion tools have described with respect to inserting a two-piece NRD, one of ordinary skill in the art would understand that the tools may be adapted to manipulate other orthopedic devices. Further, while the invention has been described with respect to specific examples including presently preferred modes of carrying out the invention, those skilled in the art will appreciate that the present invention is not limited to the described embodiments and there are numerous variations and permutations of the above described systems and techniques that fall within the spirit and scope of the invention as set forth in the claims.

What is claimed is:
1. A tool for inserting an implant, comprising:
a handle;
a shaft assembly having a longitudinal axis and being operably connected to the handle;
a pivotable head portion pivotally connected to the shaft assembly;
a movable jaw member movably connected to the pivotable head portion for selectively gripping or releasing an implant;
a first actuator operably connected to the shaft assembly operable to selectively pivot the head portion to a plurality of different positions with respect to the shaft assembly;
a second actuator operably connected to the shaft assembly operable to selectively shift the movable jaw member relative to the pivotable head portion;
the shaft assembly and head portion being configured to allow the movable jaw member to be shifted independently of the pivotable head portion, such that the implant may be selectively gripped or released by the movable jaw member in each of the plurality of different positions of the pivotable head portion;
wherein the plurality of different positions of the pivotable head portion include an insertion configuration, wherein a longitudinal axis of the implant connected to the pivotable head portion is substantially parallel to the longitudinal axis of the shaft assembly, and a rotated configuration, wherein the longitudinal axis of the implant connected to the pivotable head portion is transverse to the longitudinal axis of the shaft assembly, and the pivotable head portion is biased to return to the insertion configuration when the pivotable head portion is shifted by the first actuator to the rotated configuration; and a biasing member associated with the shaft assembly operable to bias the movable jaw member toward a gripping orientation for gripping the implant in each of the plurality of different positions of the pivotable head portion.

2. The tool of claim 1, wherein the pivotable head portion further comprises a stationary jaw member opposite from the movable jaw member for gripping the implant therebetween.

3. The tool of claim 1, wherein the movable jaw member comprises a plurality of protuberances for engaging corresponding recessed portions of the implant.

4. The tool of claim 3, wherein the plurality of protuberances of the movable jaw member comprise first and second protuberances, wherein the first and second protuberances each have arcuate configurations.

5. The tool of claim 1, wherein the shaft assembly is releasably connected to the handle portion to allow the shaft assembly to be removed from the handle portion for cleaning.

6. The tool of claim 5, further comprising a latch mechanism for releasably connecting the shaft assembly to the handle, wherein the latch mechanism is shiftable between a closed orientation for keeping the shaft assembly locked to the handle, and a released orientation, for removing the shaft assembly from the handle.

7. The tool of claim 1, wherein the shaft assembly comprises a plurality of shafts including an outer shaft comprised of a plurality of operably connected shaft portions.

8. The tool of claim 7, wherein the outer shaft portions are pivotally connected at a distal end of the shaft assembly.

9. The tool of claim 7, wherein the outer shaft portions include interior surfaces and the shaft portions extend along the longitudinal axis when in a closed orientation with the shaft portions in mating engagement with one another and are configured to shift between the closed orientation and an open orientation with the shaft portions splayed apart from one another for allowing cleaning access to the interior surfaces of the shaft portions.

10. The tool of claim 1, wherein the shaft assembly comprises a first shaft operably connected to the first actuator and the head portion for shifting the head portion via the first actuator, and a second shaft operably connected to the second actuator and the movable jaw member for shifting the movable jaw member via the second actuator.

11. The tool of claim 1, further comprising an additional biasing member associated with the shaft assembly operable to bias the pivotable head portion to return to the insertion configuration when the pivotable head portion is shifted by the first actuator to the rotated configuration.

12. The tool of claim 11, wherein the additional biasing member is a spring operably connected to the shaft assembly.

13. The tool of claim 1, wherein the first actuator comprises a lever configured to shift between a plurality of different positions corresponding with the plurality of different positions of the pivotable head portion, and the tool further comprises a latch member for holding the lever in at least one of the plurality of different positions corresponding to the rotated configuration of the pivotable head portion.

14. A tool for inserting an implant, comprising:
a handle;
a shaft assembly having a longitudinal axis and being operably connected to the handle;
a pivotable head portion pivotally connected to the shaft assembly;
a movable jaw member movably connected to the pivotable head portion for selectively gripping or releasing an implant;
a first actuator operably connected to the shaft assembly operable to selectively pivot the head portion to a plurality of different positions with respect to the shaft assembly;
a second actuator operably connected to the shaft assembly operable to selectively shift the movable jaw member relative to the pivotable head portion;
the shaft assembly and head portion being configured to allow the movable jaw member to be shifted independently of the pivotable head portion, such that the implant may be selectively gripped or released by the movable jaw member in each of the plurality of different positions of the pivotable head portion;
wherein the plurality of different positions of the pivotable head portion include an insertion configuration, wherein a longitudinal axis of the implant connected to the pivotable head portion is substantially parallel to the longitudinal axis of the shaft assembly, and a rotated configuration, wherein the longitudinal axis of the implant connected to the pivotable head portion is transverse to the longitudinal axis of the shaft assembly, and the pivotable head portion is biased to return to the insertion configuration when the pivotable head portion is shifted by the first actuator to the rotated configuration; and
wherein the movable jaw member is shiftable between a gripping orientation for gripping the implant and a releasing orientation for releasing the implant, and the movable jaw member is configured to return automatically to the gripping orientation from the releasing orientation when the pivotable head portion is shifted from the rotated configuration to the insertion configuration.

15. The tool of claim 14, wherein the pivotable head portion further comprises a stationary jaw member opposite from the movable jaw member for gripping the implant therebetween.

16. The tool of claim 14, further comprising a biasing member associated with the shaft assembly operable to bias the pivotable head portion to return to the insertion configuration when the pivotable head portion is shifted by the first actuator to the rotated configuration.

17. The tool of claim 14, wherein the shaft assembly comprises a plurality of shafts including an outer shaft that extends about the other of the plurality of shafts, the outer shaft having a plurality of operably connected shaft portions.

18. The tool of claim 17, wherein the outer shaft portions are pivotally connected at a distal end of the shaft assembly.

19. The tool of claim 17, wherein the outer shaft portions include interior surfaces and the outer shaft portions extend along the longitudinal axis when in a closed orientation with the shaft portions in mating engagement with one another and are configured to shift between the closed orientation and an open orientation with the shaft portions splayed apart from one another for allowing cleaning access to the interior surfaces of the shaft portions.

20. The tool of claim 14, further comprising a latch mechanism for releasably connecting the shaft assembly to the handle, wherein the latch mechanism is shiftable between a closed orientation for keeping the shaft assembly locked to the handle, and a released orientation, for removing the shaft assembly from the handle.

* * * * *